US006245510B1

(12) United States Patent
Staskawicz et al.

(10) Patent No.: US 6,245,510 B1
(45) Date of Patent: Jun. 12, 2001

(54) PRF PROTEIN AND NUCLEIC ACID SEQUENCES: COMPOSITIONS AND METHODS FOR PLANT PATHOGEN RESISTANCE

(75) Inventors: Brian S. Staskawicz, Castro Valley; Giles Edward Oldroyd, San Francisco, both of CA (US); John M. Salmeron, Hillsborough, NC (US); Caius Rommens, Chesterfield, MO (US)

(73) Assignee: The Regents of the University of California, Oakland CA ( * ) Notice: Subject to any disclaimer, the term of this patent is extended or adjusted under 35 U.S.C. 154(b) by 0 days.

(21) Appl. No.: 09/228,246

(22) Filed: Jan. 11, 1999

Related U.S. Application Data

(60) Division of application No. 08/680,327, filed on Jul. 11, 1996, now Pat. No. 5,859,351, which is a continuation-in-part of application No. 08/310,912, filed on Sep. 22, 1994, which is a continuation-in-part of application No. 08/227,360, filed on Apr. 13, 1994, now abandoned.

(51) Int. Cl.[7] .................. C12Q 1/68; C12Q 1/60; C12N 5/04; C12N 5/00; A01H 1/00; C07H 21/04

(52) U.S. Cl. .................. 435/6; 435/419; 435/11; 435/430; 435/418; 435/423; 800/279; 536/23.1; 536/23.6; 536/24.1

(58) Field of Search .................. 435/419, 320.1, 435/6, 423, 11, 430, 418; 800/230, 279; 536/23.1, 23.6, 24.1; 935/77, 78

(56) References Cited

FOREIGN PATENT DOCUMENTS

WO 95 05731 3/1995 (WO).
WO 95 28423 10/1995 (WO).

OTHER PUBLICATIONS

Salmeron et al. Genetic dissection of bacterial speck disease resistance in tomato. Euphytica, vol. 79, pp. 195–200, May 1994.

Ariat et al., "PopA1, a protein which induces a hypersensitivity–like response on specific petunia genotypes, is secreted via the Hrp pathway of *Pseudomonas solarscaarum*," *EMBO J.* 13:543–553, 1994.

Dong et al., "Induction of Arabidopsis defense genes by virulent and avirulent *Pseudomonas syringae* strains and by a cloned avirulence gene," *The Plant Cell* 3:61–72, 1991.

Ellingboe, "Changing concepts in host–pathogen genetics," Ann. Rev. Phytopathol 19:125–143, 1981.

Flor, "Current status of the gene–for–gene concept," Ann. Rev. Phytopathol 9:275–296, 1971.

Gabriel, "Working models of specific recognition in plant—microbe interactions," Annu. Rev. Phytopathl 28:365–391, 1990.

Hahn et al., "Cultivar–specific elicitation of barley defense reactions by the phytotoxic peptide NIP1 from *Phynchosporium secalis*," Molecular Plant—Microbe Interactions 6:745–754, 1993.

(List continued on next page.)

Primary Examiner—W. Gary Jones
Assistant Examiner—Cynthia B. Wilder
(74) Attorney, Agent, or Firm—Klarquist Sparkman Campbell Leigh & Whinston, LLP

(57) ABSTRACT

The Prf gene of tomato has been cloned and analyzed. Prf encodes a protein with leucine-rich repeat, nucleotide binding, and leucine zipper motifs, identifying it as a member of the resistance gene class that includes RPS2, RPM1, N and L6. When expressed in transgenic plants, Prf confers Fenthion sensitivity and resistance to a wide variety of phytopathogens, including not only *Pseudomonas syringae* but also unrelated pathogens such as *Xanthomonas campestris*.

12 Claims, 34 Drawing Sheets

OTHER PUBLICATIONS

Innes et al., "Molecular analysis of avirulence gene avrRpt2 and identification of a putative regulatory sequence common to all known *Pseudomonas syringae* avirulance genes," *J. Bacteriol.* 175:4859–4869, 1993.

Johel et al., "Reductase activity encoded by the HM1 disease resistance gene in maize," *Science* 258:985–987, 1992.

Joosten et al., "Host resistance to a fungal tomato pathogen lost by a single base–pair change in an avirulence gene," *Nature* 367:384–386, 1994.

Keen, "Host range determinants in plant pathogens and symbiants," *Ann. Rev. Microbiol.* 42:421–440, 1988.

Keen, "Plant disease resistance genes: interactions with pathogens and their improved utilization to control plant diseases," *Biotechnology in Plant Disease Control*, 65–88, 1993.

Kobayashi et al., "A gene from *Pseudomonas syringae* pv. *glycinea* with homology to avirulence gene D from P. s. pv. tomato but oevoid to the avirulence phenotype," *Molecular Plant—Microbe Interactions* 3:103–111, 1990.

Kobayashi et al., "Molecular characterization of avirulence gene D from *Pseudomonas syringae* pv. tomato," Molecular Plant—Microbe Interactions 3:94–102, 1990.

Kunkel et al., "RPS2, an Arabidopsis disease resistance locus specifying recognition of *Pseudomonas syringae* strains expressing the avirulence gene avrRpt2," *The Plant Cell* 5:865–875, 1993.

Lister et al., "Recombinant inbred lines for mapping RFLP and phenotypic markers in *Arabidopsis thaliana*," *The Plant Journal* 4:745–750, 1993.

Martin et al., "Map–based cloning of a protein kinase gene conferring disease resistance in tomato," *Science* 262:1432–1436, 1993.

Midland et al., "The structures of syringolides 1 and 2, Novel c–glycosidic elicitors from *Pseudomonas syringae* pv. tomato," *J. Org. Chem.* 58:2940–2945, 1993.

Staskowicz et al., "Molecular characterization of cloned avirulence genes from race 0 and race 1 of *Pseudomonas syringae* pv. *glycinea*," *J. Bacterial.* 169:5789–5794, 1987.

Van den Ackerveken et al., "Molecular analysis of the avirulence gene avr9 of the fungal tomato pathogen *Cladosporuim fulvum* fully supports the gene–for–gene hypothesis," *The Plant Journal* 2:359–366, 1992.

Wanner et al., "Recognition of the avirulence gene avrB from *Pseudomonas syringae* pv. *glycinea* by *Arabidopsis thaliana*," *Molecular Plant—Microbe Interactions* 6:582–591, 1993.

Whalen et al., "Identification of *Pseudomonas syringae* pathogens of Arabidopsis and a bacterial locus determining avirulence on both Arabidopsis and soybean," *The Plant Cell* 3:49–59, 1991.

Yu et al., "Arabidopsis mutations at the RPS2 locus results in loss of resistance to *Pseudomonas syringae* strains expressing the avirulence gene avrRpt2," *Molecular Plant—Microbe Interactions* 6:434–443, 1993.

Bent et al., *Science* 265:1856–1860, 1994.

Bunz et al., *Proc. Natl. Acad. Sci. USA* 90:11014–11018, 1993.

Burbelo et al., *Proc. Natl. Acad. Sci. USA* 90:11543–11547, 1993.

Dalrymple et al., "Cloning and characterisation of cDNA clones encoding two *Babesia bovis* proteins with homologous amino– and carboxy–terminal domains," *Molecular and Biochemical Parasitology* 59:181–190, 1993.

Dean, "Advantages of Arabidopsis for cloning plant genes," *Phil. Trans. R. Soc. Lond.* 342:189–195, 1993.

Lu et al., *Biochemical and Biophysical Research Communications* 193(2):779–786, 1993.

Mindrinos et al., *Cell* 78:1089–1099, 1994.

Kearney et al., "Molecular basis for evasion of plant host defence in bacterial spot disease of pepper," *Nature*, 332:541–543, 1988.

Lawrence et al., "The L6 gene for flax rust resistance is related to the Arabidopsis bacterial gene RPS2 and the tobacco viral resistance gene N," *The Plant Cell*, 7:1195–1206, 1995.

Whitman et al., "The product of the tobacco mosaic virus resistance gene N: Similarity to toll and the interleukin–1 receptor," *Cell*, 78:1101–1115, 1994.

Newman et al., "Genes galore: A summary of methods for accessing results from the large–scale partial sequencing of anonymous Arabidopsis cDNA clones," *Plant Physiology* 106:1241–1255, 1994.

Kobayashi et al., *Molecular Plant—Microbe Interactions* 3(2):94–102, 103–111, 1990.

Kunkel, et al., *The Plant Cell* 5:865–875, 1993.

Bisgrove et al., "A disease resistance gene in Arabidopsis with specificity for two different pathogen avirulence genes," *Plant Cell* 6:927–933, 1994.

Boyes and Nasrallah, "Physical linkage of the SLG and SRK genes at the self–incompatibility locus of *Brassica oleracea*," *Mol. Gen. Genet.* 236:369–373, 1993.

Braun et al., "Amino–terminal leucine–rich repeats in gonadotropin receptors determine hormone selectivity," *EMBO J.* 10:1885–1890, 1991.

Carland and Staskawicz, "Genetic characterization of the Pto locus of tomato: semi–dominance and cosegregation of resistance to *Pseudomonas syringae* pathovar tomato and sensitivity to the insecticide Fenthion," *Mol. Gen. Genet.* 239:17–27, 1993.

Dangl, "Piece de résistance: novel classes of plant disease resistance genes," *Cell* 80:363–366, 1995.

Gabriel et al., "Gene–for–gene interactions of five cloned avirulence genes from *Xanthomonas campestris* pv. *malvacearum* with specific resistance genes in cotton," *Proc. Natl. Acad. Sci. USA* 83:6415–6419, 1986.

Grant et al., "Structure of the Arabidopsis RPM1 gene enabling dual specificity disease resistance," *Science* 269:843–846, 1995.

Hashimoto et al., "The Toll gene of Drosophila, required for dorsal–ventral embryonic polarity, appears to encode a transmembrane protein," *Cell* 52, 269–279, 1988.

He et al., "*Pseudomonas syringae* pv. syringae Harpin$_{Pss}$: A protein that is secreted via the Hrp pathway and elicits the hypersensitive response in plants," *Cell* 73:1255–1266, 1993.

Hébert et al., "Partial functional mapping of the human interleukin–8 type A receptor," *J. Biol. Chem.* 268:18549–18553, 1993.

Hunter, "Protein kinases and phosphatases: the yin and yang of protein phosphorylation and signaling," *Cell* 80:225–236, 1995.

Jones et al., "Isolation of the tomato Cf–9 gene for resistance to *Cladosporium fulvum* by transposon tagging," *Science* 266:789–792, 1994.

Kataoka et al., "DNA sequence and characterizaton of the *S. cerevisiae* gene encoding adenylate cyclase," *Cell* 43:493–505, 1985.

Keen, "Gene–for–gene complementarity in plant–pathogen interactions," *Annu. Rev. Genet.* 24:447–463, 1990.

Kobe and Deisenhofer, "The leucine–rich repeat: a versatile binding motif," *Trends Biochem. Sci.* 19:415–421, 1994.

Long and Staskawicz, "Prokaryotic plant parasites," *Cell* 73:921–935, 1993.

Martin et al., "A member of the tomato Pto gene family confers sensitivity to Fenthion resulting in rapid cell death," *Plant Cell* 6:1543–1552, 1994.

Rodrigues and Park, "Dimerization mediated through a leucine zipper activates the oncogenic potential of the met receptor tyrosine kinase," *Mol. Cell Biol.* 13:6711–6722, 1993.

Rommens et al., "Use of a gene expression system based on potato virus X to rapidly identify and characterize a tomato Pto homolog that controls Fenthion sensitivity," *Plant Cell* 7:249–257, 1995.

Ronald et al., "The cloned avirulence gene avrPto induces disease resistance in tomato cultivars containing the Pto resistance gene," *J. Bacteriol.* 174:1604–1611, 1992.

Ryals et al., "Signal transduction in systemic acquired resistance," *Proc. Natl. Acad. Sci. USA* 92:4202–4205, 1995.

Salmeron and Staskawicz, "Molecular characterization and hrp dependence of the avirulence gene avrPto from *Pseudomonas syringae* pv. tomato," *Mol. Gen. Genet.* 239:6–16, 1993.

Salmeron et al., "Tomato mutants altered in bacterial disease resistance provide evidence for a new locus controlling pathogen recognition," *Plant Cell* 6:511–520, 1994.

Staskawicz et al., "Molecular genetics of plant disease resistance," *Science* 268:661–667, 1995.

Stein et al., "Molecular cloning of a putative receptor protein kinase gene encoded at the self–incompatibility locus of *Brassica oleracea*," *Proc. Natl. Acad. Sci. USA* 88:8816–8820, 1991.

Sudupak et al., "Unequal exchange and meiotic instability of disease–resistance genes in the Rp1 region of maize," *Genetics* 133:119–125, 1993.

Wei et al., "Harpin, elicitor of the hypersensitive response produced by the plant pathogen *Erwinia amylovora*," *Science* 257:85–88, 1992.

Zhou et al., "The tomato gene Pti1 encodes a serine/threonine kinase that is phosphorylated by Pto and is involved in the hypersensitive response," *Cell* 83:925–935, 1995.

Stam, M., et al., "The silence of genes in transgenic plants," *Ann. Bot.* 79:3–12, 1997.

Koziel M.G., et al., "Optimizing expression of transgenes with an emphasis on post–transcriptional events," *Plant Mol. Biol.* 32:393–405, 1996.

Smith, C.J.S., et al., "Antisense RNA inhibition of polygalacturonase gene expression in transgenic tomatoes," *Nature* 334:724–726, Aug. 25, 1988.

Hongyong F., et al., "Sink– and vascular–associated sucrose synthase functions are encoded by different gene classes in potato," *Plant Cell* 7:1369–1385, Sep. 1995.

Waldron C., et al., "Characterization of a genomic sequence coding for potato multicystatin, an eight–domain cysteine proteinase inhibitor," *Plant Mol. Biol.* 23:801–812, 1993.

De Block M., "The cell biology of plant transformation: Current state, problems, prospects and the implications for the plant breeding," *Euphytica* 71:1–14, 1993.

Martin et al., "High–resolution linkage analysis and physical characterization of the Pto bacterial resistance locus in tomato," *Molecular Plant—Microbe Interactions* 6:26–34, 1993.

Pitblado et al., "Genetic basis of resistance to *Pseudomonas syringae* pv. tomato in field tomatoes," *Canadian Journal of Plant Pathology* 5:251–255, 1983.

Saraste et al., "The P–loop—a common motif in ATP– and GTP–binding proteins," *Trends Biochem. Sci.* 15:430–434, 1990.

Song et al., "A receptor kinase–like protein encoded by the rice disease resistance gene, Xa21," *Science* 270:1804–1806, 1995.

Stotz et al., "Structure and expression of an inhibitor of fungal polygalacturonases from tomato," *Plant Molecular Biology* 25:607–617, 1994.

van Kan et al., "Cloning and characterization of cDNA of avirulence gene avr9 of the fungal pathogen *Cladosporium fulvum*, causal agent of tomato leaf mold," *Molecular Plant—Microbe Interactions* 4:52–59, 1991.

Salmeron, J.M., et al., "Tomato Prf is a member of the leucine–rich repeat class of plant defense resistance genes and lies embedded within the Pto kinase gene cluster," *Cell*, vol. 86, pp. 123–133, Jul. 12, 1996.

Salmeron, J.M., et al., "*Lycopersicon esculentum* PRF (Prf) gene, complete cds.," EMBL Sequence Database, Release 49, Accession No. U65391, Aug. 30, 1996.

Chasan R., "Plant–Pathogen Encounters in Edinburgh," *Plant Cell*, vol. 6, pp. 1332–1341, Oct. 1, 1994.

Wit De P J G M, "Cold Spring Harbor Conference On 'Molecular Biology of Disease Resistant Genes in Plants,'" *Molecular Breeding: New Strategies in Plant Improvement*, vol. 1, pp. 203–206, 1995.

Martin, G.B., et al., "Construction of a yeast artificial chromosome library of tomato and identification of cloned segments linked to two disease resistance loci," *Mol. Gen. Genet.*, vol. 233, pp. 25–32, 1992.

Tanksley, S.D., et al., "Chromosome landing: a paradigm for map–based gene cloning in plants with large genomes," *Trends in Genetics*, vol. 11, No. 2, pp. 63–68, Feb. 1995.

Shah, D.M., et al., "Resistance to Diseases and insects in Transgenic Plants: Progress and Applications to Agriculture," *Trends in Biotechnology*, vol. 13, No. 9, pp. 363–368, Sep. 1995.

Rommens, C.M.T., et al., "Intergeneric transfer and functional expression of the tomato disease resistance gene Pto," *The Plant Cell*, vol. 7, pp. 1537–1544, Oct. 1995.

Thilmony, R.L., et al., "Expression of the tomato Pto gene in tobacco enhances resistance to *Pseudomonas syringae* pv *tabaci* expressing avrPto," *The Plant Cell*, vol. 7, pp. 1529–1536, Oct. 1995.

6.2 kb →
5.1 kb →

```
          10        20        30        40        50        60
           *         *         *         *         *         *
ATGGCCAAGGAGTGTCGCGATGCAATAGGTACTATAAACCTTGTGAAGGGCCAGCATTTA 70        80        90       100       110       120
           *         *         *         *         *         *
GACAGAAGGACCACTAATCAATTGGAGGATGCTATAAAGCACCTAACACATGTTGCTGTA 130       140       150       160       170       180
           *         *         *         *         *         *
TTTCTCACAAATCTGGAGAAGCGTCACCCTGCTAATGGAATATCTATACATCTTAGGCCT 190       200       210       220       230       240
           *         *         *         *         *         *
CTATTTTTAGAAGCTCATGATGGCTTTTCTCTGATGTGTTCTCATCCTCCTCGTTCTCAG 250       260       270       280       290       300
           *         *         *         *         *         *
TTTACCGTTAAACTGGATAACATTGCTGAGAAATTCAAATCTTCAAAGGCGTCAAGATCA 310       320       330       340       350       360
           *         *         *         *         *         *
ACAAGGCAAGTGATCCCAGAGCTGCTGCAAATAATTGAACCCGAGAATATTGCTAAGCGA 370       380       390       400       410       420
           *         *         *         *         *         *
ATCAAAGCTTCAAAGCCATCAAGATCATCTAGCCCAATCACTGTGGATATGGTGGGGTTT 430       440       450       460       470       480
           *         *         *         *         *         *
ATCGAATCCTTGCTTGGTTCTGTTCATCGTGCATTGTTCTTTATCAGTGCAGGGCCTCCT 490       500       510       520       530       540
           *         *         *         *         *         *
GTGTCTATGCTTGACAAGAAGCTTCGACATCTACAAGTCTTCTTTAGACTAATTTCAAAG 550       560       570       580       590       600
           *         *         *         *         *         *
CGGGGCATTGAGCATGAGAGTATGAAGGATCTCTTCTACCATGTTGAGGATGTAGCTTAC 610       620       630       640       650       660
           *         *         *         *         *         *
ACTGCAGCACAACTATGTGTCTTGGGGTCGAGCTGCCATATGGATGACGAGTTCTCTAAA 670       680       690       700       710       720
           *         *         *         *         *         *
TTTCTGGAAAGGATAAGTCGTCCTTTTAGCCCAGGATTGAGGCAGGTTTATCTCAATGCC 730       740       750       760       770       780
           *         *         *         *         *         *
TTGATAGGGTTAAATTCATCAAGATCAAAGACTACAATGAATGCCAAATATATGCTTGAT 790       800       810       820       830       840
           *         *         *         *         *         *
TTTGTTAGTGCTCTCCAAGATGATCTGAGACTAAGATGTGATAATCGAATTCGATGGCTC
```

FIG. 9A

```
         850         860         870         880         890         900
          *           *           *           *           *           *
CAACGAGGACTTTCTTACCTTTGTCGATTCCTCAGGGACATAGAATCTTATCCTGTTTCA 910         920         930         940         950         960
          *           *           *           *           *           *
CATCGACAACTGATTTCTCTTCAATTGAATATGGAAGATCTGGCTATTGGGTCTGCAAAT 970         980         990        1000        1010        1020
          *           *           *           *           *           *
GCCATCTACTCCTATGATGAGGATATGGATAAGACTAGTGAAATAGACCATGAGCTTTTT 1030        1040        1050        1060        1070        1080
          *           *           *           *           *           *
CATTTGCAAATGAAGTTTAATTATGTTAAAGTAGAGGTTGATCTGATTCGTCTACAAAAC 1090        1100        1110        1120        1130        1140
          *           *           *           *           *           *
ATTCAAGGCACCATAATAGTTCCTATGAAAGATCTGATCGACTATGTTTGGGAAGAGCTG 1150        1160        1170        1180        1190        1200
          *           *           *           *           *           *
ATGTTCTTTAGAAGTTATTTCATGGATGCATTCGACCAGTTTAAAGAGCAGACCAGGATA 1210        1220        1230        1240        1250        1260
          *           *           *           *           *           *
ACTGTTATTTTGAACTATATTCAGTCTGCAGTTAGTCAAGCATGGTCAGTCTGTGATTCT 1270        1280        1290        1300        1310        1320
          *           *           *           *           *           *
CTTTGTCATGACTTGAATCAAAATGACTTGGCCAGGGAAATTAATTGCTTGCATTTTCAA 1330        1340        1350        1360        1370        1380
          *           *           *           *           *           *
TTGCTTCTTAAGTTCAAGTTTATCAAGGTCGCTATTAGACAGATGTGTCCCAGCATTTCT 1390        1400        1410        1420        1430        1440
          *           *           *           *           *           *
GCATCATCAACACCAGACCATCCAATGATAGATCTGCTGAACTTTCTTCCCATGAACTTT 1450        1460        1470        1480        1490        1500
          *           *           *           *           *           *
GAGGCCATTGATTCCTATTCCAGCATGCTAAAAGCCTCCTGTCCATCTTCCTCACATCGT 1510        1520        1530        1540        1550        1560
          *           *           *           *           *           *
CCTAATAGGGATGCGGAATCCCCCAATACATCATTCTTATGTGGTCCCAATACAGATGTG 1570        1580        1590        1600        1610        1620
          *           *           *           *           *           *
TACTCCTTCTATTCATCATCCTCACGTATTCCCAAGATGGATGAGATATTGAAGAGGTTT 1630        1640        1650        1660        1670        1680
          *           *           *           *           *           *
CATGAATATATTCTTGTCAATCTGCTACGGAAGGATGAAACCAATTTGACATTTACTATT
```

FIG. 9B

```
      1690        1700        1710        1720        1730        1740
        *           *           *           *           *           *
GCAGATGAGGTCAAAAAGTTTTATGAAGGGTTGTTGCTCATGGTTACATATCTTATTGAA 1750        1760        1770        1780        1790        1800
        *           *           *           *           *           *
CCTCCAGTTCCTCACACTGAATGCAGGAAGCAAAATGATCTCTCAATGCGACATGAAGCT 1810        1820        1830        1840        1850        1860
        *           *           *           *           *           *
GTTGCAATTGAGGCGGAATCTGCTGTGTGTTTACATTATGAGGATAATATGAATAACAAC 1870        1880        1890        1900        1910        1920
        *           *           *           *           *           *
AGTAGGGAGATCAATCAGGTACTTCAGTTTTTGACTGTGACTTTCTGGCTTATCAAGTCT 1930        1940        1950        1960        1970        1980
        *           *           *           *           *           *
GAGGGTAACTTGATGGATCTACTGAAGCACAAATCCACTTTGGGAAATCAAGTTCTAGAT 1990        2000        2010        2020        2030        2040
        *           *           *           *           *           *
CTGATTGAGAGTGCTCATGAAGAGCTTATTCTCCTTAGATCTATTCTCATGGATCTTCTT 2050        2060        2070        2080        2090        2100
        *           *           *           *           *           *
AGGAAAAAGCTTTACAGATTGGATGATCTCTTAATGCATGCTGAGGTGACTGCAAAAAGG 2110        2120        2130        2140        2150        2160
        *           *           *           *           *           *
TTAGCAATATTCAGTGGTTCTTGTTATGAATATTTCATGAACGGAAGCAGCACTGAGAAA 2170        2180        2190        2200        2210        2220
        *           *           *           *           *           *
ATGAGGCCCTTGTTATCTGATTTTCTGCAAGAGATTGAGTCTGTCAAGGTAGAGTTCAGA 2230        2240        2250        2260        2270        2280
        *           *           *           *           *           *
AATGTTTGCTTGCAAGTTCTGGATATATCACCTTTTTCCCTGACAGATGGAGAAGGCCTT 2290        2300        2310        2320        2330        2340
        *           *           *           *           *           *
GTTAATTTCTTATTAAAAAACCAGGCCAAGGTGCCGAATGATGATGCTGTTTCTTCTGAT 2350        2360        2370        2380        2390        2400
        *           *           *           *           *           *
GGAAGTTTAGAGGATGCAAGCAGCACTGAGAAAATGGGACTTCCATCTGATTTTCTCCGA 2410        2420        2430        2440        2450        2460
        *           *           *           *           *           *
GAGATTGAGTCTGTTGAGATAAAGGAGGCCAGAAAATTATATGATCAAGTTTTGGATGCA 2470        2480        2490        2500        2510        2520
        *           *           *           *           *           *
ACACATTGTGAGACGAGTAAGACAGATGGAAAAAGCTTTATCAACATTATGTTAACCCAA
```

FIG. 9C

```
         2530        2540        2550        2560        2570        2580
           *           *           *           *           *           *
    CAGGACAAGTTGCCGGACTATGATGCTGGTTCAGTCTCTTATCTTCTTAACCAAATATCA 2590        2600        2610        2620        2630        2640
           *           *           *           *           *           *
    GTAGTTAAAGACAAATTATTGCACATTGGCTCTTTACTTGTAGATATTGTACAGTACCGG 2650        2660        2670        2680        2690        2700
           *           *           *           *           *           *
    AATATGCATATAGAACTTACAGATCTCGCTGAACGTGTTCAAGATAAAAACTACATTTGT 2710        2720        2730        2740        2750        2760
           *           *           *           *           *           *
    TTCTTCTGTCAAGGGTTATATTCCTGCTTGGTATTACACTATATCTCTCTGATGTC 2770        2780        2790        2800        2810        2820
           *           *           *           *           *           *
    AAGCAATTGCTTAAGTTTGTTGAGGCAGAGGTAAAGATTATTTGTCTGAAAGTACCAGAT 2830        2840        2850        2860        2870        2880
           *           *           *           *           *           *
    TCTTCAAGTTATAGCTTCCCTAAGACAAATGGATTAGGATATCTCAATTGCTTTTTAGGC 2890        2900        2910        2920        2930        2940
           *           *           *           *           *           *
    AAATTGGAGGAGCTTTTACGTTCTAAGCTCGATTTGATAATCGACTTAAAACATCAGATT 2950        2960        2970        2980        2990        3000
           *           *           *           *           *           *
    GAATCAGTCAAGGAGGGCTTATTGTGCCTAAGATCATTCATTGATCATTTTCAGAAAGC 3010        3020        3030        3040        3050        3060
           *           *           *           *           *           *
    TATGATGAGCATGATGAAGCTTGTGGTCTTATAGCAAGAGTTTCTGTAATGGCATACAAG 3070        3080        3090        3100        3110        3120
           *           *           *           *           *           *
    GCTGAGTATGTCATTGACTCATGCTTGGCCTATTCTCATCCACTCTGGTACAAAGTTCTT 3130        3140        3150        3160        3170        3180
           *           *           *           *           *           *
    TGGATTTCTGAAGTTCTTGAGAATATTAAGCTTGTAAATAAAGTTGTTGGTGAGACATGT 3190        3200        3210        3220        3230        3240
           *           *           *           *           *           *
    GAAAGAAGGAACATTGAAGTTACTGTGCATGAAGTTGCAAAGACTACCACTTATGTAGCA 3250        3260        3270        3280        3290        3300
           *           *           *           *           *           *
    CCATCTTTTTCAGCTTATACTCAAAGAGCAAACGAAGAAATGGAGGGTTTTCAGGATACA 3310        3320        3330        3340        3350        3360
           *           *           *           *           *           *
    ATAGATGAATTAAAGGATAAACTACTTGGAGGATCACCTGAGCTTGATGTCATCTCAATC
```

FIG. 9D

```
       3370       3380       3390       3400       3410       3420
         *          *          *          *          *          *
GTTGGCATGCCAGGATTGGGCAAGACTACACTAGCAAAGAAGATTTACAATGATCCAGAA 3430       3440       3450       3460       3470       3480
         *          *          *          *          *          *
GTCACCTCTCGCTTCGATGTCCATGCTCAATGTTGTGACTCAATTATATTCATGGAGA 3490       3500       3510       3520       3530       3540
         *          *          *          *          *          *
GAGTTGTTGCTCACCATTTTGAATGATGTCCTTGAGCCTTCTGATCGCAATGAAAAGAA 3550       3560       3570       3580       3590       3600
         *          *          *          *          *          *
GATGGTGAAATAGCTGATGAGTTACGCCGATTTTTGTTGACCAAGAGATTCTTGATTCTC 3610       3620       3630       3640       3650       3660
         *          *          *          *          *          *
ATTGATGATGTGTGGACTATAAAGTGTGGACAATCTATGTATGTGCTTCAGTGATGTT 3670       3680       3690       3700       3710       3720
         *          *          *          *          *          *
TCAAATAGGAGTAGAATTATCCTAACAACCCGCTTGAATGATGTCGCCGAATATGTCAAA 3730       3740       3750       3760       3770       3780
         *          *          *          *          *          *
TGTGAAAGTGATCCCCATCATCTTCGTTTATTCAGAGATGACGAGAGTTGGACATTATTA 3790       3800       3810       3820       3830       3840
         *          *          *          *          *          *
CAGAAAGAAGTCTTTCAAGGAGAGAGCTGTCCACCTGAACTTGAAGATGTGGGATTTGAA 3850       3860       3870       3880       3890       3900
         *          *          *          *          *          *
ATATCAAAAAGTTGTAGAGGGTTGCCTCTCTCAGTTGTGTTAGTAGCTGGTGTTCTGAAA 3910       3920       3930       3940       3950       3960
         *          *          *          *          *          *
CAGAAAAAGAAGACACTAGATTCATGGAAAGTAGTAGAACAAAGTCTAAGTTCCCAGAGG 3970       3980       3990       4000       4010       4020
         *          *          *          *          *          *
ATTGGCAGCTTGGAAGAGAGCATATCTATAATTGGATTCAGTTACAAGAATTTACCACAC 4030       4040       4050       4060       4070       4080
         *          *          *          *          *          *
TATCTTAAGCCTTGTTTTCTCTATTTTGGAGGATTTTTGCAGGGAAAGGATATTCATGTC 4090       4100       4110       4120       4130       4140
         *          *          *          *          *          *
TCAAAAATGACCAAGTTGTGGGTAGCTGAAGGGTTTGTACAAGCAAACAACGAAAAAGGA 4150       4160       4170       4180       4190       4200
         *          *          *          *          *          *
CAAGAAGATACCGCACAAGGTTTCTTGGACGATCTTATTGGTAGGAATGTAGTGATGGCC
```

FIG. 9E

```
        4210        4220        4230        4240        4250        4260
          *           *           *           *           *           *
ATGGAGAAGAGACCTAATACCAAGGTGAAAACGTGCCGCATTCATGATTTGTTGCATAAA 4270        4280        4290        4300        4310        4320
          *           *           *           *           *           *
TTCTGCATGGAAAAGGCCAAACAAGAGGATTTTCTTCTCCAAATCAATAGTGGAGAAGGT 4330        4340        4350        4360        4370        4380
          *           *           *           *           *           *
GTATTTCCTGAACGATTGGAGGAATACCGATTGTTCGTTCATTCTTACCAAGATGAAATT 4390        4400        4410        4420        4430        4440
          *           *           *           *           *           *
GATCTGTGGCGCCCATCTCGCTCTAATGTCCGATCTTTACTATTCAATGCAATTGATCCA 4450        4460        4470        4480        4490        4500
          *           *           *           *           *           *
GATAACTTGTTATGGCCGCGTGATATCTCCTTCATTTTGAGAGCTTCAAGCTTGTTAAA 4510        4520        4530        4540        4550        4560
          *           *           *           *           *           *
GTGTTGGATTTGGAATCATTCAACATTGGTGGTACTTTTCCCACTGAAATACAATATCTA 4570        4580        4590        4600        4610        4620
          *           *           *           *           *           *
ATTCAGATGAAGTACTTTGCGGCCCAAACTGATGCAAATTCAATTCCTTCATCTATAGCT 4630        4640        4650        4660        4670        4680
          *           *           *           *           *           *
AAGCTTGAAAATCTTGAGACTTTTGTCGTAAGAGGATTGGGAGGAGAGATGATATTACCT 4690        4700        4710        4720        4730        4740
          *           *           *           *           *           *
TGTTCACTTCTGAAGATGGTGAAATTGAGGCATATACATGTAAATGATCGGGTTTCTTTT 4750        4760        4770        4780        4790        4800
          *           *           *           *           *           *
GGTTTGCATGAGAACATGGATGTTTTAACTGGTAACTCACAATTACCTAATTTGGAAACC 4810        4820        4830        4840        4850        4860
          *           *           *           *           *           *
TTTTCTACTCCACGTCTCTTTTATGGTAAAGACGCAGAGAAGGTTTTGAGGAAGATGCCA 4870        4880        4890        4900        4910        4920
          *           *           *           *           *           *
AAATTGAGAAAATTGAGTTGCATATTTTCAGGGACATTTGGTTATTCAAGGAAATTGAAG 4930        4940        4950        4960        4970        4980
          *           *           *           *           *           *
GGTAGGTGTGTTCGTTTTCCCAGATTAGATTTTCTAAGTCACCTTGAGTCCCTCAAGCTG 4990        5000        5010        5020        5030        5040
          *           *           *           *           *           *
GTTTCGAACAGCTATCCAGCCAAACTTCCTCACAAGTTCAATTTCCCCTCGCAACTAAGG
```

FIG. 9F

```
       5050        5060        5070        5080        5090        5100
         *           *           *           *           *           *
GAACTGACTTTATCAAAGTTCCGTCTACCTTGGACCCAAATTTCGATCATTGCAGAACTG 5110        5120        5130        5140        5150        5160
         *           *           *           *           *           *
CCCAACTTGGTAATTCTTAAGTTATTGCTCAGAGCCTTTGAAGGGGATCACTGGGAAGTG 5170        5180        5190        5200        5210        5220
         *           *           *           *           *           *
AAAGATTCAGAGTTCCTAGAACTCAAATACTTAAAACTGGACAACCTCAAAGTTGTACAA 5230        5240        5250        5260        5270        5280
         *           *           *           *           *           *
TGGTCCATCTCTGATGATGCTTTTCCTAAGCTTGAACATTTGGTTTTAACGAAATGTAAG 5290        5300        5310        5320        5330        5340
         *           *           *           *           *           *
CATCTTGAGAAAATCCCTTCTCGTTTTGAAGATGCTGTTTGCCTAAATAGAGTTGAGGTG 5350        5360        5370        5380        5390        5400
         *           *           *           *           *           *
AACTGGTGCAACTGGAATGTTGCCAATTCAGCCCAAGATATTCAAACTATGCAACATGAA 5410        5420        5430        5440        5450        5460
         *           *           *           *           *           *
GTTATAGCAAATGATTCATTCACAGTTACTATACAGCCTCCAGATTGGTCTAAAGAACAG

5470
         *
CCCCTTGACTCTTAG
```

FIG. 9G

```
         10        20        30        40        50        60
          *         *         *         *         *         *
AATATTATAACTGTTGGAAAATGAACTCAACCATTCATCAATTATCTCAAGAAGAAGACC 70        80        90       100       110       120
          *         *         *         *         *         *
AGTATGAACTCTAAGCTTATGGGTAAGTAATTTCTCTCTGATTTTCATAAAATGAAAGAA 130       140       150       160       170       180
          *         *         *         *         *         *
GAAATTGCAAGTATTTACCTTCATTTGCTTTGTTAATTGCAGGCAGCTAGGACTTAAAAA 190       200       210       220       230       240
          *         *         *         *         *         *
AAAATCATTGAAGAAAGAGTTTTCTGTTAGATTTCAACCATCAAACACTAAACGAAAAG 250       260       270       280       290       300
          *         *         *         *         *         *
TAGTAAGTTGTTTATTTTCCTCTCATTTACTCAATATTCTTAACTATAAACTAATTGC 310       320       330       340       350       360
          *         *         *         *         *         *
ATCTTATAACACAGATCTGCATCCGTTTTTGTTTTTAAATTTTGAGAAAATGGTTAAAGC 370       380       390       400       410       420
          *         *         *         *         *         *
CCCCTCCAATTACAAGCTCGTACTTCACGGGTGTCCTATCACTTTCCTGAACTGTTTAAT 430       440       450       460       470       480
          *         *         *         *         *         *
GCAAGAATTATTACACTCCTAAAACGTCATAACCACATCTATGCTAATGAGTGAGACTCA 490       500       510       520       530       540
          *         *         *         *         *         *
CTCTTTGCAGAAATTTTATTTAAAACTTTTTTTAATTCATTTTCCTTTTTGATTTATTAT 550       560       570       580       590       600
          *         *         *         *         *         *
TTAAAAACAATTTAATATCAAAAGTTAAAGTTTATGAATGTATTTGTATCTTCAATT 610       620       630       640       650       660
          *         *         *         *         *         *
TGAAACATATTGTTGATAACATAGATGGTTGTTAATTATTTGAAGTTGAATATATTGAAT 670       680       690       700       710       720
          *         *         *         *         *         *
TTATGAATGTGATATTCAAATTAAAGAGACGCCCGAAATTTTATGGAAATCGATAAGCTT 730       740       750       760       770       780
          *         *         *         *         *         *
GAAATAACAATTTGACTTGCCACAAATGACCACCATTTTGAGTGGGTAATATATCAAAAA 790       800       810       820       830       840
          *         *         *         *         *         *
GTTGGAAACACTGAGAGAAGCTTATATCTAAAATTTAAGGAAATCTGGAGATGATTTAGG
```

FIG. 10A

```
       850         860         870         880         890         900
        *           *           *           *           *           *
GTGGTTTTGCATCAAATTTCAAAGCAATGGAATGAAGAAGATGAAGAACATAAACTAACT 910         920         930         940         950         960
        *           *           *           *           *           *
TTTCAGATGCGTAGGAAAAGGAAAAGTTATTAAAATTAGTCATGGATTTGTTGGGTATTA 970         980         990        1000        1010        1020
        *           *           *           *           *           *
AATATAAGATAAAAATTTATCTTAATATTCAAAGTTTATTGAAGAAAATCATTTGGGTGT 1030        1040        1050        1060        1070        1080
        *           *           *           *           *           *
TCATATATTTTTTAAAAAAAAATTGGTGCATATATCAAAGATTTTTATATACAGTTCT 1090        1100        1110        1120        1130        1140
        *           *           *           *           *           *
TGATTTTGGAGAGTAATGGATGAAATTGCTATAAATAATTTTGGTGTATCAATTAAAGTA 1150        1160        1170        1180        1190        1200
        *           *           *           *           *           *
GTGATAGGAATGATTTCAAGATGGTGAAGAACTTTGGTGGTGCCATATTTATGTTGTGAA 1210        1220        1230        1240        1250        1260
        *           *           *           *           *           *
GTTGAAAGAAAATTAATAACTAAAAATACACATTTATTATTTGTGTTGGTTCAAACTCTA 1270        1280        1290        1300        1310        1320
        *           *           *           *           *           *
TTACCGAGAGTGAGATACACTCACTATACCACAATGTGCCACGTAAGCGTCTAGGGAGTA 1330        1340        1350        1360        1370        1380
        *           *           *           *           *           *
AATTATTTTTAGTTTTAAATAATTCAGGGAGTGATAGGACATCCGTGAAGTTGAAGTATG 1390        1400        1410        1420        1430        1440
        *           *           *           *           *           *
TAGTTGAGATTTCGGGTATAGATTGGGGGGCTTTAGACCATTGGATTTGATCTAAGTATC 1450        1460        1470        1480        1490        1500
        *           *           *           *           *           *
TATTTCAATTTATATGATGTAATTTGACTTGACACGAAATTTAAGACGAAGAAAAAAGA 1510        1520        1530        1540        1550        1560
        *           *           *           *           *           *
CTAAGTACTTCCACTGTCAAACAATATTTGTCCACTACTATTTACACAATTAGTAAGAA 1570        1580        1590        1600        1610        1620
        *           *           *           *           *           *
ACTATACCCTTTGAATTTAATAAATACAATCTCTTGAAAAATGTAATAGTGAAATGACTA 1630        1640        1650        1660        1670        1680
        *           *           *           *           *           *
TAATTAATGATAAAAGTACATCAGGAACTAAGTGTAAAATTATCAATTCATTTTATAAAG
```

FIG. 10B

```
1690       1700       1710       1720       1730       1740
  *          *          *          *          *          *
TAGACAAGTATTGTTGGACATCCTAAAATAGTATAGTTGACAACTATTATTGAATAGAGG 1750       1760       1770       1780       1790       1800
  *          *          *          *          *          *
GAGTATCTCTGTGTGACTATACATTTTTTAAAATTAAAATTACTAAATATAGAGAATTA 1810       1820       1830       1840       1850       1860
  *          *          *          *          *          *
AAAATGTGTTATTTCCCCCTTTTTAGAATGATTAAAAAGAAATCCGAGTCTTATTTTAGA 1870       1880       1890       1900       1910       1920
  *          *          *          *          *          *
GAGATTTAAATTGTTTCACTAAATTTTTATCAAGTTAAAAATGCTTATTTTAGAGAGTTG 1930       1940       1950       1960       1970       1980
  *          *          *          *          *          *
AGTTATTTGGCCATGTTTTAGAAAAAAAAGTGATTGTGAGTATTGAGAGAAACTATTT 1990       2000       2010       2020       2030       2040
  *          *          *          *          *          *
TTCAATAGTTACAAAAAAATTTGGTTTAGTTTTTACTGTGTTTTTCCTCCATGGTTTCCA 2050       2060       2070       2080       2090       2100
  *          *          *          *          *          *
ACACTTGACTCTAGGCTTCTGTGCTATTTCGAAGCACTCTATAGTCTGTATCAGGGGCGG 2110       2120       2130       2140       2150       2160
  *          *          *          *          *          *
AGCCAGCTTGAATCCCTTCGGCGAAAAATATAACTATTTCTATATCGTAAAAATTATTCT 2170       2180       2190       2200       2210       2220
  *          *          *          *          *          *
TTATGTATTTATAGTAGATATTTAACCCCCCTCGGTTAGTCCGTGTGTTTAGTTCTTCAG 2230       2240       2250       2260       2270       2280
  *          *          *          *          *          *
ATTTTGAACCCCCCTAAATCCGCCACTGGTCTATACGCTTGATGTCAACTTGGTAACCTC 2290       2300       2310       2320       2330       2340
  *          *          *          *          *          *
CATTATCAAAGGTGTCTTCTTGAACTAAGATAACCAATGCTTCAAAGTGAAGATCACATA 2350       2360       2370       2380       2390       2400
  *          *          *          *          *          *
TTACACCATTGATTATATGATCATTAGGTGAAACTAAGCCACCCCGATTTCTAGATTTT 2410       2420       2430       2440       2450       2460
  *          *          *          *          *          *
GATACATTCCCTCAAGCACAAAGACACACACAATCATGCATAAGAAGAAAATAGTAGTGA 2470       2480       2490       2500       2510       2520
  *          *          *          *          *          *
AAAGTTCATGATTACATTTATGCCCGATACTTCTATAACCTACTGCAAATTATACACTTT
```

FIG. 10C

```
      2530        2540        2550        2560        2570        2580
        *           *           *           *           *           *
TATGGTATAGGCTATAGCCAAGTATCATGATAAACAACAAATACTGAAGTTCGCAACAAC 2590        2600        2610        2620        2630        2640
        *           *           *           *           *           *
CACAATAAGTTGGTTAGGAGGAAGATAATAATCACTAAGACTATAACTGTCGTCGAACTT 2650        2660        2670        2680        2690        2700
        *           *           *           *           *           *
CCAAATGTAAGCAACTTTATGATAAGCTAGTCATCACAACATTCAATAAAGATCAATATC 2710        2720        2730        2740        2750        2760
        *           *           *           *           *           *
CCAAGAGAGTTAGTATGCAATTGGATTAGAAGACGAACAGTATCTGATAAAATAAAGGAG 2770        2780        2790        2800        2810        2820
        *           *           *           *           *           *
CCTATAAATTCAAAAGACAATGCTTGTATGCTCATATTATCCCTATTACCTTTTGCGCT 2830        2840        2850        2860        2870        2880
        *           *           *           *           *           *
AAAACACACTTCCAACTCAAGTTGTTGGATATAATTCATTTGCAAGATTCACAAGAAAT 2890        2900        2910        2920        2930        2940
        *           *           *           *           *           *
GTCAATTTTGAGCTACCAAACTAGTCCATCATCTCGTTGGTTATCTTCCATTTATCAAAC 2950        2960        2970        2980        2990        3000
        *           *           *           *           *           *
AAAGAATCACATCCCCCGGATCAAATACAAATCAAACCCCAAACATCTCTAAGAGCTCCA 3010        3020        3030        3040        3050        3060
        *           *           *           *           *           *
ACAATCACTTCACATAGCATCTCAAATGGCAAGTTTTAAGAATAAACACAAGTCATCACA 3070        3080        3090        3100        3110        3120
        *           *           *           *           *           *
TAGTTGCTGCAACAAGTCTTAAGATCGAGGGACTTAACCTTCATAGCTTTAGAAAGCTCA 3130        3140        3150        3160        3170        3180
        *           *           *           *           *           *
AGCATAAGTGTCAACCATTCATACAATACAATCTTGAACGTAGAATATATTAAATAGTAA 3190        3200        3210        3220        3230        3240
        *           *           *           *           *           *
ATCCTAATGTATCCCAAGATAGTGCCTCCAAACTTCTTACTTCCTTGTAGTCTTTCCTGT 3250        3260        3270        3280        3290        3300
        *           *           *           *           *           *
GATGAACCTTGATAATGAGTCTGTAAGTTTTGGTTCCAAAACTGTACGTTCTTATTCATC 3310        3320        3330        3340        3350        3360
        *           *           *           *           *           *
TGTAGTGGTACAAATTTATAGTAGAGAGATATAAACTAGCAATCAGATTTCCTTAATTCA
```

FIG. 10D

```
                    3370        3380        3390        3400        3410        3420
                      *           *           *           *           *           *
        AGGAGATTTGAGCATCAAGGGAAGCTCTAATTTCCTAAACTATTTGATAGCATATTAAAG 3430        3440        3450        3460        3470        3480
                      *           *           *           *           *           *
        CTAATTTGTCAGATCTATTTATATCCTATAAAATCAGATCTGATCCTAGCCAGATATTT 3490        3500        3510        3520        3530        3540
                      *           *           *           *           *           *
        ACAAATCAACACTCCCCTTCAAGTTGACATGTAAGTATTTATCATGCCTAACTTGCTTAC 3550        3560        3570        3580        3590        3600
                      *           *           *           *           *           *
        AAGAATTTCACATTTTGGTTCAAACAAGCCTTTTATGAAAATATCCACAATTTGCTGGTC 3610        3620        3630        3640        3650        3660
                      *           *           *           *           *           *
        TGTTGGGACGAAAGACATACACACTTCATTTTTCAATCTTCGTTTTTATGAAGTTTCT 3670        3680        3690        3700        3710        3720
                      *           *           *           *           *           *
        ATCATGTTGAACTGGATTGGGAACAATACTTATGGCGGCTTTGTTGTCACATTACAACTT 3730        3740        3750        3760        3770        3780
                      *           *           *           *           *           *
        TATTGGTAGAGAAAATTTTCAGTCCATCTTCTTGAGCCAGTTCATTTCGTAGATCTGTAT 3790        3800        3810        3820        3830        3840
                      *           *           *           *           *           *
        TCAACTTTAGCAATGCTACAAGCGACATTCGGACGATACTGATTCATTACTTGCAGGATT 3850        3860        3870        3880        3890        3900
                      *           *           *           *           *           *
        TATTAACAATCACAGGAAACTTAAAAGGTGGAAGGGAGATGGCCAAGGAGTGTCGCGATG 3910        3920        3930        3940        3950        3960
                      *           *           *           *           *           *
        CAATAGGTACTATAAACCTTGTGAAGGGCCAGCATTTAGACAGAAGGACCACTAATCAAT 3970        3980        3990        4000        4010        4020
                      *           *           *           *           *           *
        TGGAGGATGCTATAAAGCACCTAACACATGTTGCTGTATTTCTCACAAATCTGGAGAAGC 4030        4040        4050        4060        4070        4080
                      *           *           *           *           *           *
        GTCACCCTGCTAATGGAATATCTATACATCTTAGGCCTCTATTTTTAGAAGCTCATGATG 4090        4100        4110        4120        4130        4140
                      *           *           *           *           *           *
        GCTTTTCTCTGATGTGTTCTCATCCTCCTCGTTCTCAGTTTACCGTTAAACTGGATAACA 4150        4160        4170        4180        4190        4200
                      *           *           *           *           *           *
        TTGCTGAGAAATTCAAATCTTCAAAGGCGTCAAGATCAACAAGGCAAGTGATCCCAGAGC
```

FIG. 10E

```
       4210        4220        4230        4240        4250        4260
          *           *           *           *           *           *
TGCTGCAAATAATTGAACCCGAGAATATTGCTAAGCGAATCAAAGCTTCAAAGCCATCAA 4270        4280        4290        4300        4310        4320
          *           *           *           *           *           *
GATCATCTAGCCCAATCACTGTGGATATGGTGGGGTTTATCGAATCCTTGCTTGGTTCTG 4330        4340        4350        4360        4370        4380
          *           *           *           *           *           *
TTCATCGTGCATTGTTCTTTATCAGTGCAGGGCCTCCTGTGTCTATGCTTGACAAGAAGC 4390        4400        4410        4420        4430        4440
          *           *           *           *           *           *
TTCGACATCTACAAGTCTTCTTTAGACTAATTTCAAAGCGGGGCATTGAGCATGAGAGTA 4450        4460        4470        4480        4490        4500
          *           *           *           *           *           *
TGAAGGATCTCTTCTACCATGTTGAGGATGTAGCTTACACTGCAGCACAACTATGTGTCT 4510        4520        4530        4540        4550        4560
          *           *           *           *           *           *
TGGGGTCGAGCTGCCATATGGATGACGAGTTCTCTAAATTTCTGGAAAGGATAAGTCGTC 4570        4580        4590        4600        4610        4620
          *           *           *           *           *           *
CTTTTAGCCCAGGATTGAGGCAGGTTTATCTCAATGCCTTGATAGGGTTAAATTCATCAA 4630        4640        4650        4660        4670        4680
          *           *           *           *           *           *
GATCAAAGACTACAATGAATGCCAAATATATGCTTGATTTTGTTAGTGCTCTCCAAGATG 4690        4700        4710        4720        4730        4740
          *           *           *           *           *           *
ATCTGAGACTAAGATGTGATAATCGAATTCGATGGCTCCAACGAGGACTTTCTTACCTTT 4750        4760        4770        4780        4790        4800
          *           *           *           *           *           *
GTCGATTCCTCAGGGACATAGAATCTTATCCTGTTTCACATCGACAACTGATTTCTCTTC 4810        4820        4830        4840        4850        4860
          *           *           *           *           *           *
AATTGAATATGGAAGATCTGGCTATTGGGTCTGCAAATGCCATCTACTCCTATGATGAGG 4870        4880        4890        4900        4910        4920
          *           *           *           *           *           *
ATATGGATAAGACTAGTGAAATAGACCATGAGCTTTTTCATTTGCAAATGAAGTTTAATT 4930        4940        4950        4960        4970        4980
          *           *           *           *           *           *
ATGTTAAAGTAGAGGTTGATCTGATTCGTCTACAAAACATTCAAGGCACCATAATAGTTC 4990        5000        5010        5020        5030        5040
          *           *           *           *           *           *
CTATGAAAGATCTGATTGACTATGTTTGGGAAGAGCTGATGTTCTTTAGAAGTTATTTCA
```

FIG. 10F

```
        5050         5060        5070       5080        5090       5100
          *            *           *          *           *          *
TGGATGCATTCGACCAGTTTAAAGAGCAGACCAGGATAACTGTTATTTTGAACTATATTC 5110         5120        5130       5140        5150       5160
          *            *           *          *           *          *
AGTCTGCAGTTAGTCAAGCATGGTCAGTCTGTGATTCTCTTTGTCATGACTTGAATCAAA 5170         5180        5190       5200        5210       5220
          *            *           *          *           *          *
ATGACTTGGCCAGGGAAATTAATTGCTTGCATTTTCAATTGCTTCTTAAGTTCAAGTTTA 5230         5240        5250       5260        5270       5280
          *            *           *          *           *          *
TCAAGGTCGCTATTAGACAGATGTGTCCCAGCATTTCTGCATCATCAACACCAGACCATC 5290         5300        5310       5320        5330       5340
          *            *           *          *           *          *
CAATGATAGATCTGCTGAACTTTCTTCCCATGAACTTTGAGGCCATTGATTCCTATTCCA 5350         5360        5370       5380        5390       5400
          *            *           *          *           *          *
GCATGCTAAAAGCCTCCTGTCCATCTTCCTCACATCGTCCTAATAGGGATGCGGAATCCC 5410         5420        5430       5440        5450       5460
          *            *           *          *           *          *
CCAATACATCATTCTTATGTGGTCCCAATACAGATGTGTACTCCTTCTATTCATCATCCT 5470         5480        5490       5500        5510       5520
          *            *           *          *           *          *
CACGTATTCCCAAGATGGATGAGATATTGAAGAGGTTTCATGAATATATTCTTGTCAATC 5530         5540        5550       5560        5570       5580
          *            *           *          *           *          *
GTCTACGGAAGGATGAAACCAATTTGACATTTACTATTGCAGATGAGGTCAAAAAGTTTT 5590         5600        5610       5620        5630       5640
          *            *           *          *           *          *
ATGATGGGTTGTTGCTCATGGTTACATATCTTATTGAACCTCCAGTTCCTCACACTGAAT 5650         5660        5670       5680        5690       5700
          *            *           *          *           *          *
GCAGGAAGCAAAATGATCTCTCAATGCGACATGAAGCTGTTGCAATTGAGGCGGAATCTG 5710         5720        5730       5740        5750       5760
          *            *           *          *           *          *
CTGTGTGTTTACATTATGAGGATAATATGAATAACAACAGTAGGGAGATCAATCAGGTAC 5770         5780        5790       5800        5810       5820
          *            *           *          *           *          *
TTCAGTTTTTGACTGTGACTTTCTGGCTTATCAAGTCTGAGGGTAACTTGATGGATCTAC 5830         5840        5850       5860        5870       5880
          *            *           *          *           *          *
TGAAGCACAAATCCACTTTGGGAAATCAAGTTCTAGATCTGATTGAGAGTGCTCATGAAG
```

FIG. 10G

```
      5890      5900      5910      5920      5930      5940
        *         *         *         *         *         *
AGCTTATTCTCCTTAGATCTATTCTCATGGATCTTCTTAGGAAAAAGCTTTACAGATTGG 5950      5960      5970      5980      5990      6000
        *         *         *         *         *         *
ATGATCTCTTAATGCATGCTGAGGTGACTGCAAAAAGGTTAGCAATATTCAGTGGTTCTT 6010      6020      6030      6040      6050      6060
        *         *         *         *         *         *
GTTATGAATATTTCATGAACGGAAGCAGCACTGAGAAAATGAGGCCCTTGTTATCTGATT 6070      6080      6090      6100      6110      6120
        *         *         *         *         *         *
TTCTGCAAGAGATTGAGTCTGTCAAGGTAGAGTTCAGAAATGTTTGCTTGCAAGTTCTGG 6130      6140      6150      6160      6170      6180
        *         *         *         *         *         *
ATATATCACCTTTTTCCCTGACAGATGGAGAAGGCCTTGTTAATTTCTTATTAAAAAACC 6190      6200      6210      6220      6230      6240
        *         *         *         *         *         *
AGGCCAAGGTGCCGAATGATGATGCTGTTTCTTCTGATGGAAGTTTAGAGGATGCAAGCA 6250      6260      6270      6280      6290      6300
        *         *         *         *         *         *
GCACTGAGAAAATGGGACTTCCATCTGATTTTCTCCGAGAGATTGAGTCTGTTGAGATAA 6310      6320      6330      6340      6350      6360
        *         *         *         *         *         *
AGGAGGCCAGAAAATTATATGATCAAGTTTTGGATGCAACACATTGTGAGACGAGTAAGA 6370      6380      6390      6400      6410      6420
        *         *         *         *         *         *
CAGATGGAAAAAGCTTTATCAACATTATGTTAACCCAACAGGACAAGTTGCCGGACTATG 6430      6440      6450      6460      6470      6480
        *         *         *         *         *         *
ATGCTGGTTCAGTCTCTTATCTTCTTAACCAAATATCAGTAGTTAAAGACAAACTATTGC 6490      6500      6510      6520      6530      6540
        *         *         *         *         *         *
ACATTGGCTCTTTACTTGTAGATATTGTACAGTACCGGAATATGCATATAGAACTTACAG 6550      6560      6570      6580      6590      6600
        *         *         *         *         *         *
ATCTCGCTGAACGTGTTCAAGATAAAAACTACATTTGTTTCTTCTCTGTCAAGGGTTATA 6610      6620      6630      6640      6650      6660
        *         *         *         *         *         *
TTCCTGCTTGGTATTACACACTATATCTCTCTGATGTCAAGCAATTGCTTAAGTTTGTTG 6670      6680      6690      6700      6710      6720
        *         *         *         *         *         *
AGGCAGAGGTAAAGATTATTTGTCTGAAAGTACCAGATTCTTCAAGTTATAGCTTCCCTA
```

FIG. 10H

```
      6730        6740        6750        6760        6770        6780
        *           *           *           *           *           *
AGACAAATGGATTAGGATATCTCAATTGCTTTTAGGCAAATTGGAGGAGCTTTTACGTT 6790        6800        6810        6820        6830        6840
        *           *           *           *           *           *
CTAAGCTCGATTTGATAATCGACTTAAAACATCAGATTGAATCAGTCAAGGAGGGCTTAT 6850        6860        6870        6880        6890        6900
        *           *           *           *           *           *
TGTGCCTAAGATCATTCATTGATCATTTTCAGAAAGCTATGATGAGCATGATGAAGCTT 6910        6920        6930        6940        6950        6960
        *           *           *           *           *           *
GTGGTCTTATAGCAAGAGTTTCTGTAATGGCATACAAGGCTGAGTATGTCATTGACTCAT 6970        6980        6990        7000        7010        7020
        *           *           *           *           *           *
GCTTGGCCTATTCTCATCCACTCTGGTACAAAGTTCTTTGGATTTCTGAAGTTCTTGAGA 7030        7040        7050        7060        7070        7080
        *           *           *           *           *           *
ATATTAAGCTTGTAAATAAAGTTGTTGGTGAGACATGTGAAAGAAGGAACATTGAAGTTA 7090        7100        7110        7120        7130        7140
        *           *           *           *           *           *
CTGTGCATGAAGTTGCAAAGACTACCACTTATGTAGCACCATCTTTTTCAGCTTATACTC 7150        7160        7170        7180        7190        7200
        *           *           *           *           *           *
AAAGAGCAAACGAAGAAATGGAGGGTTTTCAGGATACAATAGATGAATTAAAGGATAAAC 7210        7220        7230        7240        7250        7260
        *           *           *           *           *           *
TACTTGGAGGATCACCTGAGCTTGATGTCATCTCAATCGTTGGCATGCCAGGATTGGGCA 7270        7280        7290        7300        7310        7320
        *           *           *           *           *           *
AGACTACACTAGCAAAGAAGATTTACAATGATCCAGAAGTCACCTCTCGCTTCGATGTCC 7330        7340        7350        7360        7370        7380
        *           *           *           *           *           *
ATGCTCAATGTGTTGTGACTCAATTATATTCATGGAGAGAGTTGTTGCTCACCATTTTGA 7390        7400        7410        7420        7430        7440
        *           *           *           *           *           *
ATGATGTCCTTGAGCCTTCTGATCGCAATGAAAAGAAGATGGTGAAATAGCTGATGAGT 7450        7460        7470        7480        7490        7500
        *           *           *           *           *           *
TACGCCGATTTTTGTTGACCAAGAGATTCTTGATTCTCATTGATGATGTGTGGGACTATA 7510        7520        7530        7540        7550        7560
        *           *           *           *           *           *
AAGTGTGGGACAATCTATGTATGTGCTTCAGTGATGTTTCAAATAGGAGTAGAATTATCC
```

FIG. 10I

```
         7570      7580      7590      7600      7610      7620
           *         *         *         *         *         *
     TAACAACCCGCTTGAATGATGTCGCCGAATATGTCAAATGTGAAAGTGATCCCCATCATC 7630      7640      7650      7660      7670      7680
           *         *         *         *         *         *
     TTCGTTTATTCAGAGATGACGAGAGTTGGACATTATTACAGAAAGAAGTCTTTCAAGGAG 7690      7700      7710      7720      7730      7740
           *         *         *         *         *         *
     AGAGCTGTCCACCTGAACTTGAAGATGTGGGATTTGAAATATCAAAAGTTGTAGAGGGT 7750      7760      7770      7780      7790      7800
           *         *         *         *         *         *
     TGCCTCTCTCAGTTGTGTTAGTAGCTGGTGTTCTGAAACAGAAAAGAAGACACTAGATT 7810      7820      7830      7840      7850      7860
           *         *         *         *         *         *
     CATGGAAAGTAGTAGAACAAAGTCTAAGTTCCCAGAGGATTGGCAGCTTGGAAGAGAGCA 7870      7880      7890      7900      7910      7920
           *         *         *         *         *         *
     TATCTATAATTGGATTCAGTTACAAGAATTTACCACACTATCTTAAGCCTTGTTTTCTCT 7930      7940      7950      7960      7970      7980
           *         *         *         *         *         *
     ATTTTGGAGGATTTTTGCAGGGAAAGGATATTCATGTCTCAAAAATGACCAAGTTGTGGG 7990      8000      8010      8020      8030      8040
           *         *         *         *         *         *
     TAGCTGAAGGGTTTGTACAAGCAAACAACGAAAAGGACAAGAAGATACCGCACAAGGTT 8050      8060      8070      8080      8090      8100
           *         *         *         *         *         *
     TCTTGGACGATCTTATTGGTAGGAATGTAGTGATGGCCATGGAGAAGAGACCTAATACCA 8110      8120      8130      8140      8150      8160
           *         *         *         *         *         *
     AGGTGAAAACGTGCCGCATTCATGATTTGTTGCATAAATTCTGCATGGAAAAGGCCAAAC 8170      8180      8190      8200      8210      8220
           *         *         *         *         *         *
     AAGAGGATTTTCTTCTCCAAATCAATAGGTAAAAAAACTGTATTAATTTTACATTACCA 8230      8240      8250      8260      8270      8280
           *         *         *         *         *         *
     AAAAAAAGAACTGTATTAATTTTACTGTATTATGTTTATGCCAACTCTCATTTCCATGT 8290      8300      8310      8320      8330      8340
           *         *         *         *         *         *
     GTTCTCTTTTATCCAATTCAGTGGAGAAGGTGTATTTCCTGAACGATTGGAGGAATACCG 8350      8360      8370      8380      8390      8400
           *         *         *         *         *         *
     ATTGTTCGTTCATTCTTACCAAGATGAAATTGATCTGTGGCGCCCATCTCGCTCTAATGT
```

FIG. 10J

```
        8410       8420       8430       8440       8450       8460
          *          *          *          *          *          *
CCGATCTTTACTATTCAATGCAATTGATCCAGATAACTTGTTATGGCCGCGTGATATCTC 8470       8480       8490       8500       8510       8520
          *          *          *          *          *          *
CTTCATTTTTGAGAGCTTCAAGCTTGTTAAAGTGTTGGATTTGGAATCATTCAACATTGG 8530       8540       8550       8560       8570       8580
          *          *          *          *          *          *
TGGTACTTTTCCCACTGAAATACAATATCTAATTCAGATGAAGTACTTTGCGGCCCAAAC 8590       8600       8610       8620       8630       8640
          *          *          *          *          *          *
TGATGCAAATTCAATTCCTTCATCTATAGCTAAGCTTGAAAATCTTGAGACTTTTGTCGT 8650       8660       8670       8680       8690       8700
          *          *          *          *          *          *
AAGAGGATTGGGAGGAGAGATGATATTACCTTGTTCACTTCTGAAGATGGTGAAATTGAG 8710       8720       8730       8740       8750       8760
          *          *          *          *          *          *
GCATATACATGTAAATGATCGGGTTTCTTTTGGTTTGCATGAGAACATGGATGTTTTAAC 8770       8780       8790       8800       8810       8820
          *          *          *          *          *          *
TGGTAACTCACAATTACCTAATTTGGAAACCTTTTCTACTCCACGTCTCTTTTATGGTAA 8830       8840       8850       8860       8870       8880
          *          *          *          *          *          *
AGACGCAGAGAAGGTTTTGAGGAAGATGCCAAAATTGAGAAAATTGAGTTGCATATTTTC 8890       8900       8910       8920       8930       8940
          *          *          *          *          *          *
AGGGACATTTGGTTATTCAAGGAAATTGAAGGGTAGGTGTGTTCGTTTTCCCAGATTAGA 8950       8960       8970       8980       8990       9000
          *          *          *          *          *          *
TTTTCTAAGTCACCTTGAGTCCCTCAAGCTGGTTTCGAACAGCTATCCAGCCAAACTTCC 9010       9020       9030       9040       9050       9060
          *          *          *          *          *          *
TCACAAGTTCAATTTCCCCTCGCAACTAAGGGAACTGACTTTATCAAAGTTCCGTCTACC 9070       9080       9090       9100       9110       9120
          *          *          *          *          *          *
TTGGACCCAAATTTCGATCATTGCAGAACTGCCCAACTTGGTAATTCTTAAGTTATTGCT 9130       9140       9150       9160       9170       9180
          *          *          *          *          *          *
CAGAGCCTTTGAAGGGGATCACTGGGAAGTGAAAGATTCAGAGTTCCTAGAACTCAAATA 9190       9200       9210       9220       9230       9240
          *          *          *          *          *          *
CTTAAAACTGGACAACCTCAAAGTTGTACAATGGTCCATCTCTGATGATGCTTTTCCTAA
```

FIG. 10K

```
       9250        9260        9270        9280        9290        9300
         *           *           *           *           *           *
GCTTGAACATTTGGTTTTAACGAAATGTAAGCATCTTGAGAAAATCCCTTCTCGTTTTGA 9310        9320        9330        9340        9350        9360
         *           *           *           *           *           *
AGATGCTGTTTGCCTAAATAGAGTTGAGGTGAACTGGTGCAACTGGAATGTTGCCAATTC 9370        9380        9390        9400        9410        9420
         *           *           *           *           *           *
AGCCCAAGATATTCAAACTATGCAACATGAAGTTATAGCAAATGATTCATTCACAGTTAC 9430        9440        9450        9460        9470        9480
         *           *           *           *           *           *
TATACAGCCTCCAGATTGGTCTAAAGAACAGCCCCTTGACTCTTAGCAAAGGTTTGTTCT 9490        9500        9510        9520        9530        9540
         *           *           *           *           *           *
TGCTGTGTTCATCCAAGTACATTTAACATTTATTCATTTTGTTTTGCACCAGAACATGTT 9550        9560        9570        9580        9590        9600
         *           *           *           *           *           *
TGTTTTGCTAGTATTACTTGATACATTAAAAGAAATCGAACTCATATTTCTGCTACAGTC 9610        9620        9630        9640        9650        9660
         *           *           *           *           *           *
TTAACTTTTCTTGGGCTTACTCGAGGTCTAGATTAGATCAATGGTTCATGTAATTCTTAA 9670        9680        9690        9700        9710        9720
         *           *           *           *           *           *
TTCACTGTTTCATTCAACTGTCTTATCATAGTTGTGAAATGACAATATTGTTATCCCTAG 9730        9740        9750        9760        9770        9780
         *           *           *           *           *           *
CCAAATTTATTATGTTCAAATGAAAACTGATGTCACAACTACTTTTTTGTGAAATGTTTT 9790        9800        9810        9820        9830        9840
         *           *           *           *           *           *
TGAATTTTTTGCTATAAAATTGACGAATTGACAGGCTTCTATTTTTGTCAGCTAAACTCT 9850        9860        9870        9880        9890        9900
         *           *           *           *           *           *
TTGTCACCAGAGGTGTATTTAGAATTACTGTGGTTTTATGAAAGATTTTTATAGAATTTT 9910        9920        9930        9940        9950        9960
         *           *           *           *           *           *
ATGCTTTTGCAGAATCTTAAGTTTCTAGTTTAAAACAACAGCACTTTTCTGTTTCAGAGG 9970        9980        9990       10000       10010       10020
         *           *           *           *           *           *
TAGCAGCAGCTAAAGTTCAAGGCATTTTGTTTATTTCTAGAACAAGGGGAGTTCTTACGT 10030       10040       10050       10060       10070       10080
         *           *           *           *           *           *
TGAATTCTTGAAAAGAAGAAGAATCAGGAGCAGGTAAAGATTATCTCTTTTTCTGTTTTT
```

FIG. 10L

```
        10090      10100      10110      10120      10130      10140
          *          *          *          *          *          *
CTTCTTTTAGATGTTATTTCTTCATCTTGAACGTGAACACCGCTGAAAGCATTTTAATAA 10150      10160      10170      10180      10190      10200
          *          *          *          *          *          *
AACCGGAGAAATAAATAAGATCTTTTTATATAAAGCATTATCATGTAAATATGCCTAAAT 10210      10220      10230      10240      10250      10260
          *          *          *          *          *          *
CCATATGGTACAACTGTTTGACAAATGATAGAGAGGGAGACTGATGCAAGTTTTATAGT 10270      10280      10290      10300      10310      10320
          *          *          *          *          *          *
ATAAGTAAAACAGGATTGAGAAAAAAATCCTTGCACGATTTTCAATTTCTGGCCACATCA 10330      10340      10350      10360      10370      10380
          *          *          *          *          *          *
CAATGTGTGTCAAAGTTCCCCTCTTTAAGTGGAACAAGCAATCAGAAAAGCACATTCTTA 10390      10400      10410      10420      10430      10440
          *          *          *          *          *          *
TCGGTGACTTACCAATACCAGCTGACTGTCTCATCTTGGTTAACTTAGCCTTGCTTACTT 10450      10460      10470      10480      10490      10500
          *          *          *          *          *          *
AGACTATTAGATTAGTTACTAATGAGCTGGTAAATTGGAACCAAATGTAGTTAGCTTGAT 10510      10520      10530      10540      10550      10560
          *          *          *          *          *          *
GAGCTGGTAGATATGTATGTATGAAGATACACGCGTAACTTTAGTCAATGGTTAATTTTT 10570      10580      10590      10600      10610      10620
          *          *          *          *          *          *
CATTTTGTATTTTTTCTTCACAGAGTATATATGACGCGAGAATACTTGGCCTAAAAGTT 10630      10640      10650      10660      10670      10680
          *          *          *          *          *          *
TTTGCTTCACTAATTTAACTATTGCCGTGGATGAAACAAGCATGGCAACATTTTCAACAA 10690      10700      10710      10720      10730      10740
          *          *          *          *          *          *
CTATCACTCAAGCAATGTAAAAAAGGAGGTTCTACGAGTGGTACATGTAAGAGTTTTGT 10750      10760      10770      10780      10790      10800
          *          *          *          *          *          *
GCACACAAGAGGTTCTGAGACTTGAACCATCCATGTCCAAGGCAGTTCAGATGCTAGTAA 10810      10820      10830      10840      10850      10860
          *          *          *          *          *          *
AGAAAGAAGAAGATGAACCTGCACTAATTAATCCTCCCTTTATGAATAAGAGAATGAGAA 10870      10880      10890      10900      10910      10920
          *          *          *          *          *          *
AAGATGGAGCTTCATGAACCAAAAGTTACCTTTTTTTTTTTTAATGGCATTACTTTGAA
```

FIG. 10M

```
         10930      10940      10950      10960
           *          *          *          *
    GCACATGTTTGTTAGTTGTAAATTGTAATGGTGAAGTGTTTGTAAATA
```

FIG. 10N

```
MAKECRDAIGTINLVKGQHLDRRTTNQLEDAIKHLTHVAVFLTNLEKRHPANGISIHLRP      60
LFLEAHDGFSLMCSHPPRSQFTVKLDNIAEKFKSSKASRSTRQVIPELLQIIEPENIAKR     120
IKASKPSRSSSPITVDMVGFIESLLGSVHRALFFISAGPPVSMLDKKLRHLQVFFRLISK     180
RGIEHESMKDLFYHVEDVAYTAAQLCVLGSSCHMDDEFSKFLERISRPFSPGLRQVYLNA     240
LIGLNSSRSKTTMNAKYMLDFVSALQDDLRLRCDNRIRWLQRGLSYLCRFLRDIESYPVS     300
HRQLISLQLNMEDLAIGSANAIYSYDEDMDKTSEIDHELFHLQMKFNYVKVEVDLIRLQN     360
IQGTIIVPMKDLIDYVWEELMFFRSYFMDAFDQFKEQTRITVILNYIQSAVSQAWSVCDS     420
LCHDLNQNDLAREINCLHFQLLLKFKFIKVAIRQMCPSISASSTPDHPMIDLLNFLPMNF     480
EAIDSYSSMLKASCPSSSHRPNRDAESPNTSFLCGPNTDVYSFYSSSSRIPKMDEILKRF     540
HEYILVNLLRKDETNLTFTIADEVKKFYEGLLLMVTYLIEPPVPHTECRKQNDLSMRHEA     600
VAIEAESAVCLHYEDNMNNNSREINQVLQFLTVTFWLIKSEGNLMDLLKHKSTLGNQVLD     660
LIESAHEELILLRSILMDLLRKKLYRLDDLLMHAEVTAKRLAIFSGSCYEYFMNGSSTEK     720
MRPLLSDFLQEIESVKVEFRNVCLQVLDISPFSLTDGEGLVNFLLKNQAKVPNDDAVSSD     780
GSLEDASSTEKMGLPSDFLREIESVEIKEARKLYDQVLDATHCETSKTDGKSFINIMLTQ     840
QDKLPDYDAGSVSYLLNQISVVKDKLLHIGSLLVDIVQYRNMHIELTDLAERVQDKNYIC     900
FFSVKGYIPAWYYTLYLSDVKQLLKFVEAEVKIICLKVPDSSSYSFPKTNGLGYLNCFLG     960
KLEELLRSKLDLIIDLKHQIESVKEGLLCLRSFIDHFSESYDEHDEACGLIARVSVMAYK    1020
AEYVIDSCLAYSHPLWYKVLWISEVLENIKLVNKVVGETCERRNIEVTVHEVAKTTTYVA    1080
PSFSAYTQRANEEMEGFQDTIDELKDKLLGGSPELDVISIVGMPGLGKTTLAKKIYNDPE    1140
VTSRFDVHAQCVVTQLYSWRELLLTILNDVLEPSDRNEKEDGEIADELRRFLLTKRFLIL    1200
IDDVWDYKVWDNLCMCFSDVSNRSRIILTTRLNDVAEYVKCESDPHHLRLFRDDESWTLL    1260
QKEVFQGESCPPELEDVGFEISKSCRGLPLSVVLVAGVLKQKKKTLDSWKVVEQSLSSQR    1320
IGSLEESISIIGFSYKNLPHYLKPCFLYFGGFLQGKDIHVSKMTKLWVAEGFVQANNEKG    1380
QEDTAQGFLDDLIGRNVVMAMEKRPNTKVKTCRIHDLLHKFCMEKAKQEDFLLQINSGEG    1440
VFPERLEEYRLFVHSYQDEIDLWRPSRSNVRSLLFNAIDPDNLLWPRDISFIFESFKLVK    1500
VLDLESFNIGGTFPTEIQYLIQMKYFAAQTDANSIPSSIAKLENLETFVVRGLGGEMILP    1560
CSLLKMVKLRHIHVNDRVSFGLHENMDVLTGNSQLPNLETFSTPRLFYGKDAEKVLRKMP    1620
KLRKLSCIFSGTFGYSRKLKGRCVRFPRLDFLSHLESLKLVSNSYPAKLPHKFNFPSQLR    1680
ELTLSKFRLPWTQISIIAELPNLVILKLLLRAFEGDHWEVKDSEFLELKYLKLDNLKVVQ    1740
WSISDDAFPKLEHLVLTKCKHLEKIPSRFEDAVCLNRVEVNWCNWNVANSAQDIQTMQHE    1800
VIANDSFTVTIQPPDWSKEQPLDS
```

FIG. 11

```
1398   VMAMEKRPNTKVKTCRIHDLLHKF
1422   CMEKAKQEDFLLQINSGEGVFPER
1446   LEEYRLFVHSYQDEIDLWRPSRSN
1470   VRSL LFNAIDPDNLLWPRDISFI
1493   FESFKLVKVLDLESFNIGGTFPTE
1517   IQYLIQMKYFAAQTD ANSIPSS
1539   IAKLENLETFVVRGLGGEMILPCS
1563   LLKMVKLRHIHV
1575   NDRVSFGLHENMDVLTGNSQLPN
1598   LETFSTPRLFYGKDAEKVLRKMPK
1622   LRKLSCIFSGTFGYSRKLKGRCVRFPR
1649   LDFLSHLESLKLVSNSYPAKLPHK
1673   FNFPSQLRELTLSKFRLPWTQISI
1697   IAELPNLVILKLLLRAFEGDHWEVK
1722   DSEFLELKYLKDNLKVVQWSIS
1745   DDAFPKLEHLVLTKCKHLEKIPSR
1769   FEDAVCLNRVEVNWCNWN VANS
1791   AQDIQTMQHEVIANDSFTVTIQPP

CONS   LXXLXXLXXLXLXXN/CXXLXXIPSX
```

FIG. 12

716-786  SSTEKMRPLLLSDFLQEIESVKV.EFRNVCLQVLDI..SPFSLTDGEGLVNFLLKNQAKVPNDDAVSSDGSLEDA 787-858  SSTEKM.GLPSDFLREIESVEIKEARKLYDQVLDATHCETSKTDGKSFINIMLTQQDKLPDYDAGSVSYLLNQ.

FIG. 13

M tomato

Arabidopsis
pepper
tobacco
soybean
bean
maize
barley
oat

PRF PROTEIN AND NUCLEIC ACID SEQUENCES: COMPOSITIONS AND METHODS FOR PLANT PATHOGEN RESISTANCE

CROSS REFERENCE TO RELATED CASES

This application is a divisional of U.S. patent application Ser. No. 08/680,327, filed Jul. 11, 1996 now U.S. Pat. No. 5,859,351 now allowed, which is a continuation-in-part of U.S. patent application No. 08/310,912, filed Sep. 22, 1994, which is a continuation-in-part of U.S. patent application Ser. No. 08/227,360, filed Apr. 13, 1994, now abandoned, all of which are incorporated herein by reference.

ACKNOWLEDGMENT OF GOVERNMENT SUPPORT

This invention was made with Government support under a National Science Foundation (NSF) Cooperative Agreement BIR-8920216 to CEPRAP, a NSF Science and Technology Center. The Government has certain rights to this invention.

BACKGROUND OF THE INVENTION

This invention relates to plant disease resistance, in particular to plant genes conferring pathogen resistance.

Whether a plant is resistant or susceptible to attack by a given pathogen is frequently under the control of a single, dominant resistance gene (Flor, *Annu. Rev. Phytopathol.* 9:275–296, 1971). Resistance gene products are thought to recognize signal molecules produced by the pathogen and respond by initiating rapid changes in host cell physiology and metabolism that directly inhibit pathogen growth.

A well-studied model for interactions of plant pathogens with their hosts is that between tomato (*Lycopersicon esculentum*) and *Pseudomonas syringae* pv. *tomato* (Pst; Carland and Staskawicz, *Mol. Gen. Genet.* 239:17–27, 1993; Martin et al., *Mol. Plant-Microbe Interact.* 6:26–34, 1993). Two genes required for the tomato signaling pathway that leads to resistance to Pst strains that express the avirulence gene avrPto (Ronald et al., *J. Bacteriol.* 174:1604–1611, 1992; Salmeron and Staskawicz, *Mol. Gen. Genet.* 239:6–16, 1993) have been identified through analyses of naturally-occurring resistant and susceptible tomato lines (Pitblado and MacNeill, *Canad. J. Plant Pathol.* 5:251–255, 1983) and by mutational studies (Salmeron et al., *Plant Cell* 6:511–520, 1994).

The Pto gene (Pitblado and MacNeill, *Canad. J. Plant Pathol.* 5:251–255, 1983) encodes a serine/threonine protein kinase with a potential amino-terminal myristoylation site (Martin et al., *Science* 262:1432–1436, 1993) that lacks additional motifs such as a leucine-rich repeat. Pto is a member of a tightly clustered family of five genes located on the short arm of chromosome five. It encodes a protein highly similar to the cytoplasmic domain of the Brassica self-incompatability gene SRK and the mammalian signaling factor Raf (Martin et al., *Science* 262:1432–1436, 1993).

The identification of Pto as a protein kinase suggests that intracellular phosphorylation events are important in the response of tomato to pathogen strains expressing avrPto. The tomato Pti1 protein is a substrate for Pto (Zhou et al., *Cell* 83:925–935, 1995) and Pti1 itself is predicted to be a serine/threonine protein kinase (Zhou et al., *Cell* 83:925–935, 1995). Therefore, the pathway for defense against Pst may incorporate a protein kinase cascade similar to those employed in numerous other eukaryotic signaling pathways (Hunter, *Cell* 80:225–236, 1995).

The second gene required for resistance of tomato to Pst, designated Prf, was identified through a mutational approach and shown to be tightly linked to Pto (Salmeron et al., *Plant Cell* 6:511–520, 1994). Analysis of prf mutant alleles suggested that in addition to its role in disease resistance, the Prf protein also functions in the response of tomato to the organophosphate insecticide Fenthion (Salmeron et al., *Plant Cell* 6:511–520, 1994), a trait that co-segregates with Pto in genetic crosses (Carland and Staskawicz, *Mol. Gen. Genet.* 239:17–27, 1993). In sensitive tomato lines, Fenthion induces rapid necrosis that mimics the hypersensitive response observed after inoculation with Pst strains expressing avrPto (Laterrot and Philouze, *Tomato Genet. Research Coop. Newsletter* 35:6, 1985). This observation suggests that Fenthion mimics an elicitor produced under control of the avrPto gene in Pst.

Necrosis in response to Fenthion does not appear to require the Pto kinase (Martin et al., *Science* 262:1432–1436, 1993; Salmeron et al., *Plant Cell* 6:511–520, 1994), but rather is conferred by another member of the Pto gene cluster, designated Fen. Fen encodes a protein kinase 80% identical in amino acid sequence to Pto (Martin et al., *Plant Cell* 6:1543–1552, 1994; Rommens et al., *Plant Cell* 7:249–257, 1995). Thus, Prf is involved with two similar but distinct kinases, Pto and Fen, to induce hypersensitive-like necrosis in response to pathogen elicitor and Fenthion signals, respectively.

SUMMARY OF THE INVENTION

The tomato Prf genomic and cDNA sequences have been cloned and the corresponding DNA and amino acid sequences are provided herein. Expression of the Prf gene in transgenic plants confers resistance to Pst and, surprisingly, to a broad variety of unrelated pathogens. Also encompassed by the present invention are such transgenic plants. The tomato Prf gene hybridizes to homologous sequences from a variety of other plant species under moderately stringent hybridization conditions, and probes and primers based on the tomato Prf sequence can be used to isolate such Prf homologs. Based on these discoveries, the present invention provides compositions and methods related to the isolated tomato Prf gene.

For example, the present invention provides nucleic acid sequences that hybridize specifically to a native Prf sequence under at least moderately stringent conditions, preferably including at least 15 contiguous nucleotides of a native tomato Prf nucleic acid sequence. Such sequences are useful, for example, as probes and primers for isolating Prf homologs from other plant species. When expressed in transgenic plants (or plant cells or tissues), longer portions of the native Prf nucleic acid sequence, including all or a significant portion of the Prf coding region, confer pathogen resistance and/or Fenthion sensitivity.

The present invention also provides, for example, the native tomato Prf promoter sequence, which is useful, for example, for expressing a Prf gene or a heterologous gene in plant cells.

Also provided are sequences corresponding to various functional domains of the tomato Prf polypeptide, including, for example: (1) three motifs comprising the predicted ATP/GTP binding site, the "P-loop" domain occurring at residues 1120–1132, followed by the companion kinase domains 2 and 3a at 1195–1205 and 1224–1231, respectively; (2) sequences resembling leucine-rich repeat domains with approximately fourteen to eighteen imperfect copies of the leucine-rich repeat motif with a consensus sequence of LXXLXXLXXLXXLXLXXN/CXXLXXIPSX, beginning at residue 1398; (3) a leucine zipper spanning residues 959–994; (4) a block of residues from 716–858 that includes two copies of a direct repeat, with 49% amino acid identity between the two copies; and (5) a string of seven amino acids (1058–1064) that corresponds precisely to one half of the binding site for interleukin-8 in the mammalian interleukin-8 receptor.

Armed with the disclosed tomato Prf nucleotide and amino acid sequences and taking advantage of the degeneracy of the genetic code, it is possible to design nucleic acids that are similar to the tomato Prf gene and that encode functional Prf polypeptides. Preferably, such nucleic acids include only silent or conservative changes to the native tomato Prf gene sequence. The present invention therefore also provides isolated nucleic acids that include a sequence that encodes a polypeptide that is at least about 70% homologous to a native tomato Prf polypeptide and that has Prf activity. That is, when expressed in a transgenic plant (or plant cell or tissue), the nucleic acid encodes a polypeptide that confers pathogen resistance or Fenthion sensitivity.

The present invention also encompasses cells, tissues, or transgenic plants comprising such nucleic acids.

The present invention also provides isolated Prf polypeptides comprising the at least 10 consecutive amino acids of a native tomato Prf polypeptide. Such polypeptides are useful for a number of purposes, including raising Prf-specific antibodies that can be used to purify Prf polypeptides, in immunoassays, or for expression cloning efforts.

Also provided by the present invention are related methods of producing Prf polypeptides, methods of producing pathogen-resistant transgenic plants, and methods of obtaining Prf genes from various plant species (and Prf homologs obtained thereby).

The foregoing and other aspects of the invention will become more apparent from the following detailed description and accompanying drawings.

BRIEF DESCRIPTION OF THE SEQUENCES

SEQ ID NO: 1 shows the nucleotide and amino acid sequence of the genomic clone of tomato Prf.

SEQ ID NO: 2 shows the deduced amino acid sequence of tomato PRF protein

SEQ ID NO: 3 shows the nucleotide and amino acid sequence of the tomato Prf cDNA.

SEQ ID NO: 4 shows the primary structure of the Prf leucine-rich repeat, with consensus listed at bottom.

SEQ ID NO: 5 shows region of internal repetition within the amino-terminal half of the Prf protein.

SEQ ID NOs: 6–9 show oligonucleotide primers used to screen a copy of the Tanksley tomato YAC library for Prf coding sequences.

SEQ ID NOs: 10 and 11 show oligonucleotide primers used to in amplifying sequences to obtain a full-length Pfr cDNA.

SEQ ID NO: 12 is the T-Prime primer used for RACE analysis.

SEQ ID NOs: 13 and 14 are Prf-specific primers, also designated as PfrPX1 and PfrPX2.

SEQ ID NOs: 15 and 16 are Prf-specific primers, also designated as PrfPX1B and PrfPX2B.

SEQ ID NO: 17 is the leucine-rich repeat motif found in Prf (see also FIG. 12).

BRIEF DESCRIPTION OF THE DRAWINGS

FIG. 1 shows corresponding genetic and physical maps of the tomato genomic region containing the Prf, Pto and Fen genes. (A) Restriction fragment length polymorphism (RFLP) markers tightly linked to Pto and within a distance to which Prf had been genetically mapped relative to Pto. (B) YACs from which a contig of approximately 400 kb was constructed. The horizontal dotted line indicates that marker VC168S was obtained by homology to the left end of YAC VC5.C2. (C) Cosmid contig of the region containing Prf constructed from VC168.G12. The 5.3 kb EcoRI fragment (SOR2) spanning the 1.1 kb deletion in tomato mutant prf-3 is indicated. Cosmid SOR2-7 complemented the prf-3 mutation (+) when transformed into prf-3 tomatoes, whereas SOR1-3 did not (−). (D) EcoRI restriction map of YAC clone RG269.D3 from the Tanskley tomato YAC library showing the locations of Pto, Fen and Prf.

FIG. 2 shows a Southern blot of DNA from resistant tomato line 76R, susceptible line 76S, and susceptible line prf-3 that was restricted with EcoRI and hybridized to the 5.3 kb SOR2 probe. M=molecular weight standards.

FIG. 3 shows the reactions of tomato plants transformed with pSOR2-7 to Fenthion and Pst strains expressing avrPto. (A) Wild-type 76R inoculated with T1(avrPto). (B) Mutant prf-3 inoculated with T1(avrPto). (C) Mutant prf-3 transformed with pSOR2-7 and inoculated with T1(avrPto). (D) Wild-type 76R treated with fenthion. (E) Mutant prf-3 treated with fenthion. (F) Mutant prf-3 transformed with pSOR2-7 and treated with fenthion.

FIG. 4 shows the kinetics of bacterial growth in prf-3 plants transformed with pSOR2-7. Data points represent the mean of three replicate experiments+standard error.

FIG. 5 shows DNA gel blot analysis of the Prf locus in the prf-3 plant transformed with pSOR2-7. Genomic DNA was digested with XbaI, separated on a 0.75% agarose gel, and transferred to a Hybond N membrane. The blot was hybridized with a $^{32}P$-labeled probe corresponding to SOR2. Arrows indicate the sizes of molecular weight markers. M=molecular weight standards.

FIG. 6 shows segregation of resistance to Pst strains expressing avrPto and T-DNA in prf-3 mutant lines transformed with pSOR2-7.Genomic DNAs were digested with BglII, separated on an 0.75% agarose gel, and transferred to a Hybond N membrane. The blots were hybridized with the 2.5 kb BglII fragment of pCDLO4541. Plants were screened for resistance to T1(avrPto) by dipping in a solution of 10 mM $MgCl_2$, 0.05% Silwet L-77 (Union Carbide) containing $2\times10^8$ cfu/mL of T1(avrPto) and scored after five days. R=plants resistant to T1(avrPto); S=plants susceptible to T1(avrPto). The increased intensity of the band in the prf-3 pSOR2-7 lane is due to the amount of DNA loaded.

FIG. 7 shows the results of RNA gel blot analysis of Prf. Approximately 10 g of total RNA was separated on a 1.2% agarose gel containing 3.7% formaldehyde and transferred to a Hybond N membrane. (A) Membrane probed with the insert of pBS-Prf. (B) Membrane probed with DNA coding for the 18S rRNA.

FIG. 8 shows the physical structure of the Prf gene, including locations of lesions in prf mutations. Top shows an EcoRI restriction map of resistant tomato (76R) DNA in the vicinity of the Prf gene. The diagram below represents the Prf transcript, with exons indicated by straight horizontal lines and introns indicated by lines angled downward. The initiator (ATG) and termination (TAG) codons are indicated, as is the location of the 1.1 kb deletion in mutant prf-3. The locations and amino acid changes of three sequenced missense mutations are indicated by the downward pointing arrows.

FIGS. 9A–G shows the nucleotide sequence of the Prf cDNA protein-coding region.

FIGS. 10A–N shows the nucleotide sequence of a Prf genomic clone. The start of the protein coding sequence is at nucleotide 3879 and the stop is at nucleotide 9466.

FIG. 11 shows the predicted amino acid sequence of the Prf gene product. Residues underlined indicate regions of significance, as described in the text below.

FIG. 12 shows the primary structure of the Prf leucine-rich repeat, with consensus listed at bottom. Numbers on the left indicate the positions of residues in the Prf amino acid sequence.

FIG. 13 shows a region of internal repetition within the amino-terminal half of the Prf protein. Numbers on the left indicate the positions of residues in the Prf amino acid sequence.

Figure 15A:
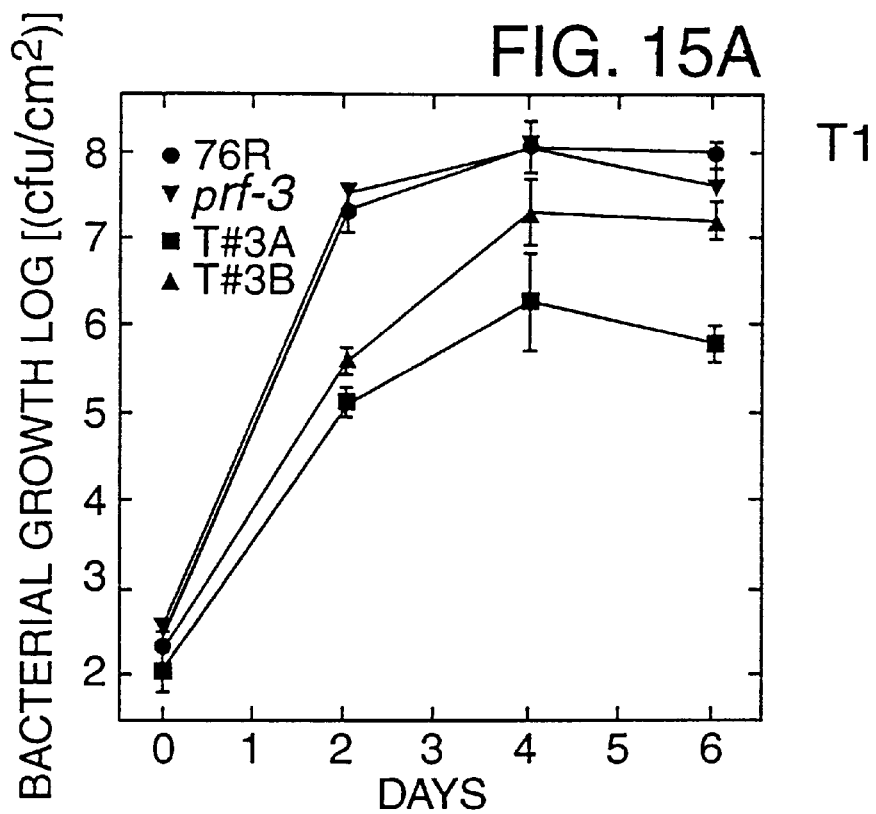
Figure 15B:
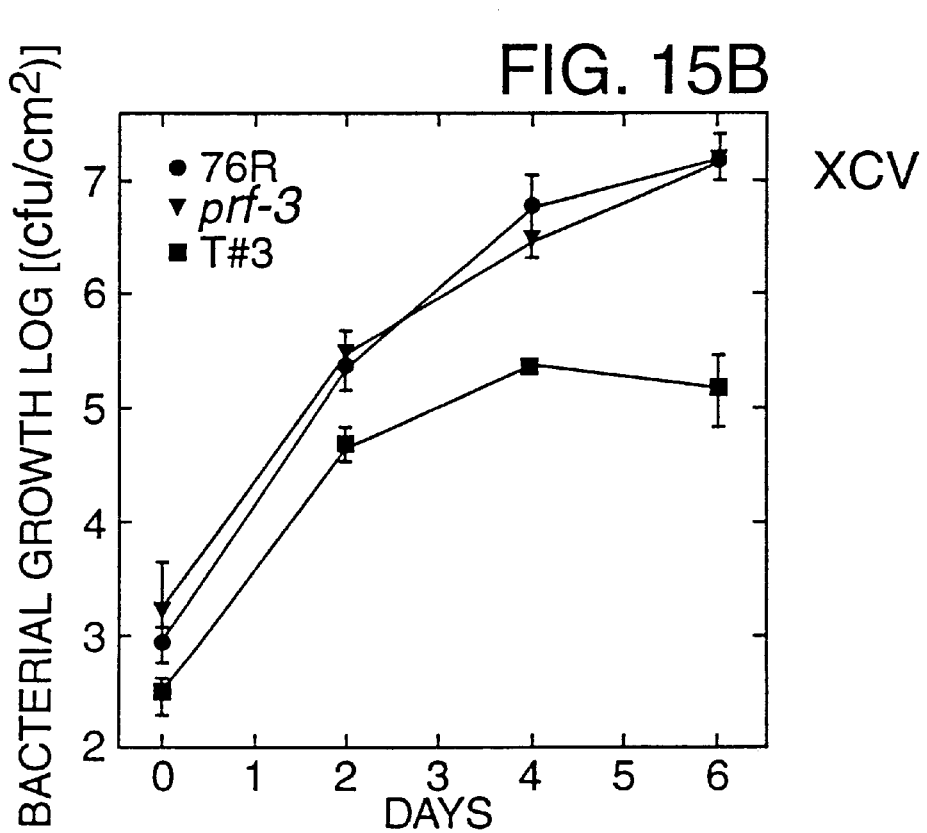

FIG. 15 shows growth of (A) Pst strain T1 and (B) *Xanthomonas campestris* pv. *vesicatoria* p38 in pSOR2-7-transformed plant prf-3 pSOR2-7 #3 (T#3). Data points represent the mean of three replicate experiments. Error bars show standard error.

DETAILED DESCRIPTION OF THE PREFERRED EMBODIMENTS

It has been discovered that the Prf gene is located within the Pto gene cluster. Prf encodes a protein with leucine-rich repeat, nucleotide binding, and leucine zipper motifs, which identifies it as a member of the resistance gene class that includes RPS2, RPM1, N and L6 (Staskawicz et al., *Science* 268:661–667, 1995; Dangl, *Cell* 80:383–386, 1995). Significantly, the cloned Prf gene complements a tomato prf mutant for both disease resistance and Fenthion sensitivity, demonstrating that Prf, like Arabidopsis RPM1, is a common component for transduction of distinct signals. The finding that the Prf protein contains LRRs demonstrates that, at least for the tomato-Pst system, the two major classes of plant disease resistance proteins, LRR-containing proteins and protein kinases, are components of the same signaling pathway.

Surprisingly, it has been demonstrated that transgenic plants that express the Prf gene display resistance not only to Pst but also to unrelated pathogens, including, but not limited to, *Xanthomonas campestris* pv. *vesicatoria*.

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, *Genes V,* Oxford University Press: New York, 1994. The nomenclature for DNA bases as set forth at 37 CFR 1.822 is used. The standard one- and three-letter nomenclature for amino acid residues is used.

The Genetic Basis for Resistance to Pathogens

Following the invasion of a plant by a potential pathogen, the pathogen either successfully proliferates in the host, causing associated disease symptoms, or its growth is halted by the defenses of the host plant. One such defense is the hypersensitive response (HR), a rapid cellular necrosis near the site of the infection that correlates with the generation of activated oxygen species, production of antimicrobial compounds, and reinforcement of host cell walls (Dixon and Lamb, *Annu. Rev. Plant Physiol. Plant Mol. Biol.* 41:339–367, 1990). Other defenses include systemic acquired resistance, which effectively protects the plant against subsequent attack by a broad range of pathogens (Ryals et al., *Proc. Natl. Acad. Sci. USA* 92:4202–4205, 1995).

Pathogens that elicit an HR on a given host are "avirulent" on that host, the host is "resistant," and the plant-pathogen interaction is "incompatible." If a pathogen proliferates and causes disease on the host, the pathogen is "virulent," the host is "susceptible," and the plant-pathogen interaction is "compatible."

In many cases in which a strains ("races") of a particular fungal or bacterial pathogen differ regarding virulence on a various cultivars (or wild accessions) of a particular host species, avirulent strains of the pathogen, but not virulent strains, possess one or more avirulence (avr) genes corresponding to "resistance" genes in the host. This observation is the basis for the "gene-for-gene" model of plant disease resistance (Crute et al., pp. 197–309 in *Mechanisms of Resistance to Plant Disease,* Fraser, ed., 1985; Ellingboe, *Annu. Rev. Phytopathol.* 19:125–143, 1981; Flor, *Annu. Rev. Phytopathol.* 9:275–296, 1971; and Keen et al., in *Application of Biotechnology to Plant Pathogen Control,* Chet, ed., John Wiley & Sons, 1993, pp. 65–88).

Normally avirulence and resistance genes are organized in functional pairs. A given resistance gene is generally effective only against pathogen strains that express a specific cognate avirulence gene (Flor, *Annu. Rev. Phytopathol.* 9:275–296, 1971; Keen, *Annu. Rev. Genet.* 24:447–463, 1990). However, exceptions to this rule exist. For example the Arabidopsis RPM1 gene product (Grant et al., *Science* 269:843–846, 1995) is involved in the recognition of elicitors produced by *P. syringae* expressing the avirulence genes avrRpm1 or avrB (Bisgrove et al., *Plant Cell* 6:927–933, 1994), suggesting that resistance gene products may function as common points in transduction of distinct pathogen signals.

Resistance gene products are activated in response to pathogen signal molecules termed elicitors, production of which is controlled by pathogen avirulence genes.

A number of avirulence genes have been cloned (Long and Staskawicz, *Cell* 73:921–935, 1993; Dangl, in *Bacterial Pathogenesis of Plants and Animals,* Dangl, ed., Springer-Verlag, 1994, pp. 99–118; Innes et al., *J. Bacteriol.* 175:4859–4869, 1993; Dong, et al., *Plant Cell* 3:61–72, 1991; Whelan et al., *Plant Cell* 3:49–59, 1991; Staskawicz et al., *J. Bacteriol.* 169:5789–5794, 1987; Gabriel et al., *Proc. Natl. Acad. Sci. USA* 83:6415–6419, 1986; Keen and Staskawicz, *Annu. Rev. Microbiol.* 42:421–440, 1988; Kobayashi et al., *Mol. Plant-Microbe Interact.* 3:94–102 and 3:103–111, 1990). Many cloned avirulence genes have been shown to correspond to individual resistance genes in the cognate host plants and confer an avirulent phenotype when transferred to an otherwise virulent strain.

Examples of known signals to which plants respond when infected by pathogens include harpins from Erwinia (Wei et al., *Science* 257:85–88, 1992) and Pseudomonas (He et al.,

*Cell* 73:1255–1266, 1993); avr4 (Joosten et al., *Nature* 367:384–386, 1994) and avr9 peptides (van den Ackerveken et al., *Plant J.* 2:359–366, 1992) from Cladosporium; PopA1 from Pseudomonas (Arlat et al., *EMBO J.* 13:543–553, 1994); avrD-generated lipopolysaccharide (Midland et al., *J. Org. Chem.* 58:2940–2945, 1993); and NIP1 from Rhynchosporium (Hahn et al., *Mol. Plant-Microbe Interact.* 6:745–754, 1993).

A number of plant disease resistance genes have also been cloned (Bent et al., *Science* 265:1856–1860, 1994; Grant et al., *Science* 269:843–846, 1995; Jones et al., *Science* 266:789–792, 1994; Martin et al., *Science* 262:1432–1436, 1993; Mindrinos et al., *Cell* 78:1089–1099, 1994; Song et al., *Science* 270:1804–1806, 1995; Whitham et al., *Cell* 78:1101–1115, 1994).

Similar features have been discovered among many of these resistance genes, in spite of the diversity of pathogens against which they act. These features include a leucine-rich-repeat (LRR), a motif found in a multitude of eukaryotic proteins with roles in signal transduction (Kobe and Deisenhofer, *Trends Biochem. Sci.* 19:415–421, 1994). The LRR motif is thought to be involved in protein-protein interactions and may allow interaction with other proteins that are involved in plant disease resistance. In addition, sequences predicted to encode nucleotide binding sites and leucine zippers are shared among many resistance genes (Dangl, *Cell* 80:383–386, 1995; Staskawicz et al., *Science* 268:661–667, 1995). These motifs are present and similarly organized among resistance gene products from plants as diverse as tobacco, tomato, rice, flax, and Arabidopsis, suggesting a common mechanism underlying disease resistance signal transduction throughout the plant kingdom.

A race-specific resistance gene from *Zea mays* (corn), Hm1 (Johal and Briggs, *Science* 258:985–987, 1992), confers resistance against specific races of the fungal pathogen *Cochliobolus carbonum* by controlling degradation of a fungal toxin. This strategy is mechanistically distinct from the avirulence-gene specific resistance of the Prf-avrPto resistance mechanism.

Nucleic Acids

"Prf Gene". The term "Prf gene" or "Prr" refers to a native Prf-encoding nucleic acid sequence or a fragment thereof, e.g., the native tomato Prf cDNA or genomic sequences and alleles and homologs thereof. The term also encompasses variant forms of a native Prf nucleic acid sequence or fragment thereof as discussed below, preferably a nucleic acid that encodes a polypeptide having Prf biological activity. Native Prf sequences include cDNA sequences and the corresponding genomic sequences (including flanking or internal sequences operably linked thereto, including regulatory elements and/or intron sequences).

"Disease Resistance Gene". The term "disease resistance gene" refers to a plant gene such as Prf that encodes a polypeptide capable of triggering the defense response of a plant cell or tissue.

"Native". The term "native" refers to a naturally-occurring ("wild-type") nucleic acid or polypeptide.

"Homolog". A "homolog" of a tomato Prf gene is a gene sequence encoding a Prf polypeptide isolated from a plant other than tomato.

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, Probes, and Primers. A fragment of a Prf nucleic acid is a portion of a Prf nucleic acid that is less than full-length and comprises at least a minimum length capable of hybridizing specifically with a native Prf nucleic acid under stringent hybridization conditions. The length of such a fragment is preferably at least 15 nucleotides, more preferably at least 20 nucleotides, and most preferably at least 30 nucleotides of a native Prf nucleic acid sequence.

Nucleic acid probes and primers can be prepared based on a native Prf gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to the tomato Prf sequence under high stringency hybridization conditions and hybridize specifically to a native Prf sequence of another species under at least moderately stringent conditions. Preferably, probes and primers according to the present invention have complete sequence similarity with the native tomato Pfr sequence, although probes differing from the tomato Pfr sequence and that retain the ability to hybridize to native Prf sequences may be designed by conventional methods.

Methods for preparing and using probes and primers are described, for example, in *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990. PCR-primer pairs can be derived from a known sequence, for example, by using computer programs intended for that purpose such-as Primer (Version 0.5, 1991, Whitehead Institute for Biomedical Research, Cambridge, Mass.).

Primers and probes based on the native tomato Prf sequences disclosed herein can be used to confirm (and, if necessary, to correct) the disclosed Prf sequences by conventional methods, e.g., by re-cloning and sequencing a tomato Prf cDNA or genomic sequence.

Substantial Similarity. A first nucleic acid is "substantially similar" to a second nucleic acid if, when optimally aligned (with appropriate nucleotide insertions or deletions) with the other nucleic acid (or its complementary strand), there is at least about 75% nucleotide sequence identity, preferably at least about 80% identity, more preferably at least about 85% identity, and most preferably at least about 90% identity. Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic-acid manipulation are well-known (see, e.g., Sambrook et al., 1989, and Ausubel et al., 1992). Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic acids; Vectors, Transformation, Host cells. Natural or synthetic nucleic acids according to the present invention can be incorporated into recombinant nucleic-acid constructs, typically DNA constructs, capable of introduction into and replication in a host cell. Such a construct preferably is a vector that includes a replication system and sequences that are capable of transcription and translation of a polypeptide-Oncoding sequence in a given host cell.

For the practice of the present invention, conventional compositions and methods for preparing and using vectors and host cells are employed, as discussed, inter alia, in Sambrook et al., 1989, or Ausubel et al., 1992.

A cell, tissue, organ, or organism into which has been introduced a foreign nucleic acid, such as a recombinant vector, is considered "transformed", "transfected", or "transgenic." A "transgenic" or "transformed" cell or organism also includes progeny of the cell or organism and progeny produced from a breeding program employing such a "transgenic" plant as a parent in a cross and exhibiting an altered phenotype resulting from the presence of a recombinant Prf nucleic acid construct.

A number of vectors suitable for stable transfection of plant cells or for the establishment of transgenic plants have been described in, e.g., Pouwels et al., *Cloning Vectors: A Laboratory Manual,* 1985, supp. 1987); Weissbach and Weissbach, *Methods for Plant Molecular Biology,* Academic Press, 1989; and Gelvin et al., *Plant Molecular Biology Manual,* Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A function Prf gene can be expressed in plant cells under the control of the tomato Prf promoter sequence disclosed herein, for example.

Examples of constitutive plant promoters useful for expressing Prf genes include, constitutive plant promoters, including, but not limited to, the cauliflower mosaic virus (CaMV) 35S promoter, which confers constitutive, high-level expression in most plant tissues (see, e.g., Odel et al., *Nature* 313:810, 1985), including monocots (see, e.g., Dekeyser et al., *Plant Cell* 2:591, 1990; Terada and Shimamoto, *Mol. Gen. Genet.* 220:389, 1990); the nopaline synthase promoter (An et al., *Plant Physiol.* 88:547, 1988) and the octopine synthase promoter (Fromm et al., *Plant Cell* 1:977, 1989).

A variety of plant gene promoters that are regulated in response to environmental, hormonal, chemical, and/or developmental signals, also can be used for expression of Prf in plant cells, including promoters regulated by (1) heat (Callis et al., *Plant Physiol.* 88:965, 1988), (2) light (e.g., pea rbcS-3A promoter, Kuhlemeier et al., *Plant Cell* 1:471, 1989; maize rbcS promoter, Schaffner and Sheen, *Plant Cell* 3:997, 1991; or chlororphyll a/b-binding protein promoter, Simpson et al., *EMBO J.* 4:2723, 1985), (3) hormones, such as abscisic acid (Marcotte et al., *Plant Cell* 1:969, 1989), (4) wounding (e.g., wunl, Siebertz et al., *Plant Cell* 1:961, 1989); or (5) chemicals such as methyl jasminate, salicylic acid, or Safener. It may also be advantageous to employ (6) organ-specific promoters (e.g., Roshal et al., *EMBO J.* 6:1155, 1987; Schernthaner et al., *EMBO J.* 7:1249, 1988; Bustos et al., *Plant Cell* 1:839, 1989).

Plant expression vectors optionally include RNA processing signals, e.g., introns, which may be positioned upstream or downstream of an Prf polypeptide-encoding sequence in the transgene. In addition, the expression vectors may also include additional regulatory sequences from the 3'-untranslated region of plant genes (Thornburg et al., *Proc. Natl. Acad. Sci. USA* 84:744 (1987); An et al., *Plant Cell* 1:115 (1989), e.g., a 3' terminator region to increase mRNA stability of the mRNA, such as the PI-II terminator region of potato or the octopine or nopaline synthase 3' terminator regions.

Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, *Cell Culture and Somatic Cell Genetics of Plants,* Vols. I–III, Laboratory Procedures and Their Applications Academic Press, New York, 1984.

Nucleic-Acid Hybridization; "Stringent Conditions"; "Specific". The nucleic-acid probes and primers of the present invention hybridize under stringent conditions to a target DNA sequence, e.g., to a Prf gene.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product.

For hybridization of a tomato Prf probe to a nucleic acid of another plant species in order to identify Prf homologs, preferred hybridization and washing conditions are described in the Examples below.

The term "specific for (a target sequence)" indicates that a probe or primer hybridizes under given hybridization conditions only to the target sequence in a sample comprising the target sequence.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications,* ed. Innis et al., Academic Press, San Diego, 1990.

Nucleotide-Sequence Variants of Native Prf Nucleic Acids and Amino Acid Sequence Variants of Native Prf Proteins. Using the nucleotide and the amino-acid sequence of the Prf polypeptides disclosed herein, those skilled in the art can create DNA molecules and polypeptides that have minor variations in their nucleotide or amino acid sequence.

"Variant" DNA molecules are DNA molecules containing minor changes in a native Prf sequence, i.e., changes in which one or more nucleotides of a native Prf sequence is deleted, added, and/or substituted, preferably while substantially maintaining a Prf biological activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in Prf biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native Prf sequence or a homolog thereof in which there has been a substitution of one or more base pairs but no change in the amino-acid sequence of the polypeptide encoded by the sequence. "Conservative" variants are variants of the native Prf sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed below. In addition, one or more codons encoding cysteine residues can be substituted for, resulting in a loss of a cysteine residue and affecting disulfide linkages in the Prf polypeptide.

TABLE 1

| Original Residue | Conservative Substitutions |
|---|---|
| Ala | ser |
| Arg | lys |
| Asn | gln, his |
| Asp | glu |
| Cys | ser |

TABLE 1-continued

| Original Residue | Conservative Substitutions |
|---|---|
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Nucleic Acids Attached to a Solid Support. The nucleic acids of the present invention can be free in solution or covalently or noncovalently attached by conventional means to a solid support, such as a hybridization membrane (e.g., nitrocellulose or nylon), a bead, etc.

Polypeptides

"Prf Protein". The term "Prf protein" (or polypeptide) refers to a protein encoded by a Prf nucleic acid, including alleles, homologs, and variants of a native Prf nucleic acid, for example. A Prf polypeptide can be produced by the expression of a recombinant Prf nucleic acid or be chemically synthesized. Techniques for chemical synthesis of polypeptides are described, for example, in Merrifield, *J. Amer. Chem. Soc.* 85:2149–2156, 1963.

Polypeptide Sequence Homolony. Ordinarily, Prf polypeptides encompassed by the present invention are at least about 70% homologous to a native Prf polypeptide, preferably at least about 80% homologous, and more preferably at least about 95% homologous. Such homology is considered to be "substantial homology," although more important than shared amino-acid sequence homology can be the common possession of characteristic structural features and the retention of biological activity that is characteristic of Prf, preferably Prf catalytic activity.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. Various methods of protein purification are described, e.g., in *Guide to Protein Purification*, ed. Deutscher, *Meth. Enzymol.* 185, Academic Press, San Diego, 1990; and Scopes, *Protein Purification: Principles and Practice*, Springer Verlag, New York, 1982.

Variant and Modified Forms of Prf Polypeptides. Encompassed by the Prf polypeptides of the present invention are variant polypeptides in which there have been substitutions, deletions, insertions or other modifications of a native Prf polypeptide. The variants substantially retain structural characteristics and biological activities of a corresponding native Prf polypeptide and are preferably silent or conservative substitutions of one or a small number of contiguous amino acid residues.

A native Prf polypeptide sequence can be modified by conventional methods, e.g., by acetylation, carboxylation, phosphorylation, glycosylation, ubiquitination, and labeling, whether accomplished by in vivo or in vitro enzymatic treatment of a Prf polypeptide or by the synthesis of a Prf polypeptide using modified amino acids.

Labeling. There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel etal., 1992.

Polypeptide Fragments. The present invention also encompasses fragments of a Prf polypeptide that lacks at least one residue of a native full-length Prf polypeptide. Preferably, such a fragment retains the ability to confer resistance to Pst or sensitivity to Fenthion when expressed as a transgene in a plant or possession of a characteristic functional domain, or an immunological determinant characteristic of a native Prf polypeptide. Immunologically active fragments typically have a minimum size of 7 to 17 or more amino acids.

The terms "biological activity", "biologically active", "activity" and "active" refer primarily to the characteristic biological activity or activities of a native Prf polypeptide, including, but not limited to, the ability to confer Pst resistance or Fenthion sensitivity to a transgenic plant.

Fusion Polypeptides. The present invention also provides fusion polypeptides including, for example, heterologous fusion polypeptides in which a Prf polypeptide sequence is joined to a fusion partner. Such fusion polypeptides can exhibit biological properties (such as substrate or ligand binding, enzymatic activity, antigenic determinants, etc.) derived from each of the fused sequences. Any conventional fusion partner can be used, including, for example, glucuronidase, beta galactosidase, etc. Fusion polypeptides are preferably made by the expression of recombinant nucleic acids produced by standard techniques.

Polypeptide Sequence Determination. The sequence of a polypeptide of the present invention can be determined by any of the various methods known in the art.

Polypeptide Coupling to a Solid Phase Support. The polypeptides of the present invention can be free in solution or coupled to a solid-phase support, e.g., nitrocellulose, nylon, column packing materials (e.g., Sepharose beads), magnetic beads, or glass wool, by conventional methods.

Antibodies

The present invention also encompasses polyclonal and/or monoclonal antibodies capable of specifically binding to a Prf polypeptide and/or fragments thereof. Such antibodies are raised against a Prf polypeptide or fragment thereof and are capable of distinguishing a Prf polypeptide from other polypeptides, i.e., are Prf-specific.

For the preparation and use of antibodies according to the present invention, including various immunoassay techniques and applications, see, e.g., Goding, *Monoclonal Antibodies: Principles and Practice*, 2d ed, Academic Press, New York, 1986; and Harlow and Lane, *Antibodies: A Laboratory Manual*, Cold Spring Harbor Laboratory, Cold Spring Harbor, N.Y., 1988. Prf-specific antibodies are useful, for example in: purifying a Prf polypeptide from a biological sample, such as a host cell expressing recombinant a Prf polypeptide; in cloning a Prf allele or homolog from an expression library; as antibody probes for protein blots and immunoassays; etc.

Prf polypeptides and antibodies can be labeled by any of a variety of conventional methods. Suitable labels include, but are not limited to, radionuclides, enzymes, substrates, cofactors, inhibitors, fluorescent agents, chemiluminescent agents, magnetic particles, etc.

Obtaining Alleles and Homologs of Tomato Prf

As discussed in the Examples below, fragment(s) homologous to Prf exist in many plant species. Using moderately high stringency hybridization conditions, most species tested showed one or two homologous fragments, while a large homologous gene family of approximately nine members was detected in tobacco. Based upon the availability of the tomato Prf cDNA and genomic sequences as disclosed herein, alleles of the cloned tomato Prf gene and homologs from other plant species can be obtained by conventional methods, e.g., by screening a cDNA or genomic library with a probe that specifically hybridizes to a native Prf sequence under at least moderately stringent conditions (e.g., the tomato Prf cDNA or a fragment thereof), by PCR or another amplification method using a primer or primers that specifically hybridize to a native Prf sequence under at least moderately stringent conditions, or by identification of Prf alleles or homologs in an expression library using Prf-specific antibodies.

Probes and primers based on the tomato Prf sequence disclosed herein can also be used to obtain other plant disease resistance genes having substantial similarity to tomato Prf by conventional methods.

Plant Transformation and Regeneration

Various nucleic acid constructs that include a Prf nucleic acid are useful for producing pathogen-resistant plants.

Prf nucleic acids can be expressed in plants or plant cells under the control of a suitable operably linked promoter that is capable of expression in a cell of a particular plant. Any well-known method can be employed for plant cell transformation, culture, and regeneration in the practice of the present invention with regard to a particular plant species. Conventional methods for introduction of foreign DNA into plant cells include, but are not limited to: (1) Agrobacterium-mediated transformation (Lichtenstein and Fuller In: *Genetic Engineering*, Vol 6, Rigby, ed., London, Academic Press, 1987; and Lichtenstein and Draper, in: *DNA Cloning*, Vol II, Glover, ed., Oxford, IRI Press, 1985); (2) particle delivery (see, e.g., Gordon-Kamm et al., *Plant Cell* 2:603, 1990; or BioRad Technical Bulletin 1687), (3) microinjection (see, e.g., Green et al., *Plant Tissue and Cell Culture*, Academic Press, New York, 1987), (4) polyethylene glycol (PEG) procedures (see, e.g., Draper et al., *Plant Cell Physiol.* 23:451, 1982); Zhang and Wu, *Theor. Appl. Genet.* 76:835, 1988), (5) liposome-mediated DNA uptake (see, e.g., Freeman et al., *Plant Cell Physiol.* 25:1353, 1984), (6) electroporation (see, e.g., Fromm et al., *Nature* 319:791 (1986)); and (7) vortexing method (see, e.g., Kindle, *Proc. Natl. Acad. Sci. USA* 87:1228 (1990)).

The term "plant" encompasses any higher plant and progeny thereof, including monocots (e.g., lily, corn, rice, wheat, barley, etc.), dicots (e.g., tomato, potato, soybean, cotton, tobacco, etc.), and includes parts of plants, including reproductive units of a plant (e.g., seeds), fruit, flowers, etc.

A "reproductive unit" of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

A Prf transgene is useful for conferring disease resistance on plants that would otherwise be susceptible to plant pathogens carrying the avirulence gene, avrPto, e.g., Pst. Several cloned plant host resistance genes confer disease resistance to transgenic plants. For example, the N gene of tobacco confers resistance to a viral pathogen (TMV) (Whitham et al., *Cell* 78:1101–1115, 1994); the RPM1 gene of Arabidopsis confers resistance to *Pseudomonas syringae* strains carrying the avrRpm1 avirulence gene (Grant et al., *Science* 269:843–846, 1995; and the L6 gene of flax confers resistance to flax rust, a fungal pathogen (Lawrence et al., *Plant Cell* 7:1195–1206, 1995).

As demonstrated in the Examples below, expression of Prf in transgenic plants can confer resistance not only to Pst but also to *Xanthomonas campestris* pv. *vesicatoria* and to a wide variety of other phytopathogens, including, but not limited to, bacteria, viruses (e.g., tobacco mosaic virus, potato virus X, etc.), fungi (e.g., *Phytophthora infestans*, Fusarium spp., etc.), and nematodes (e.g., root knot nematode, etc.). To confer such broad-spectrum pathogen resistance, it is preferable to express a Prf transgene at high levels, e.g., through expression of multiple copies of the Prf transgene and/or the use of strong promoters to drive Prf expression. Expression of a Prf transgene in plant cells at a sufficiently high level may initiate the plant defense response constitutively in the absence of signals from the pathogen. The level of Prf mRNA and polypeptide expression can be determined by conventional methods. Prf transgene expression can be driven by its own promoter or by a heterologous promoter. An inducible, or tissue-specific promoter, for example, can be used to limit the temporal and tissue expression of a defense response.

The Prf gene can be co-expressed in a plant cell with the avrPto gene to mimic the production of gene products associated with the initiation of the plant defense response and provide resistance to pathogens in the absence of specific resistance gene-avirulence gene corresponding pairs in the host plant and pathogen.

The invention will be better understood by reference to the following Examples, which are intended to merely illustrate the best mode now known for practicing the invention. The scope of the invention is not to be considered limited thereto.

EXAMPLES

Experimental Procedures

Mapping the Prf Gene. To map the Prf gene relative to Pto, $F_2$ progeny from crosses of prf mutant plants (prf Pto/prf Pto) to tomato line 76S (Prf pto/Prf pto; Carland and Staskawicz, *Mol. Gen. Genet.* 239:17–27, 1993) were analyzed for the presence of recombinant chromosomes carrying wild-type alleles of both genes. Out of 413 progeny, tested by scoring for resistance to transconjugants of Pst strain T1 containing the avrPto plasmid pPtE6 (Ronald et al., *J. Bacteriol.* 174:1604–1611, 1992), none were recombinant, indicating a maximal genetic distance between Prf and Pto of 0.12 cM.

Construction of YAC and Cosmid Contigs Spanning the Prf/Pto Region. All plasmid and cosmid manipulations, preparation of bacterial and yeast media, and hybridization techniques were performed using standard protocols (Ausubel et al., 1992). Tomato RFLP clones TG538 and TG475, which had been previously mapped to the Prf/Pto region (Martin et al., *Mol. Plant-Microbe Interact.* 6:26–34, 1993), were obtained from Dr. Steven Tanksley (Cornell University). In addition, YAC clones corresponding to TG475, VC111.C6 and VC107.D6 (Martin et al., *Mol. Plant-Microbe Interact.* 6:26–34, 1993), were obtained independently from Drs. Steven Tanksley and Valerie Williamson (University of California, Davis). Ends of these two YACs were isolated and used to identify polymorphic bands between near-isogenic lines 76R (Prf Pto/Prf Pto) and 76S (Prf pto/Prf pto), which differ in the presence or absence of the Pto gene. The markers could then be mapped relative to Pto by probing a mapping population of 1414 $F_2$ individuals from a cross of 76R to 76S. This revealed that the left end of YAC VC111.C6 was closer to Pto than TG475. TG538 and this YAC end were sequenced and oligonucleotides synthesized to create primer pairs corresponding to each marker. Primers for TG538 were:

5'-CCAAGTGCAGAGAGTACTGGA-3' and
5'-TGAATGAACATGATCAAAGTATGC-3';

primers for the left end of YAC VC111.C6 were:

5'-ACTCCAGAACCAATGATTGCATA-3' and
5'-GGAATTTAAATCTAGAATATCTC-3'.

Primers pairs were used to screen a copy of the Tanskley tomato YAC library obtained from the NSF Center for Engineering Plants for Resistance Against Pathogens. YAC clones RG209.H9, RG220.G1, VC168.G12, VC162.H11, VC5.2, and VC1.F8 were found to contain the left end of VC111.C6, and clones VC168.G12, RG269.D3, RG669.C9 and RG675.C2 were found to contain TG538. YAC ends were subcloned and mapped relative to other YACs and to the Pto gene to construct a contig across the Prf/Pto region (FIG. 1B). Additional markers tightly linked to Pto were derived by subcloning fragments from the contig and mapped by probing the 76R×76S $F_2$ population. In this way, RFLP marker VC168S (a copy of the repetitive right end of YAC VC5.2) was mapped to 0.035 cM from Pto and marker TG538 was mapped to 0.00 cM of Pto.

To form cosmid contigs across the Pto/Prf locus, libraries of 10–20 kb insert size were constructed in pCDL04541 (Jones et al., *Transgenic Research* 1:285–297, 1992) from yeast containing either of VC168.G12 or RG269.D3. VC168S and TG538 were used as probes to isolate corresponding clones from the cosmid libraries. Cosmid ends were cloned and used in recurrent probing of libraries to eventually form contigs of 167 kb (VC168.G12) spanning VC168S and TG538 and 80 kb (RG269.D3). Cosmids pSOR1-3 and pSOR2-7, from VC168.G12, bear the 5 kb EcoRI fragment SOR2 that contains most of the Prf coding sequence. SOR2 was identified as Prf by a mutational alteration within the fragment, as discussed below.

Cloning the Prf Gene. To construct the tomato cDNA library, line 76R was vacuum infiltrated with a solution of Pst strain T1(avrPto) at a concentration of $5\times10^7$ cfu/mL. Leaf tissue was harvested after 6 hr incubation at room temperature and the library was constructed using a ZAP-cDNA Synthesis kit (Stratagene). The cDNA library of VFNT Cherry was provided by Dr. Wilhelm Gruissem. Approximately $1.6\times10^6$ clones were screened from the 76R library, with five hybridizing plaques obtained, and $2\times10^5$ clones from the VFNT Cherry library with three hybridizing plaques obtained. The longest cDNA (1.2 kb) was designated Cdr1. As an initial step to obtain a full-length cDNA for Prf, primers throughout the SOR2 region were used in combination with a primer corresponding to the trailer mRNA of Cdr1 in PCR reactions using 76R mRNA as template and a Stratascript kit (Stratagene). The longest clone was obtained using 5'-CCTTCTATTCATCATCC-3' and 5'-CTGCTCCTGATTCTTCT-3' as amplification primers. This 4.0 kb band was cloned into the XhoI and XbaI sites of pBluescript-KS(+) (Stratagene) to form pBS-Prf.

5' RACE analysis (Frohman et al., *Proc. Nat. Acad. Sci. USA* 85:8998–9002, 1988) was performed to identify the 5' end of the Prf transcript. The Life Technologies 5'RACE kit (Cat. No. 18374-025) was used as specified by the manufacturer, except that first strand cDNAs were tailed with dATP instead of dCTP. The primer "T Prime" (5'-TTGCATTGACGTCGACTATCCAGGTTTTTTTTTTT TTT-3') was substituted for the primer supplied with the kit in all the subsequent PCR amplifications. In each RACE experiment, first strand cDNA was synthesized from 0.25mg of poly-$A^+$ RNA isolated from tomato cultivar 76R. Two separate RACE reactions were performed to confirm the 5' end of the Prf transcript. The first experiment used a Prf-specific primer PrfPX1 (5'-TAAGATATGTAACCATGAGCAACAACCCTTC-3'; SEQ ID NO: 14) to prime CDNA synthesis. The sequence of PrfPX1 was chosen from analysis of the pBS-Prf insert. After dATP tailing, primers T Prime and PrfPX2 (5'-GACCTCATCTGCAATAGTA-3') were used for PCR amplification. The reaction yielded a 2.0 kb product which was captured in the vector pCRII (Invitrogen). Two clones from this PCR amplification, SS071.7 and SS071.11, were sequenced and indicated transcripts with 5' ends 5648 nucleotides and 5640 nucleotides, respectively, upstream from the codon terminating the Prf ORF. The second 5' RACE experiment was performed using Prf-specific primers closer to the 5' ends mapped by the first RACE reaction. Primer PrfPX1B (5'-AGGCCCTGCACTGATAAAGAACAA-3') was used to prime cDNA synthesis, and primer PrfPX2B (5'-AGCAGCTCTGGGATCACTTGCCTT-3') was used with T Prime for the PCR amplification. This reaction resulted in a 0.53 kb amplification product which was also cloned in pCRII. Five clones were sequenced. The longest two clones (SS074.3 and SS074.12) indicated transcripts with 5' ends 5638 and 5677 bp, respectively, upstream of the termination codon.

DNA Sequencing. The insert of pBS-Prf along with the 5' RACE products were sequenced either with Sequenase (United States Biochemical Corporation) by the dideoxynucleotide method, or using an Applied Biosystems 373 DNA Sequencer or a Licor DNA sequencer. Sequence data was compiled and analyzed using the Sequencher software (GeneCodes, Inc.). To obtain the sequence of the Prf genomic clones, the 5 kb SOR2 fragment was excised from cosmids R207 (from resistant tomato) and pSOR2-7 (susceptible tomato), cut with HindIII, subcloned into pBluescript KS-(+), and sequenced as described above. Subclones of mutant prf alleles were amplified from genomic DNAs using Prf-specific primers, ligated into pCRII (Invitrogen), and sequenced.

Complementation. Cosmid pSOR2-7 was introduced into tomato mutant line prf-3 by Agrobacterium-mediated transformation of excised cotyledons essentially as described by McCormick et al., 1986. Transgenic plants were identified by resistance to kanamycin (50 μg/ml) and confirmed by DNA gel blot analysis. Transformants were analyzed by inoculation with Pst strain T1(avrPto) and exposure to Fenthion as described previously (Carland and Staskawicz, *Mol. Gen. Genet.* 239:17–27, 1993).

Gel Blot Analysis. DNA and RNA gel blot analysis was performed using standard procedures (Ausubel et al., 1992). In the RNA gel blot analysis, hybridization was performed in the presence of 10% dextran sulfate. For testing for homologs to Prf in other plant species, hybridization was performed using a radiolabelled 1.4 kb HindIII fragment from pSOR2-7, corresponding to nucleotides 3150–4494 of Prf, under conditions of 65 C., 6×SSC. Washing was performed for 1 hour in 0.5×SSC, 0.5%SDS at 65 C. The molecular weight standards used were the 1-kb Ladder (Bethesda Research Laboratories) and the 0.24–9.5-kb RNA Ladder (Gibco BRL).

Results

Construction of YAC and Cosmid Contigs Across the Prf/Pto Locus. There is tight linkage between the Prf and Pto genes, as shown through analysis of $F_2$ progeny from crosses of prf mutant plants to pto mutant lines (Salmeron et al., *Plant Cell* 6:511–520, 1994). Analysis of additional prfxpto $F_2$ individuals allowed us to assign Prf to a distance of no more than 0.12 cM from Pto. Given the estimated ratio of 220 kb/cM for the region around Pto, as derived from analysis of a YAC clone spanning the Pto gene (Martin et al., *Science* 262:1432–1436, 1993), we employed molecular markers in the vicinity of the Pto locus (Martin et al., *Mol. Plant-Microbe Interact.* 6:26–34, 1993) to expedite cloning of the Prf gene. FIG. 1A shows RFLP markers that are tightly linked to the Pto gene and that lie within a distance to which Prf had been genetically mapped relative to Pto.

Initially, we constructed a contig of approximately 400 kb that included eleven YACs in the vicinity of Pto by probing available YAC libraries with Pto-linked markers (FIG. 1B; Martin et al., *Mol. Plant-Microbe Interact.* 6:26–34, 1993). Positioning the ends of these YACs on the genetic map led us to focus on two markers, VC168S and TG538, which mapped to 0.04 and 0.00 cM from the Pto locus (FIG. 1A). These markers were used as probes to isolate corresponding cosmids from libraries of 76R (Pto Prf/Pto Prf) and VFNT Cherry (pto Prf/pto Prf) DNAs. Cosmid walking from these starting points resulted in the construction of contigs which span 80 kb (76R DNA) and 167 kb (VFNT Cherry DNA).

Localization of the Prf Gene Within Cosmid Contigs. Mutations in the prf gene had been isolated with fast neutrons and diepoxybutane, agents that were known to cause deletion mutations in other eukaryotic systems (Reardon et al., *Genetics* 115:323–331, 1987; Sun et al., *Plant Cell* 4:119–128, 1992). Given the tight linkage between the Prf and Pto genes, and the availability of cosmids from the Pto region, we decided to test for the presence of deletions in prf mutant plants that could be used to localize the Prf gene. Single-copy probes were identified throughout the cosmid contigs and hybridized to gel blots of prf mutant DNAs. A 5.3 kb EcoRI fragment, designated SOR2 (FIG. 1C), detected a 1.1 kb alteration in mutant line prf-3 (FIG. 2), a plant isolated by fast neutron bombardment (Salmeron et al., *Plant Cell* 6:511–520, 1994). Fragments adjacent to SOR2 detected no alteration in prf-3, suggesting that prf-3 comprised a simple deletion within the SOR2 fragment. No additional alterations were observed with other probes or in DNAs from other prf mutant lines.

Figure 3C:
Figure 3F:
Figure 3B:
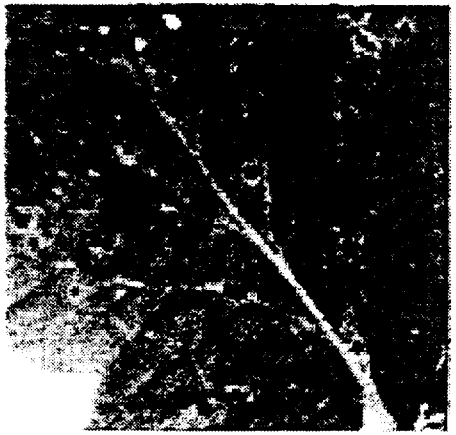
Figure 3E:
Figure 3A:

Complementation of the prf-3 Mutation by Cosmids Containing SOR2. To directly test whether the region surrounding SOR2 encodes Prf activity, cosmids containing SOR2 were introduced into the tomato mutant prf-3 by Agrobacterium-mediated transformation. Transgenic plants, selected for kanamycin resistance, were inoculated with Pst strain T1 (normally virulent on Pto Prf tomatoes) and a transconjugant, T1(avrPto), that expresses the avrPto avirulence gene and is recognized by tomatoes expressing the Prf and Pto genes (Ronald et al., *J. Bacteriol.* 174:1604–1611, 1992). Plants were dipped in a solution of 10 mM $MgCl_2$, 0.05% Silwet L77 (Union Carbide) containing $2\times10^8$ cfu/mL of Pst strain T1(avrPto) (Ronald et al., *J. Bacteriol.* 174:1604–1611, 1992) and photographed after five days (FIGS. 3A–C).

Figure 4:
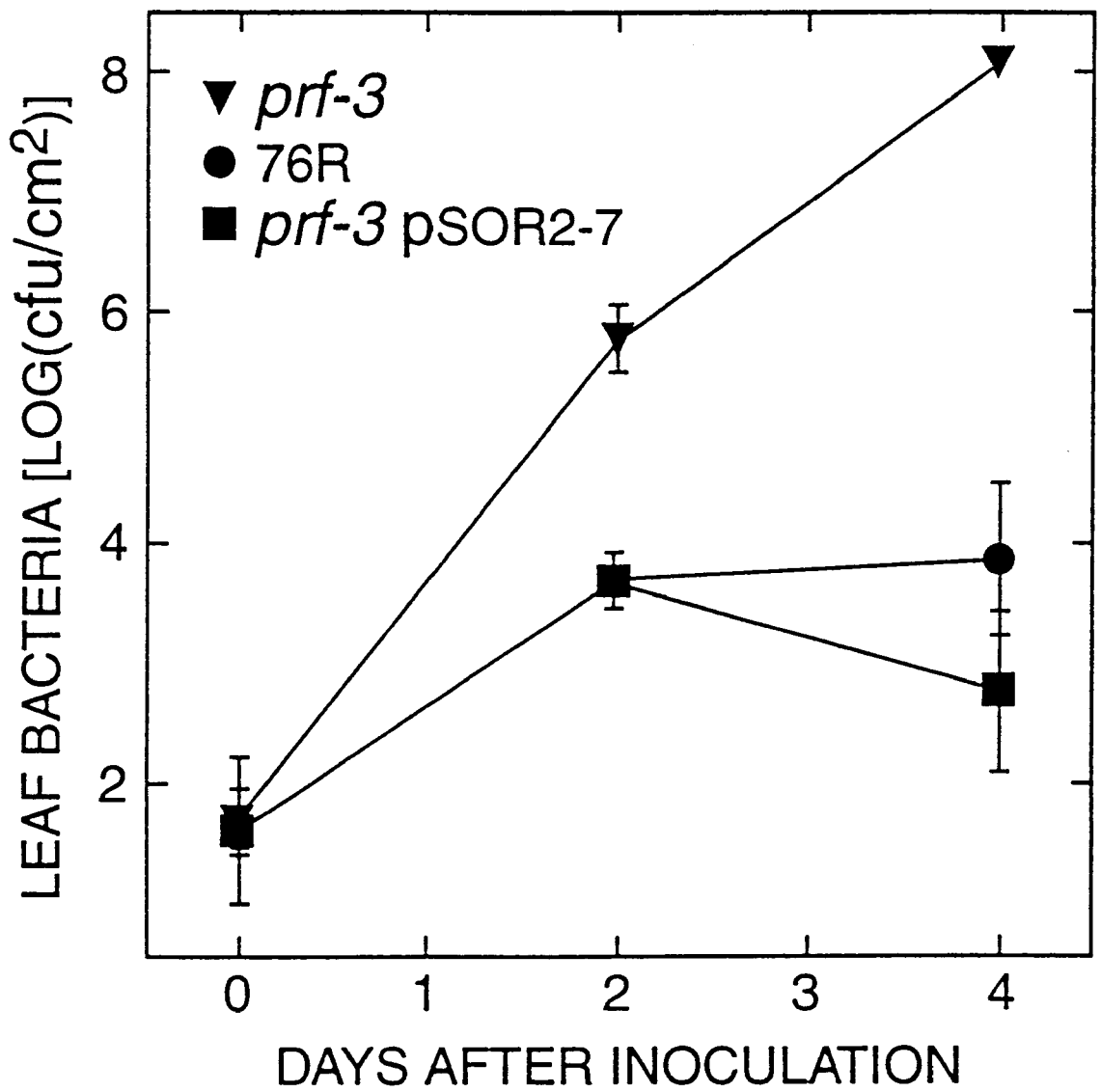

DNA gel blot analysis of the Prf locus in the prf-3 plant transformed with pSOR2-7 was also performed (FIG. 4). Genomic DNA was digested with XbaI, separated on a 0.75% agarose gel, and transferred to a Hybond N membrane. The blot was hybridized with a $^{32}$P-labeled probe corresponding to SOR2.

The results shown in FIGS. 3A–C and FIG. 4 indicate that one SOR2-containing cosmid, pSOR2-7 complemented the prf-3 mutation, while pSOR1-3 did not complement the prf-3 mutation. As expected, resistance exhibited by the transgenic plants was strictly dependent upon the presence of the avrPto gene in the pathogen, as strain T1 caused disease on the plants transformed with pSOR2-7. However, poor disease symptoms were observed on the pSOR2-7 #3 plant, which exhibits non-specific disease resistance, as discussed below.

Figure 5:
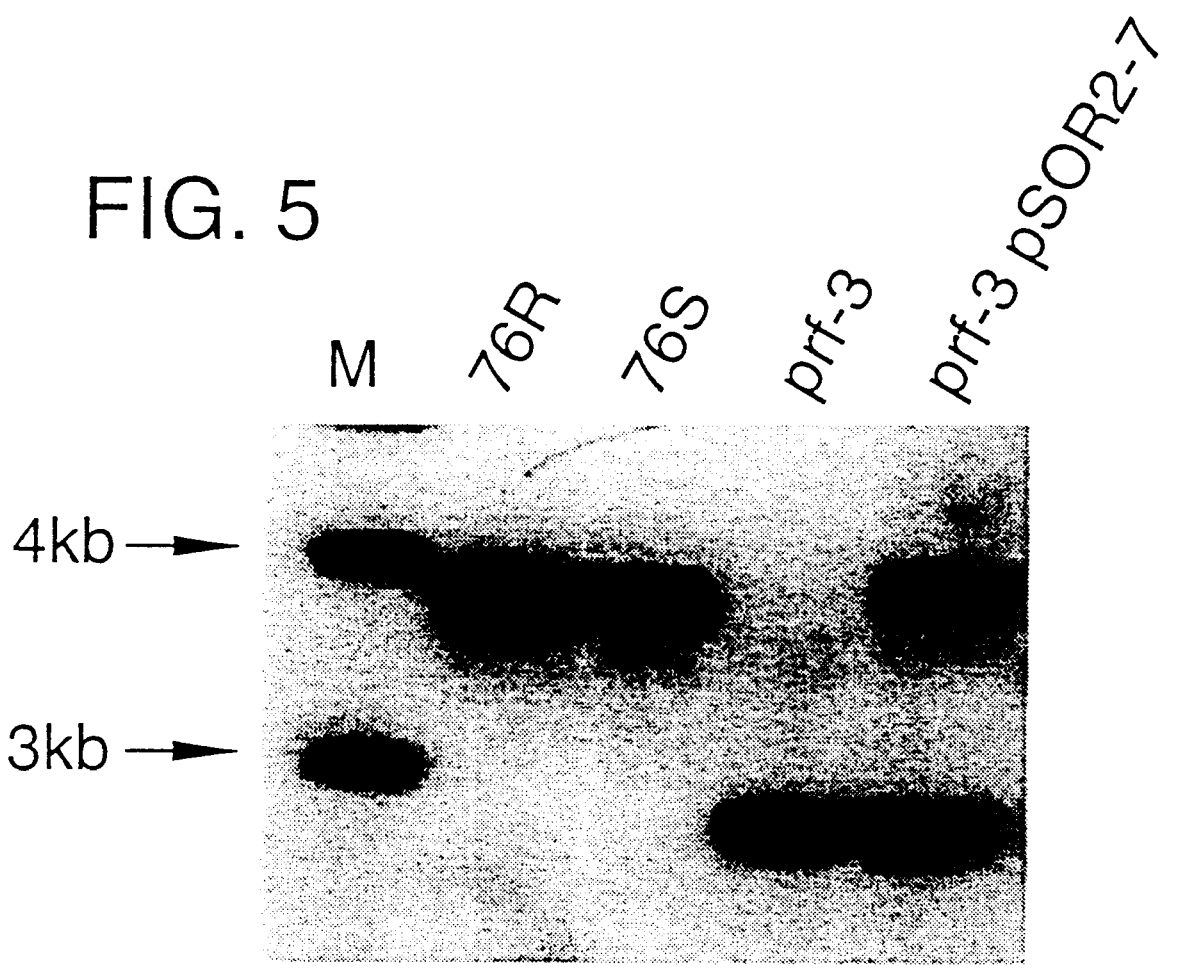

To quantify the level of resistance conferred by pSOR2-7, we monitored the kinetics of growth of T1(avrPto) bacteria in prf-3 plants transformed with pSOR2-7 and vacuum infiltrated with T1(avrPto) at a concentration of $5\times10^4$ cfu/mL. Bacterial concentrations in plant leaves were assayed after 0, 2 and 4 days. Transgenic plants containing pSOR2-7 displayed a 1000-fold reduction in bacterial growth relative to untransformed prf-3 plants (FIG. 5). This level of resistance is comparable to that observed between the wild-type resistant line 76R and the mutant line prf-3 (Salmeron et al., *Plant Cell* 6:511–520, 1994).

Figure 3D:

If pSOR2-7 contained the Prf gene, then it would also be predicted to confer Fenthion sensitivity to prf-3 tomatoes. Plants were dipped in a 4 mL/L solution of fenthion (Baytex 4; Mobay Chemicals, Kansas City, Mo.) and photographed after three days. Whereas prf-3 tomatoes and pSOR1-3 transformants showed no symptoms following Fenthion treatment, pSOR2-7 transformants developed necrotic specks at least as severe as those observed on wild-type 76R plants (FIGS. 3D and F). These results indicate that pSOR2-7 contains a gene or genes conferring both Pst (avrPto) resistance and Fenthion sensitivity in tomato.

Figure 6:
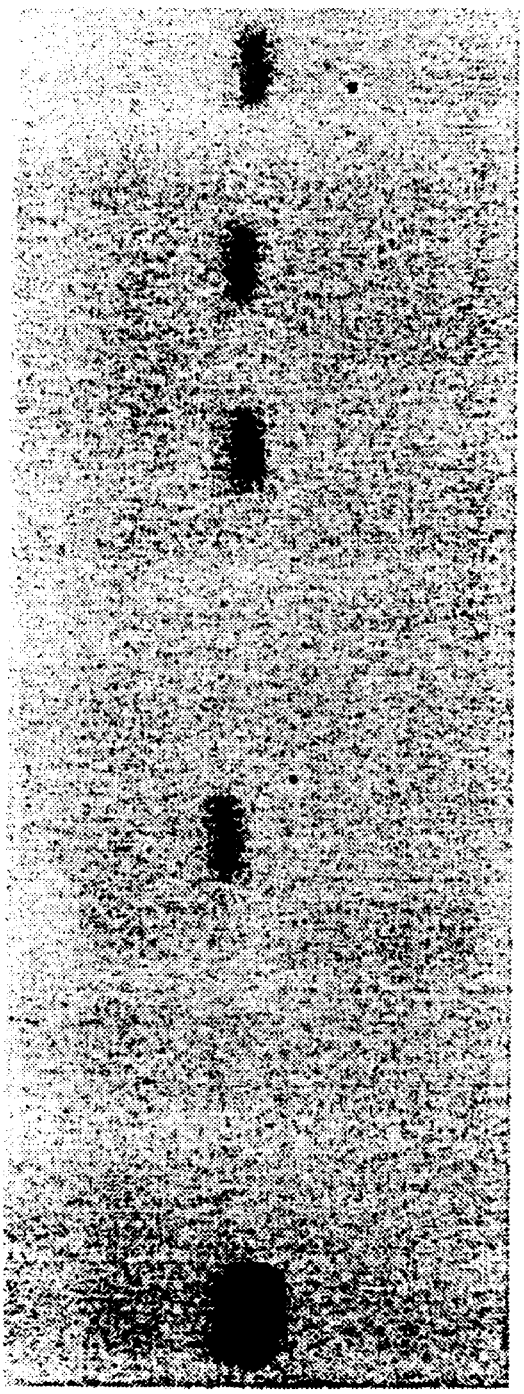

To confirm that disease resistance and Fenthion sensitivity in the transgenic plants was conferred by pSOR2-7, pSOR2-7 transformants were test-crossed to prf-3 mutant plants. Genomic DNAs from prf-3 mutant lines transformed with pSOR2-7 were digested with BgIII, separated on an 0.75% agarose gel, and transferred to a Hybond N membrane. The blots were hybridized with the 2.5 kb BgIII fragment of pCDLO4541. Plants were screened for resistance to T1(avrPto) by dipping in a solution of 10 mM $MgCl_2$, 0.05% Silwet L-77 (Union Carbide) containing $2\times10^8$ cfu/mL of T1(avrPto) and scored after five days. Progeny were analyzed for resistance to Pst strains expressing avrpto, and inheritance of transformed DNA from the vector pCDL04541. A strict correlation between the two traits was observed, indicating that the phenotypes of the transformants were conferred by the introduced cosmid DNA (FIG. 6).

Molecular Cloning of the Prf Gene. Complementation of prf-3 by pSOR2-7 and mapping of the 1-kb deletion in prf-3 to SOR2 provided strong evidence that the Prf coding region lies at least partially within SOR2. To identify genes expressed from the SOR2 region that would be candidates for the Prf gene, cDNA libraries constructed from lines 76R and VFNT Cherry were probed with SOR2. Clones of 1.1 and 1.2 kb, respectively, were the longest isolated from each library and were selected as candidate clones for the Prf gene.

Analysis of the cDNA clones indicated that the 3' ends mapped within a 3.8 kb EcoRI fragment downstream of SOR2, and that the clones were partial cDNAs each containing a single open reading frame extending completely to the 5' end of the insert. Therefore, we sequenced the entire SOR2 fragment plus 1.05 kb downstream (to a point corresponding to the ends of the cDNA clones) from both 76R and VFNT Cherry DNAs. Primers corresponding to sequences throughout SOR2 were then used to amplify the complete transcribed region of Prf from reverse-transcribed 76R mRNA using both RT-PCR and 5' RACE approaches (Experimental Procedures). The longest clone obtained from RT-PCR was 4.0 kb in length and was designated pBS-Prf, while the RACE analysis indicated a transcript of 5.7 kb in length. After adding the sequence of the Prf 3'-untranslated region as determined from sequencing the shorter cDNA clones (most of this was not incorporated into the RT-PCR products) the full length of the Prf mRNA was predicted to be 6.2 kb.

Figure 7A:
Figure 7B:
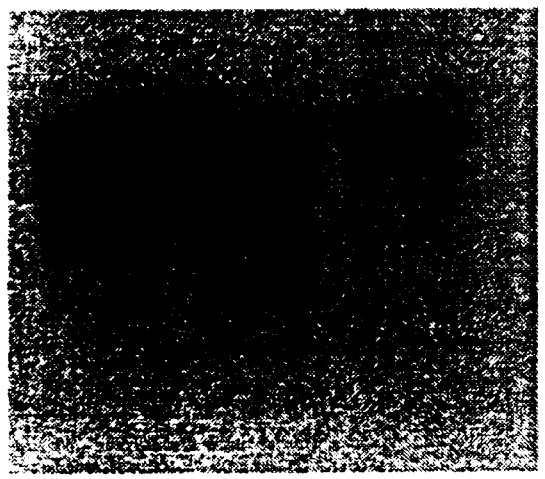

The size of the Prf mRNA was confirmed by RNA gel blot analysis. Hybridization to the radiolabeled insert of pBS-Prf reveals a mRNA of approximately 6.2 kb in wild-type 76R leaf tissue (FIG. 7, lane 1). This message is approximately 1.1 kb shorter in the prf-3 mutant (lane 2). Transformants of prf-3 containing pSOR2-7 express both sizes of mRNA (lane 3). Since RNA for this experiment was taken from uninoculated plant tissue, induction by pathogen attack is not required for expression of the Prf gene in tomato.

Nucleotide Sequence of the Prf Gene and Analysis of Mutant Alleles. The insert of the pBS-Prf cDNA along with the 5' RACE products were sequenced (FIG. 9) and found to encode a 1824 amino acid protein of 209.7 kDa (FIG. 11). Analysis of the Prf amino acid sequence shows that the protein falls into the class of resistance gene products recently identified in numerous plant species that contain putative nucleotide binding sites and leucine-rich-repeats. Of the three motifs comprising the predicted ATP/GTP binding site, the "P-loop" domain (Saraste et al., *Trends Biochem. Sci.* 15:430–434, 1990) occurs at residues 1120–1132, followed by the companion kinase domains 2 and 3a at 1195–1205 and 1224–1231, respectively. Beginning at residue 1398 is a sequence resembling leucine-rich repeat domains with approximately fourteen to eighteen imperfect copies of the leucine-rich repeat motif with a consensus sequence of LXXLXXLXXLXLXXN/ CXXLXXIPSX (FIG. 12). Other notable features of the Prf protein that are shared by other resistance gene products include a leucine zipper (Roxrigues and Park, *Mol. Cell Biol.* 13:6711–6722, 1993) spanning residues 959–994. The block of residues from 716–858 comprise two copies of a direct repeat, with 49% amino acid identity between the two copies (FIG. 13). Also present is a string of seven amino acids (1058–1064) that corresponds precisely to one half of the binding site for interleukin-8 in the mammalian interleukin-8 receptor (Hebert et al., *J. Biol. Chem.* 268:18549–18553, 1993).

Figure 8:
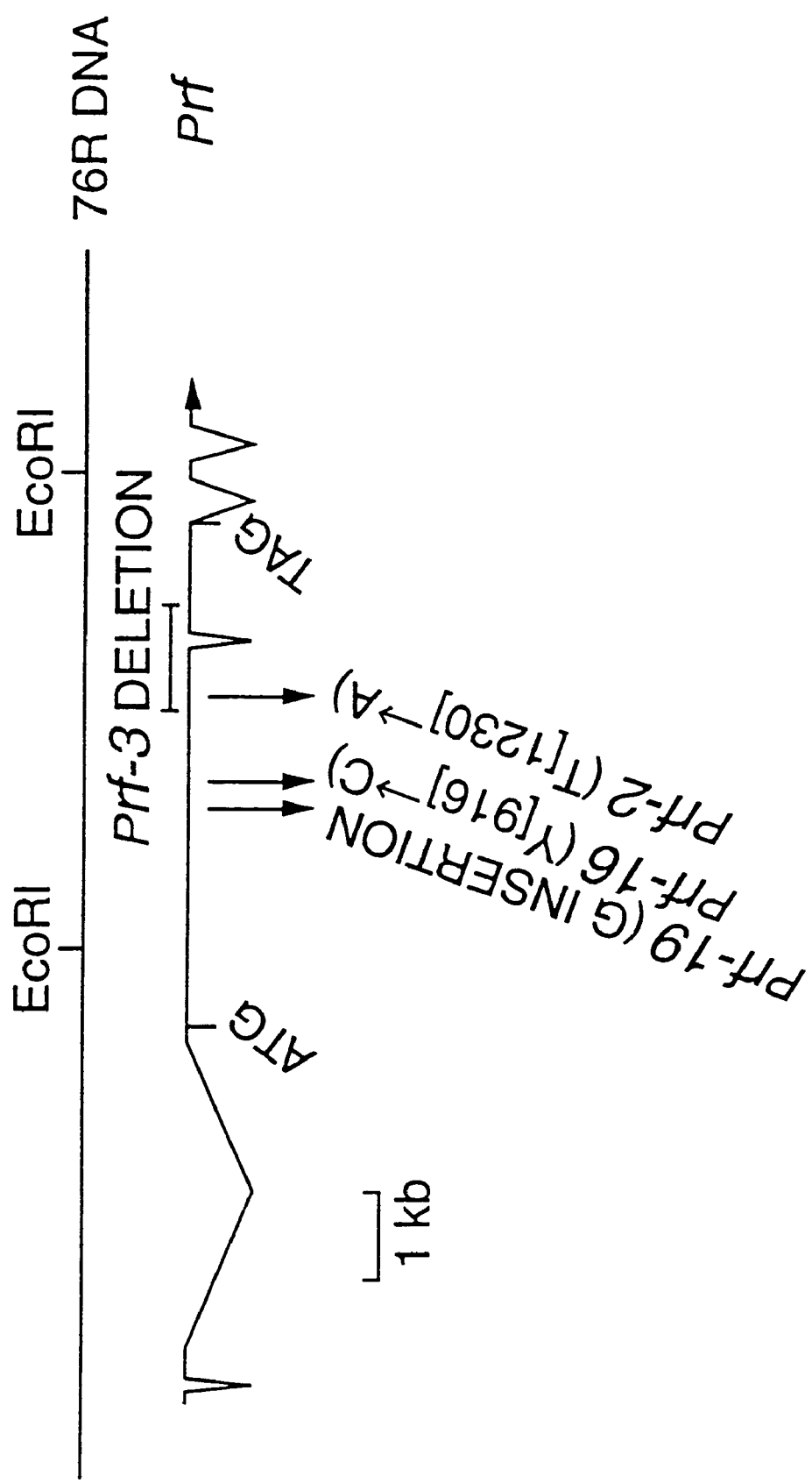
Figure 14:
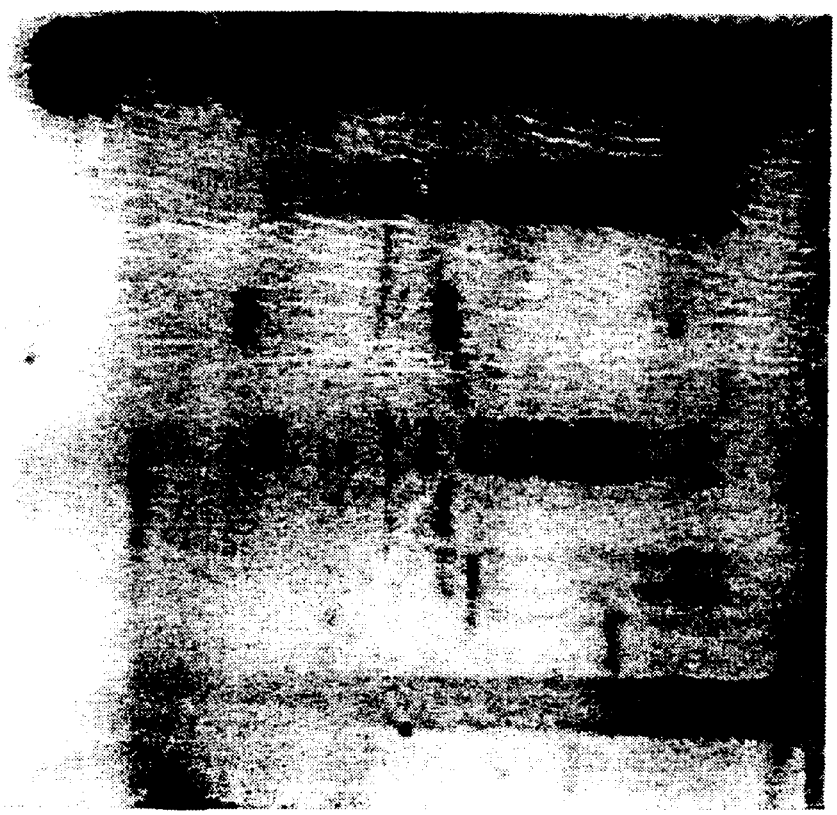
FIG. 14 shows that homologs of the Prf gene exist in numerous plant species. A fragment encoding most of the Prf leucine-rich repeat was used to probe EcoRI digests of DNAs from the indicated species.

Analysis of the genomic sequence of Prf from 76R (FIG. 10) revealed the presence of five introns. Two lie within the leader mRNA, including a large 3.6 kb intron occurring 43 nucleotides upstream of the initiator ATG. A third intron occurs between the regions encoding the P-loop and leucine-rich repeat motifs and sits between residues 1436–1437, and an additional two introns occur in the trailer mRNA (FIG. 8). A comparison of portions of the genomic Prf alleles from 76R and VFNT Cherry revealed extremely high similarity, with the encoded proteins 99.2% identical at the amino acid level across the carboxy-terminal 1128 amino acids. This is consistent with genetic evidence showing that naturally-occurring lines of tomato that do not carry a functional Pto, do carry functional copies of Prf (Salmeron et al., *Plant Cell* 6:511–520, 1994).

The mutant alleles from four prf plants were amplified from genomic DNAs using Prf-specific primers. Partial sequences were determined and compared to the wild-type gene to identify the genetic alterations in the prf mutant plants. It was confirmed that the prf-3 mutant carries a simple 1.1 kb deletion between the coding regions for the nucleotide binding site and leucine-rich-repeat motifs (FIG. 2), which deletion results in a truncated protein of approximately 1160 amino acids. Two other mutants (prf-2 and prf-16) carried single base changes which resulted in encoded proteins with single amino acid alterations relative to the wild-type sequence. The Prf-2 protein carries a Thr to Ala change at position 1230 that eliminates a residue conserved in the third portion of the nucleotide binding motif, while the Prf-16 protein carries a Tyr to Cys alteration at residue 916. Finally, the prf-19 allele was found to carry an insertion of a G residue, resulting in a frameshift. The protein encoded by prf-19 contains a wild-type sequence to amino acid 860, continuing thereafter with Gly and Ser residues before terminating (FIG. 8). These results were based on the nucleotide sequence of the SOR2 region and did not include the entire 5' end of the gene. It is possible that other mutations also lie within this region. In combination with the complementation data described above, the identification of genetic alterations in four prf mutant alleles provides additional evidence that the cDNA we have isolated corresponds to the Prf gene.

Homology of Prf to Genes in Other Plants. DNA gel blot analysis indicated that fragment(s) homologous to Prf exist in many plant species (FIG. 13). Using moderately high stringency hybridization conditions (see Experimental Procedures), most species tested showed one or two homologous fragments, while a large homologous gene family of approximately nine members was detected in tobacco. Multiple homologous bands were also detected in DNA from resistant tomato plants, indicating that Prf is a member of a gene family of approximately eight members.

Positioning Prf Relative to the Pto and Fen Genes. We were interested in determining the physical arrangement of the Prf, Pto and Fen genes within the Prf/Pto region. Cosmids containing the Pto and Fen genes were identified from the 76R contig (FIG. 1D) by PCR amplification of the respective genes from cosmid DNAs using gene-specific specific primers. Genes were assigned to individual restriction fragments by probing restricted cosmid DNAs with both the resulting PCR fragments and the cloned Pto and Fen genes. These data have recently been confirmed by preliminary sequence analysis of the Prf/Pto region. The summary of our results is depicted in FIG. 1D. The 3' end of the Prf cDNA is located approximately 500 bp from the ORF of the Fen gene and approximately 24 kb from the ORF of the Pto gene.

Broad-Spectrum Resistance to Plant Pathogens. A prf-3 mutant tomato plant was transformed with a cosmid clone that contained a wild-type copy of the Prf gene. One of the transformants, prf-3 pSOR2-7 #3 was resistant to Pst strain T1(avrPto) and sensitive to fenthion, as expected. However, in contrast to another transformant, pSOR2-7 #3 was extremely sensitive to fenthion applications.

The prf-3 pSOR2-7 #3 transgenic plant was inoculated by vacuum filtration with *Xanthomonas campestris* pv. *vesicatoria* strain p38, and bacterial concentrations in plant leaves were assayed after 0, 2, 4, and 6 days. As shown in FIG. 15, pSOR2-7 #3 was resistant not only to Pst strain T1 lacking the avrPto gene but also to *Xanthomonas campestris* pv. *vesicatoria* strain p38. These results suggest that plants expressing the Prf transgene may be resistant to a wide variety of plant pathogens, including bacteria, viruses, fungi, and nematodes.

Additional characterization of pSOR2-7 #3 suggests that this plant contains more than one copy of the T-DNA. High-level expression of the Prf gene is likely responsible for the broad-spectrum resistance to phytopathogens observed in plants expressing the Prf transgene.

Discussion

The cloning of plant disease resistance genes has demonstrated that diverse plant species utilize proteins with a shared organization of structural motifs for defense against a wide range of pathogens (Staskawicz et al., *Science* 268:661–667, 1995). These motifs include a "P-loop" region that serves as part of a nucleotide triphosphate binding site, and a "leucine-rich repeat" (LRR) thought to form a site for interaction with other proteins (Kobe and Deisenhofer, *Trends Biochem. Sci.* 19:415–421, 1994). LRR-type plant disease resistance gene products form two subclasses (Jones et al., *Science* 266:789–792, 1994). Proteins in the first subclass contain the P-loop in the N-terminal half of the protein and the LRR near the carboxyl terminus. In these proteins the repeats within the LRR (SEQ ID NO: 4) tend to be poorly conserved, and most closely match the repeat consensus found in yeast adenylate cyclase (Kataoka et al., *Cell* 43:493–505, 1985). These proteins do not contain signal sequences and thus may localize to the plant cytoplasm. The second subclass of resistance gene products lack an apparent nucleotide binding site but contain a signal sequence that may function to target the protein to the cytoplasmic membrane. The repeats within the LRR, found in the amino-terminal portion of the protein, are well-conserved and most closely resemble those found in plant polygalacturonase inhibitor proteins (Stotz et al., *Plant Mol. Biol.* 25:607–617, 1994).

Prf falls into the first protein subclass. Two other proteins that function in resistance to strains of *Pseudomonas syringae,* the Arabidopsis RPS2 and RPM1 proteins (Bent et al., *Science* 265:1856– 1860, 1994; Grant et al., *Science* 269:843–846, 1995; Mindrinos et al., *Cell* 78:1089–1099, 1994), are also members of the first protein subclass, perhaps reflecting a common mechanism by which the elicitors produced under control of the corresponding avirulence genes are presented or perceived.

Construction of chimeras between different cloned resistance genes, and analysis of naturally-occurring and engineered mutant alleles can be used, for example, to identify domains that provide the specificity of recognition. For the Cf-9 and Prf genes, the availability of elicitors or elicitor-like molecules (Fenthion) (Carland and Staskawicz, *Mol. Gen. Genet.* 239:17–27, 1993; van Kan et al., *Mol. Plant-Microbe Interact.* 4:52–59, 1991) facilitates these and other studies addressing the roles of resistance gene products in ligand binding and signal transduction.

In tomato, the Pto and Fen kinases are required for transduction of pathogen elicitor and Fenthion signals to induce, in the case of Pto, disease resistance with associated hypersensitivity (Martin et al., *Science* 262:1432–1436, 1993), and in the case of Fen, a hypersensitive-like necrosis (Martin et al., *Plant Cell* 6:1543–1552, 1994; Rommens et al., *Plant Cell* 7:249–257, 1995). Since Prf is required for both these phenotypes (Salmeron et al., *Plant Cell* 6:511–520, 1994), the Prf protein must be a component common in the signaling pathways containing the Pto and Fen kinases. By analogy to some mammalian hormone receptors (Braun et al., *EMBO J.* 10:1885–1890, 1991) and to the Drosophila Toll protein (Hashimoto et al., *Cell* 52, 269–279, 1988), to which the tobacco N resistance gene product is similar (Whitham et al., *Cell* 78:1101–1115, 1994), Prf may function as a receptor that binds the pathogen elicitor or Fenthion and transduces the signal directly to either of the kinases, which may be membrane-associated. Alternatively, other proteins may serve as intermediaries between Prf and Pto/Fen or Prf may lie downstream of Pto and Fen in their respective signaling pathways. It has been shown that the Pti1 protein kinase acts downstream of Pto (Zhou et al., *Cell* 83:925–935, 1995). If Prf is a downstream component in the tomato resistance pathway, it is likely that Prf is the recipient of a signal transduced by one or more protein kinase cascades.

The pathway involved in resistance of rice to bacterial blight, in which the Xa21 gene confers resistance to *Xanthomonas oryzae*, is the only pathway other than the Prf/Pto pathway demonstrated to involve both an LRR-containing protein and a protein kinase (Song et al., *Science* 270:1804–1806, 1995). Remarkably, the LRR and kinase domains both reside on the Xa21 protein (Song et al., *Science* 270:1804–1806, 1995). The Prf and Pto proteins may be derived from an ancestral tomato resistance factor in which the LRR and protein kinase domains were fused. The physical proximity between the Prf and Pto genes suggests the possibility of such an evolutionary relationship.

Although the Prf/Pto and Xa21 pathways may be unique in involving protein kinases in disease resistance signaling, it is more likely that the corresponding protein kinases in other systems have not yet been identified, perhaps due to functional redundancy. Most mutations at the Pto locus are weak alleles that cause only partial susceptibility to Pst strains that express avrPto. Mutations at Prf completely abolish resistance (Salmeron et al., *Plant Cell* 6:511–520, 1994). This may reflect a functional redundancy among members of the Pto gene family in wild-type plants. Homologs of Pto exist in many plant species (Martin et al., *Science* 262:1432–1436, 1993). If these homologs function in disease resistance pathways in their respective hosts, they may also exist as gene families with multiple functional members.

Figure 1:
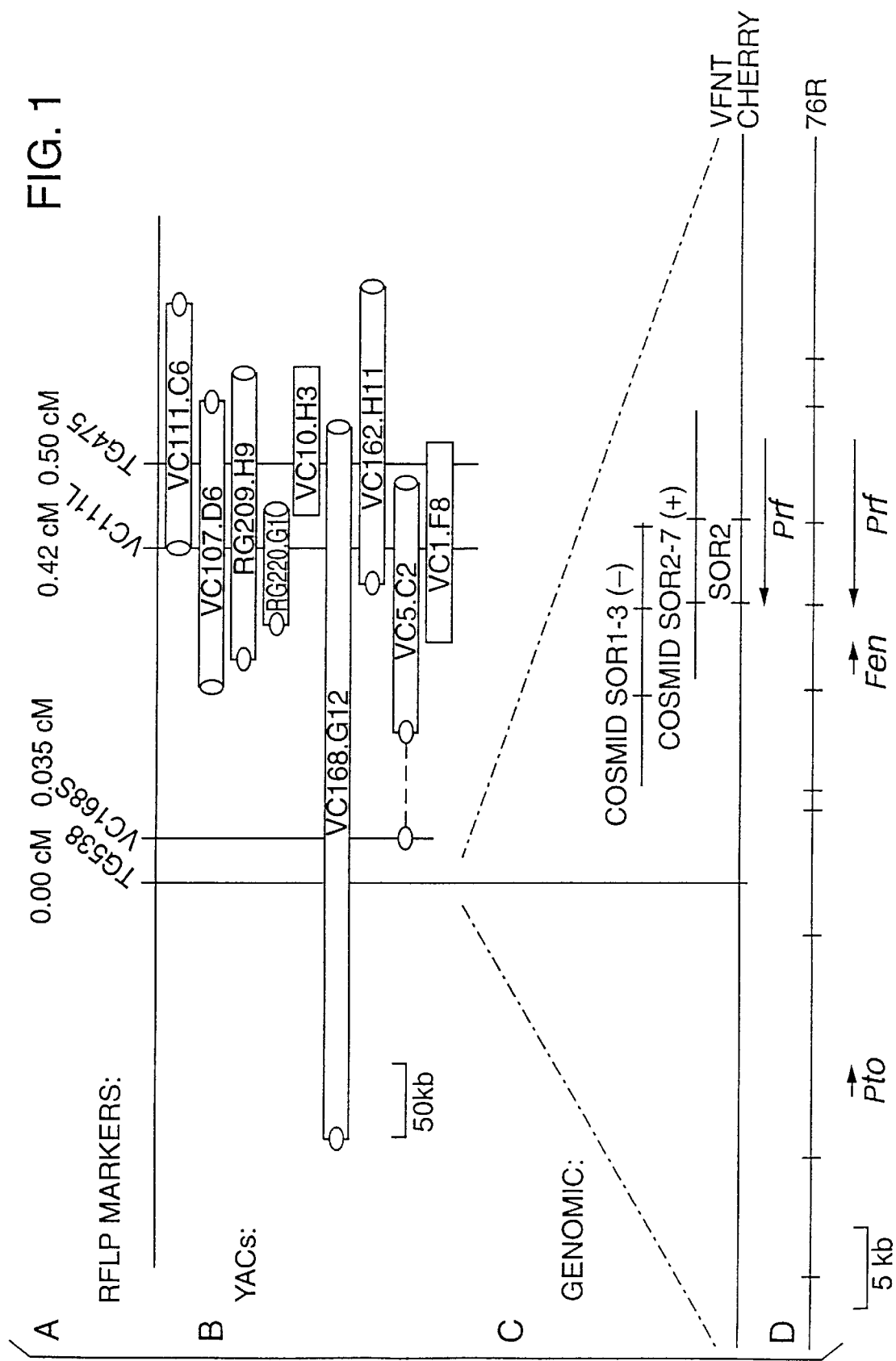
Figure 2:
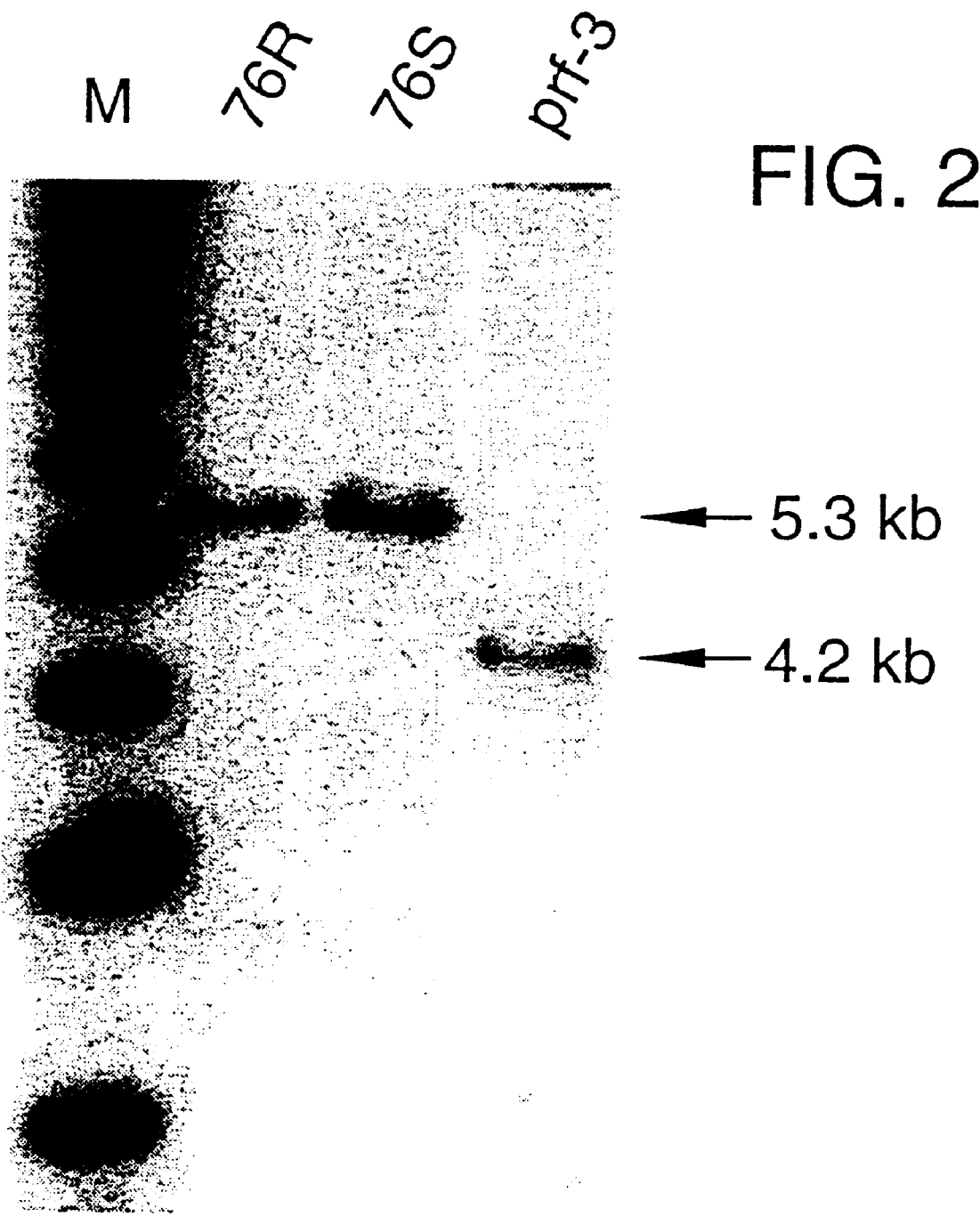

The Prf gene is located within the Pto gene cluster, immediately adjacent to the Fen gene (FIG. 1). The proximity of Prf to Pto and Fen, genes with which Prf cooperates in disease resistance signaling, is reminiscent of Brassica species in which two genes that control self-incompatibility, SLG and SRK, lie within a distance of 200 kb (Boyes and Nasrallah, *Mol. Gen. Genet.* 236:369–373, 1993). By further analogy, the SRK gene encodes a receptor kinase proposed to interact with the SLG-encoded glycoprotein in initiating the self-incompatibility reaction (Stein et al., *Proc. Natl. Acad. Sci. USA* 88:8816–8820, 1991), which, like the plant defense response, involves restricting the growth of an invading organism (in this case, the pollen tube).

The potential for Prf to couple with distinct kinases in transduction of different signal molecules may be important in lending the flexibility required by the host to counteract ongoing pathogen evolution. The avrPto gene appears to be dispensable for growth of Pst in cell culture and in infected plants (Ronald et al., *J. Bacteriol.* 174:1604–1611, 1992). Pst strains lacking avrPto are known to arise in fields heavily planted with Pto cultivars. It would be advantageous for the host to be able to recognize altered forms of pathogen elicitors, which may be most easily achieved through differential coupling of distinct but related signaling components. The occurrence of Pto and Prf as members of multigene families may allow for additional diversity through recombinational processes (Sudapak et al., *Genetics* 133:119–125, 1993) that could prove advantageous to tomato lines in the face of an ever-changing Pst population.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method of obtaining an isolated Prf nucleic acid sequence of a plant species comprising:

contacting a nucleic acid of the plant species with a probe or primer under stringent hybridization conditions comprising washing conditions of 65° C., 0.5×SSC and 0.5% SDS for 1 hour to cause the probe or primer to hybridize to the nucleic acid of the plant species, wherein the probe or primer comprises at least 15 contiguous nucleotides of SEQ ID NO: 1, or SEQ ID NO: 3, and isolating the nucleic acid of the plant species to which the probe hybridizes.

2. An isolated nucleic acid comprising at least 1 contiguous nucleotides of a sequence that hybridizes to SEQ ID NO:1 or SEQ ID NO:3, under stringent hybridization conditions comprising washing conditions of 65° C., 0.5×SSC and 0.5% SDS for 1 hour.

3. The isolated nucleic acid of claim 2, wherein the nucleic acid sequence hybridizes specifically to SEQ ID NO: 1 or SEQ ID NO: 3.

4. The isolated nucleic acid of claim 2, wherein the nucleic acid comprises at least 20 contiguous nucleotides.

5. The oligonucleotide according to claim 4, wherein the nucleic acid comprises at least 30 contiguous nucleotides.

6. The method of claim 1, wherein the isolated Prf sequence is selected from the group consisting of SEQ ID NO: 1 and SEQ ID NO: 3.

7. The method of claim 1, wherein the probe or primer comprises at least 15 nucleotides of nucleotides 3150–4494 of SEQ ID NO: 3.

8. The method of claim 1, wherein the probe comprises the nucleotide sequence of SEQ ID NO: 7, 8, 9, 10, 11, 12, 13, 14, 15 or 16.

9. A method of obtaining a Prf nucleic acid of a plant species comprising:

amplifying a plant nucleic acid sequence using two or more oligonucleotide primers comprising at least 15 contiguous nucleotides of SEQ ID NO: 1 or SEQ ID NO: 3; and determining whether an amplified sequence is present, wherein the presence of an amplified nucleic acid sequence demonstrates the presence of the Prf nucleic acid sequence.

10. The method of claim 9, wherein the amplifying of the plant nucleic acid sequence comprises polymerase chain reaction amplification.

11. The method of claim 9, wherein at least one of the oligonucleotide primers comprises a sequence as set forth in SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16.

12. The method of claim 1, wherein the stringent hybridization conditions comprise hybridization at 65° C. and 6×SSC.

* * * * *

UNITED STATES PATENT AND TRADEMARK OFFICE
CERTIFICATE OF CORRECTION

PATENT NO. : 6,245,510 B1
DATED : June 12, 2001
INVENTOR(S) : Staskawicz et al.

It is certified that error appears in the above-identified patent and that said Letters Patent is hereby corrected as shown below:

<u>Title page,</u>
Item [56], OTHER PUBLICATIONS, "Shah D.M., et al., "Resistance to Diseases and insects in Transgenic Plants: Progress and Applications to Agriculture," *Trends in Biotechnology,* vol. 13, No. 9, pp. 363-368" should read -- Shah D.M., et al., "Resistance to Diseases and insects in Transgenic Plants: Progress and Applications to Agriculture," *Trends in Biotechnology,* vol. 13, no. 9, pp. 362-368 --.

<u>Column 4,</u>
Line 33, "+" should read -- ± --.
Line 55, "10 g" should read -- 10 ug --.

<u>Column 7,</u>
Line 40, "Prr" should read -- Prf --.

<u>Column 8,</u>
Line 46, "such-as" should read -- such as --.

<u>Column 9,</u>
Line 31, "Oncoding" should read -- encoding --.

<u>Column 12,</u>
Line 48, "Homolony" should read -- Homology --.

<u>Column 13,</u>
Line 45, "etal." should read -- et al. --.

<u>Column 22,</u>
Lines 3-4, "gene-specific specific primers" should read -- gene-specific primers --.

UNITED STATES PATENT AND TRADEMARK OFFICE
CERTIFICATE OF CORRECTION

PATENT NO.    : 6,245,510 B1
DATED         : June 12, 2001
INVENTOR(S)   : Staskawicz et al.

It is certified that error appears in the above-identified patent and that said Letters Patent is hereby corrected as shown below:

Column 69,
Line 28, "1 contiguous" should read -- 15 contiguous --.

Signed and Sealed this

Second Day of September, 2003

JAMES E. ROGAN
*Director of the United States Patent and Trademark Office*

SEQUENCE LISTING

```
<160> NUMBER OF SEQ ID NOS:  17

<210> SEQ ID NO 1
<211> LENGTH: 10968
<212> TYPE: DNA
<213> ORGANISM: Lycopersicon esculentum
<220> FEATURE:
<221> NAME/KEY: CDS
<222> LOCATION: (3879)..(8186)
```

-continued

```
<221> NAME/KEY: CDS
<222> LOCATION: (8300)..(9466)

<400> SEQUENCE: 1
```

| | | | | | |
|---|---|---|---|---|---|
| aatattataa | ctgttggaaa | atgaactcaa | ccattcatca | attatctcaa | gaagaagacc | 60 |
| agtatgaact | ctaagcttat | gggtaagtaa | tttctctctg | attttcataa | aatgaaagaa | 120 |
| gaaattgcaa | gtatttacct | tcatttgctt | tgttaattgc | aggcagctag | gacttaaaaa | 180 |
| aaaatcattg | aagaaaagag | ttttctgtta | gatttcaacc | atcaaacact | aaacgaaaag | 240 |
| tagtaagttg | tttattttcc | tctctcattt | actcaatatt | cttaactata | aactaattgc | 300 |
| atcttataac | acagatctgc | atccgttttt | gttttaaaat | tttgagaaaa | tggttaaagc | 360 |
| cccctccaat | tacaagctcg | tacttcacgg | gtgtcctatc | actttcctga | actgtttaat | 420 |
| gcaagaatta | ttacactcct | aaaacgtcat | aaccacatct | atgctaatga | gtgagactca | 480 |
| ctctttgcag | aaattttatt | taaaactttt | tttaattcat | tttccttttt | gatttattat | 540 |
| ttaaaaaaca | atttaatatc | aaaagttaa | agtttatgaa | tgtatttttgt | atcttcaatt | 600 |
| tgaaacatat | tgttgataac | atagatggtt | gttaattatt | tgaagttgaa | tatattgaat | 660 |
| ttatgaatgt | gatattcaaa | ttaaagagac | gcccgaaatt | ttatggaaat | cgataagctt | 720 |
| gaataacaa | tttgacttgc | cacaaatgac | caccattttg | agtgggtaat | atatcaaaaa | 780 |
| gttggaaaca | ctgagagaag | cttatatcta | aaatttaagg | aaatctggag | atgatttagg | 840 |
| gtggttttgc | atcaaatttc | aaagcaatgg | aatgaagaag | atgaagaaca | taactaact | 900 |
| tttcagatgc | gtaggaaaag | gaaaagttat | taaaattagt | catggatttg | ttgggtatta | 960 |
| aatataagat | aaaaatttat | cttaatattc | aaagtttatt | gaagaaaatc | atttgggtgt | 1020 |
| tcatatattt | ttttaaaaaa | aaattggtgc | atatatcaaa | gattttttat | atacagttct | 1080 |
| tgattttgga | gagtaatgga | tgaaattgct | ataaataatt | ttggtgtatc | aattaaagta | 1140 |
| gtgataggaa | tgatttcaag | atggtgaaga | actttggtgg | tgccatattt | atgttgtgaa | 1200 |
| gttgaaagaa | aattaataac | taaaatacaa | catttattat | ttgtgttggt | tcaaactcta | 1260 |
| ttaccgagag | tgagatacac | tcactatacc | acaatgtgcc | acgtaagcgt | ctagggagta | 1320 |
| aattattttt | agttttaaat | aattcaggga | gtgataggac | atccgtgaag | ttgaagtatg | 1380 |
| tagttgagat | ttcgggtata | gattgggggg | ctttagacca | ttggatttga | tctaagtatc | 1440 |
| tatttcaatt | tatatgatgt | aatttgactt | gacacgaaat | ttaagacgaa | gaaaaaaga | 1500 |
| ctaagtactt | ccactgtcaa | acaatatttg | tccactacta | ttttacacaa | ttagtaagaa | 1560 |
| actatacct | ttgaatttaa | taaatacaat | ctcttgaaaa | atgtaatagt | gaatgacta | 1620 |
| taattaatga | taaaagtaca | tcaggaacta | agtgtaaaat | tatcaattca | ttttataaag | 1680 |
| tagacaagta | ttgttggaca | tcctaaaata | gtatagttga | caactattat | tgaatagagg | 1740 |
| gagtatctct | gtgtgactat | acatttttt | aaaattaaaa | ttactaaata | tagagaatta | 1800 |
| aaaatgtgtt | atttccccct | tttagaatg | attaaaaaga | aatccgagtc | ttattttaga | 1860 |
| gagatttaaa | ttgtttcact | aaatttttat | caagttaaaa | atgcttattt | tagagagttg | 1920 |
| agttatttgg | ccatgttttt | agaaaaaaaa | agtgattgtg | agtattgaga | gaaactattt | 1980 |
| ttcaatagtt | acaaaaaaat | ttggtttagt | ttttactgtg | tttttcctcc | atggtttcca | 2040 |
| acacttgact | ctaggcttct | gtgctatttc | gaagcactct | atagtctgta | tcaggggcgg | 2100 |
| agccagcttg | aatcccttcg | gcgaaaaata | taactatttc | tatatcgtaa | aaattattct | 2160 |
| ttatgtattt | atagtagata | tttaaccccc | ctcggttagt | ccgtgtgttt | agttcttcag | 2220 |

```
attttgaacc ccctaaatc cgccactggt ctatacgctt gatgtcaact tggtaacctc    2280
cattatcaaa ggtgtcttct tgaactaaga taaccaatgc ttcaaagtga agatcacata    2340
ttacaccatt gattatatga tcattaggtg aaactaagcc accccgatt tctagatttt     2400 gatacattcc ctcaagcaca aagacacaca caatcatgca taagaagaaa atagtagtga    2460
aaagttcatg attacattta tgcccgatac ttctataacc tactgcaaat tatacacttt    2520
tatggtatag gctatagcca agtatcatga taaacaacaa atactgaagt tcgcaacaac    2580
cacaataagt tggttaggag gaagataata atcactaaga ctataactgt cgtcgaactt    2640
ccaaatgtaa gcaactttat gataagctag tcatcacaac attcaataaa gatcaatatc    2700
ccaagagagt tagtatgcaa ttggattaga agacgaacag tatctgataa aataaaggag    2760
cctataaatt caaaagacaa tgcttgtatg ctcatattat ccctattacc tttttgcgct    2820
aaaacacact tccaactcaa gttgttggat ataattcatt ttgcaagatt cacaagaaat    2880
gtcaattttg agctaccaaa ctagtccatc atctcgttgg ttatcttcca tttatcaaac    2940
aaagaatcac atccccccgga tcaaatacaa atcaaacccc aaacatctct aagagctcca    3000
acaatcactt cacatagcat ctcaaatggc aagttttaag aataaacaca agtcatcaca    3060
tagttgctgc aacaagtctt aagatcgagg gacttaacct tcatagcttt agaaagctca    3120
agcataagtg tcaaccattc atacaataca atcttgaacg tagaatatat taaatagtaa    3180
atcctaatgt atcccaagat agtgcctcca aacttcttac ttccttgtag tctttcctgt    3240
gatgaacctt gataatgagt ctgtaagttt tggttccaaa actgtacgtt cttattcatc    3300
tgtagtggta caaatttata gtagagagat ataaactagc aatcagattt ccttaattca    3360
aggagatttg agcatcaagg gaagctctaa tttcctaaac tatttgatag catattaaag    3420
ctaattttgt cagatctatt tatatcctat aaaatcagat ctgatcctag ccagatattt    3480
acaaatcaac actcccctc aagttgacat gtaagtattt atcatgccta acttgcttac     3540
aagaatttca cattttggtt caaacaagcc ttttatgaaa atatccacaa tttgctggtc    3600
tgttgggacg aaagacatac acacacttca tttttcaatc ttcgttttta tgaagtttct    3660
atcatgttga actggattgg gaacaatact tatggcggct ttgttgtcac attacaactt    3720
tattggtaga gaaaattttc agtccatctt cttgagccag ttcatttcgt agatctgtat    3780
tcaactttag caatgctaca agcgacattc ggacgatact gattcattac ttgcaggatt    3840
tattaacaat cacaggaaac ttaaaaggtg aagggag atg gcc aag gag tgt cgc    3896
                                       Met Ala Lys Glu Cys Arg
                                         1               5 gat gca ata ggt act ata aac ctt gtg aag ggc cag cat tta gac aga     3944
Asp Ala Ile Gly Thr Ile Asn Leu Val Lys Gly Gln His Leu Asp Arg
         10                  15                  20 agg acc act aat caa ttg gag gat gct ata aag cac cta aca cat gtt     3992
Arg Thr Thr Asn Gln Leu Glu Asp Ala Ile Lys His Leu Thr His Val
     25                  30                  35 gct gta ttt ctc aca aat ctg gag aag cgt cac cct gct aat gga ata     4040
Ala Val Phe Leu Thr Asn Leu Glu Lys Arg His Pro Ala Asn Gly Ile
 40                  45                  50 tct ata cat ctt agg cct cta ttt tta gaa gct cat gat ggc ttt tct     4088
Ser Ile His Leu Arg Pro Leu Phe Leu Glu Ala His Asp Gly Phe Ser
55                  60                  65                  70 ctg atg tgt tct cat cct cct cgt tct cag ttt acc gtt aaa ctg gat    4136
Leu Met Cys Ser His Pro Pro Arg Ser Gln Phe Thr Val Lys Leu Asp
             75                  80                  85 aac att gct gag aaa ttc aaa tct tca aag gcg tca aga tca aca agg    4184
```

```
Asn Ile Ala Glu Lys Phe Lys Ser Ser Lys Ala Ser Arg Ser Thr Arg
             90                  95                 100 caa gtg atc cca gag ctg ctg caa ata att gaa ccc gag aat att gct    4232
Gln Val Ile Pro Glu Leu Leu Gln Ile Ile Glu Pro Glu Asn Ile Ala
        105                 110                 115 aag cga atc aaa gct tca aag cca tca aga tca tct agc cca atc act    4280
Lys Arg Ile Lys Ala Ser Lys Pro Ser Arg Ser Ser Ser Pro Ile Thr
    120                 125                 130 gtg gat atg gtg ggg ttt atc gaa tcc ttg ctt ggt tct gtt cat cgt    4328
Val Asp Met Val Gly Phe Ile Glu Ser Leu Leu Gly Ser Val His Arg
135                 140                 145                 150 gca ttg ttc ttt atc agt gca ggg cct cct gtg tct atg ctt gac aag    4376
Ala Leu Phe Phe Ile Ser Ala Gly Pro Pro Val Ser Met Leu Asp Lys
                155                 160                 165 aag ctt cga cat cta caa gtc ttc ttt aga cta att tca aag cgg ggc    4424
Lys Leu Arg His Leu Gln Val Phe Phe Arg Leu Ile Ser Lys Arg Gly
            170                 175                 180 att gag cat gag agt atg aag gat ctc ttc tac cat gtt gag gat gta    4472
Ile Glu His Glu Ser Met Lys Asp Leu Phe Tyr His Val Glu Asp Val
        185                 190                 195 gct tac act gca gca caa cta tgt gtc ttg ggg tcg agc tgc cat atg    4520
Ala Tyr Thr Ala Ala Gln Leu Cys Val Leu Gly Ser Ser Cys His Met
    200                 205                 210 gat gac gag ttc tct aaa ttt ctg gaa agg ata agt cgt cct ttt agc    4568
Asp Asp Glu Phe Ser Lys Phe Leu Glu Arg Ile Ser Arg Pro Phe Ser
215                 220                 225                 230 cca gga ttg agg cag gtt tat ctc aat gcc ttg ata ggg tta aat tca    4616
Pro Gly Leu Arg Gln Val Tyr Leu Asn Ala Leu Ile Gly Leu Asn Ser
                235                 240                 245 tca aga tca aag act aca atg aat gcc aaa tat atg ctt gat ttt gtt    4664
Ser Arg Ser Lys Thr Thr Met Asn Ala Lys Tyr Met Leu Asp Phe Val
            250                 255                 260 agt gct ctc caa gat gat ctg aga cta aga tgt gat aat cga att cga    4712
Ser Ala Leu Gln Asp Asp Leu Arg Leu Arg Cys Asp Asn Arg Ile Arg
        265                 270                 275 tgg ctc caa cga gga ctt tct tac ctt tgt cga ttc ctc agg gac ata    4760
Trp Leu Gln Arg Gly Leu Ser Tyr Leu Cys Arg Phe Leu Arg Asp Ile
    280                 285                 290 gaa tct tat cct gtt tca cat cga caa ctg att tct ctt caa ttg aat    4808
Glu Ser Tyr Pro Val Ser His Arg Gln Leu Ile Ser Leu Gln Leu Asn
295                 300                 305                 310 atg gaa gat ctg gct att ggg tct gca aat gcc atc tac tcc tat gat    4856
Met Glu Asp Leu Ala Ile Gly Ser Ala Asn Ala Ile Tyr Ser Tyr Asp
                315                 320                 325 gag gat atg gat aag act agt gaa ata gac cat gag ctt ttt cat ttg    4904
Glu Asp Met Asp Lys Thr Ser Glu Ile Asp His Glu Leu Phe His Leu
            330                 335                 340 caa atg aag ttt aat tat gtt aaa gta gag gtt gat ctg att cgt cta    4952
Gln Met Lys Phe Asn Tyr Val Lys Val Glu Val Asp Leu Ile Arg Leu
        345                 350                 355 caa aac att caa ggc acc ata ata gtt cct atg aaa gat ctg att gac    5000
Gln Asn Ile Gln Gly Thr Ile Ile Val Pro Met Lys Asp Leu Ile Asp
    360                 365                 370 tat gtt tgg gaa gag ctg atg ttc ttt aga agt tat ttc atg gat gca    5048
Tyr Val Trp Glu Glu Leu Met Phe Phe Arg Ser Tyr Phe Met Asp Ala
375                 380                 385                 390 ttc gac cag ttt aaa gag cag acc agg ata act gtt att ttg aac tat    5096
Phe Asp Gln Phe Lys Glu Gln Thr Arg Ile Thr Val Ile Leu Asn Tyr
                395                 400                 405
```

-continued

| | | |
|---|---|---|
| att cag tct gca gtt agt caa gca tgg tca gtc tgt gat tct ctt tgt<br>Ile Gln Ser Ala Val Ser Gln Ala Trp Ser Val Cys Asp Ser Leu Cys<br>410                        415                  420 | 5144 |
| cat gac ttg aat caa aat gac ttg gcc agg gaa att aat tgc ttg cat<br>His Asp Leu Asn Gln Asn Asp Leu Ala Arg Glu Ile Asn Cys Leu His<br>        425                      430                      435 | 5192 |
| ttt caa ttg ctt ctt aag ttc aag ttt atc aag gtc gct att aga cag<br>Phe Gln Leu Leu Leu Lys Phe Lys Phe Ile Lys Val Ala Ile Arg Gln<br>440                        445                  450 | 5240 |
| atg tgt ccc agc att tct gca tca tca aca cca gac cat cca atg ata<br>Met Cys Pro Ser Ile Ser Ala Ser Ser Thr Pro Asp His Pro Met Ile<br>455                        460                  465                  470 | 5288 |
| gat ctg ctg aac ttt ctt ccc atg aac ttt gag gcc att gat tcc tat<br>Asp Leu Leu Asn Phe Leu Pro Met Asn Phe Glu Ala Ile Asp Ser Tyr<br>                  475                      480                  485 | 5336 |
| tcc agc atg cta aaa gcc tcc tgt cca tct tcc tca cat cgt cct aat<br>Ser Ser Met Leu Lys Ala Ser Cys Pro Ser Ser Ser His Arg Pro Asn<br>            490                      495                      500 | 5384 |
| agg gat gcg gaa tcc ccc aat aca tca ttc tta tgt ggt ccc aat aca<br>Arg Asp Ala Glu Ser Pro Asn Thr Ser Phe Leu Cys Gly Pro Asn Thr<br>505                        510                  515 | 5432 |
| gat gtg tac tcc ttc tat tca tca tcc tca cgt att ccc aag atg gat<br>Asp Val Tyr Ser Phe Tyr Ser Ser Ser Ser Arg Ile Pro Lys Met Asp<br>520                        525                  530 | 5480 |
| gag ata ttg aag agg ttt cat gaa tat att ctt gtc aat ctg cta cgg<br>Glu Ile Leu Lys Arg Phe His Glu Tyr Ile Leu Val Asn Leu Leu Arg<br>535                        540                  545                  550 | 5528 |
| aag gat gaa acc aat ttg aca ttt act att gca gat gag gtc aaa aag<br>Lys Asp Glu Thr Asn Leu Thr Phe Thr Ile Ala Asp Glu Val Lys Lys<br>                  555                      560                  565 | 5576 |
| ttt tat gat ggg ttg ttg ctc atg gtt aca tat ctt att gaa cct cca<br>Phe Tyr Asp Gly Leu Leu Leu Met Val Thr Tyr Leu Ile Glu Pro Pro<br>570                        575                  580 | 5624 |
| gtt cct cac act gaa tgc agg aag caa aat gat ctc tca atg cga cat<br>Val Pro His Thr Glu Cys Arg Lys Gln Asn Asp Leu Ser Met Arg His<br>            585                      590                      595 | 5672 |
| gaa gct gtt gca att gag gcg gaa tct gct gtg tgt tta cat tat gag<br>Glu Ala Val Ala Ile Glu Ala Glu Ser Ala Val Cys Leu His Tyr Glu<br>600                        605                  610 | 5720 |
| gat aat atg aat aac aac agt agg gag atc aat cag gta ctt cag ttt<br>Asp Asn Met Asn Asn Asn Ser Arg Glu Ile Asn Gln Val Leu Gln Phe<br>615                        620                  625                  630 | 5768 |
| ttg act gtg act ttc tgg ctt atc aag tct gag ggt aac ttg atg gat<br>Leu Thr Val Thr Phe Trp Leu Ile Lys Ser Glu Gly Asn Leu Met Asp<br>                  635                      640                  645 | 5816 |
| cta ctg aag cac aaa tcc act ttg gga aat caa gtt cta gat ctg att<br>Leu Leu Lys His Lys Ser Thr Leu Gly Asn Gln Val Leu Asp Leu Ile<br>            650                      655                      660 | 5864 |
| gag agt gct cat gaa gag ctt att ctc ctt aga tct att ctc atg gat<br>Glu Ser Ala His Glu Glu Leu Ile Leu Leu Arg Ser Ile Leu Met Asp<br>665                        670                  675 | 5912 |
| ctt ctt agg aaa aag ctt tac aga ttg gat gat ctc tta atg cat gct<br>Leu Leu Arg Lys Lys Leu Tyr Arg Leu Asp Asp Leu Leu Met His Ala<br>680                        685                  690 | 5960 |
| gag gtg act gca aaa agg tta gca ata ttc agt ggt tct tgt tat gaa<br>Glu Val Thr Ala Lys Arg Leu Ala Ile Phe Ser Gly Ser Cys Tyr Glu<br>695                        700                  705                  710 | 6008 |
| tat ttc atg aac gga agc agc act gag aaa atg agg ccc ttg tta tct<br>Tyr Phe Met Asn Gly Ser Ser Thr Glu Lys Met Arg Pro Leu Leu Ser<br>                  715                      720                  725 | 6056 |

```
gat ttt ctg caa gag att gag tct gtc aag gta gag ttc aga aat gtt      6104
Asp Phe Leu Gln Glu Ile Glu Ser Val Lys Val Glu Phe Arg Asn Val
            730                 735                 740 tgc ttg caa gtt ctg gat ata tca cct ttt tcc ctg aca gat gga gaa      6152
Cys Leu Gln Val Leu Asp Ile Ser Pro Phe Ser Leu Thr Asp Gly Glu
        745                 750                 755 ggc ctt gtt aat ttc tta tta aaa aac cag gcc aag gtg ccg aat gat      6200
Gly Leu Val Asn Phe Leu Leu Lys Asn Gln Ala Lys Val Pro Asn Asp
    760                 765                 770 gat gct gtt tct tct gat gga agt tta gag gat gca agc agc act gag      6248
Asp Ala Val Ser Ser Asp Gly Ser Leu Glu Asp Ala Ser Ser Thr Glu
775                 780                 785                 790 aaa atg gga ctt cca tct gat ttt ctc cga gag att gag tct gtt gag      6296
Lys Met Gly Leu Pro Ser Asp Phe Leu Arg Glu Ile Glu Ser Val Glu
            795                 800                 805 ata aag gag gcc aga aaa tta tat gat caa gtt ttg gat gca aca cat      6344
Ile Lys Glu Ala Arg Lys Leu Tyr Asp Gln Val Leu Asp Ala Thr His
        810                 815                 820 tgt gag acg agt aag aca gat gga aaa agc ttt atc aac att atg tta      6392
Cys Glu Thr Ser Lys Thr Asp Gly Lys Ser Phe Ile Asn Ile Met Leu
    825                 830                 835 acc caa cag gac aag ttg ccg gac tat gat gct ggt tca gtc tct tat      6440
Thr Gln Gln Asp Lys Leu Pro Asp Tyr Asp Ala Gly Ser Val Ser Tyr
840                 845                 850 ctt ctt aac caa ata tca gta gtt aaa gac aaa cta ttg cac att ggc      6488
Leu Leu Asn Gln Ile Ser Val Val Lys Asp Lys Leu Leu His Ile Gly
855                 860                 865                 870 tct tta ctt gta gat att gta cag tac cgg aat atg cat ata gaa ctt      6536
Ser Leu Leu Val Asp Ile Val Gln Tyr Arg Asn Met His Ile Glu Leu
            875                 880                 885 aca gat ctc gct gaa cgt gtt caa gat aaa aac tac att tgt ttc ttc      6584
Thr Asp Leu Ala Glu Arg Val Gln Asp Lys Asn Tyr Ile Cys Phe Phe
        890                 895                 900 tct gtc aag ggt tat att cct gct tgg tat tac aca cta tat ctc tct      6632
Ser Val Lys Gly Tyr Ile Pro Ala Trp Tyr Tyr Thr Leu Tyr Leu Ser
    905                 910                 915 gat gtc aag caa ttg ctt aag ttt gtt gag gca gag gta aag att att      6680
Asp Val Lys Gln Leu Leu Lys Phe Val Glu Ala Glu Val Lys Ile Ile
920                 925                 930 tgt ctg aaa gta cca gat tct tca agt tat agc ttc cct aag aca aat      6728
Cys Leu Lys Val Pro Asp Ser Ser Ser Tyr Ser Phe Pro Lys Thr Asn
935                 940                 945                 950 gga tta gga tat ctc aat tgc ttt tta ggc aaa ttg gag gag ctt tta      6776
Gly Leu Gly Tyr Leu Asn Cys Phe Leu Gly Lys Leu Glu Glu Leu Leu
            955                 960                 965 cgt tct aag ctc gat ttg ata atc gac tta aaa cat cag att gaa tca      6824
Arg Ser Lys Leu Asp Leu Ile Ile Asp Leu Lys His Gln Ile Glu Ser
        970                 975                 980 gtc aag gag ggc tta ttg tgc cta aga tca ttc att gat cat ttt tca      6872
Val Lys Glu Gly Leu Leu Cys Leu Arg Ser Phe Ile Asp His Phe Ser
    985                 990                 995 gaa agc tat gat gag cat gat gaa gct tgt ggt ctt ata gca aga gtt      6920
Glu Ser Tyr Asp Glu His Asp Glu Ala Cys Gly Leu Ile Ala Arg Val
1000                1005                1010 tct gta atg gca tac aag gct gag tat gtc att gac tca tgc ttg gcc      6968
Ser Val Met Ala Tyr Lys Ala Glu Tyr Val Ile Asp Ser Cys Leu Ala
1015                1020                1025                1030 tat tct cat cca ctc tgg tac aaa gtt ctt tgg att tct gaa gtt ctt      7016
Tyr Ser His Pro Leu Trp Tyr Lys Val Leu Trp Ile Ser Glu Val Leu
```

```
                    1035              1040              1045
gag aat att aag ctt gta aat aaa gtt gtt ggt gag aca tgt gaa aga    7064
Glu Asn Ile Lys Leu Val Asn Lys Val Val Gly Glu Thr Cys Glu Arg
            1050              1055              1060 agg aac att gaa gtt act gtg cat gaa gtt gca aag act acc act tat    7112
Arg Asn Ile Glu Val Thr Val His Glu Val Ala Lys Thr Thr Thr Tyr
            1065              1070              1075 gta gca cca tct ttt tca gct tat act caa aga gca aac gaa gaa atg    7160
Val Ala Pro Ser Phe Ser Ala Tyr Thr Gln Arg Ala Asn Glu Glu Met
        1080              1085              1090 gag ggt ttt cag gat aca ata gat gaa tta aag gat aaa cta ctt gga    7208
Glu Gly Phe Gln Asp Thr Ile Asp Glu Leu Lys Asp Lys Leu Leu Gly
1095              1100              1105              1110 gga tca cct gag ctt gat gtc atc tca atc gtt ggc atg cca gga ttg    7256
Gly Ser Pro Glu Leu Asp Val Ile Ser Ile Val Gly Met Pro Gly Leu
            1115              1120              1125 ggc aag act aca cta gca aag aag att tac aat gat cca gaa gtc acc    7304
Gly Lys Thr Thr Leu Ala Lys Lys Ile Tyr Asn Asp Pro Glu Val Thr
            1130              1135              1140 tct cgc ttc gat gtc cat gct caa tgt gtt gtg act caa tta tat tca    7352
Ser Arg Phe Asp Val His Ala Gln Cys Val Val Thr Gln Leu Tyr Ser
        1145              1150              1155 tgg aga gag ttg ctc acc att ttg aat gat gtc ctt gag cct tct        7400
Trp Arg Glu Leu Leu Thr Ile Leu Asn Asp Val Leu Glu Pro Ser
        1160              1165              1170 gat cgc aat gaa aaa gaa gat ggt gaa ata gct gat gag tta cgc cga    7448
Asp Arg Asn Glu Lys Glu Asp Gly Glu Ile Ala Asp Glu Leu Arg Arg
1175              1180              1185              1190 ttt ttg ttg acc aag aga ttc ttg att ctc att gat gat gtg tgg gac    7496
Phe Leu Leu Thr Lys Arg Phe Leu Ile Leu Ile Asp Asp Val Trp Asp
            1195              1200              1205 tat aaa gtg tgg gac aat cta tgt atg tgc ttc agt gat gtt tca aat    7544
Tyr Lys Val Trp Asp Asn Leu Cys Met Cys Phe Ser Asp Val Ser Asn
        1210              1215              1220 agg agt aga att atc cta aca acc cgc ttg aat gat gtc gcc gaa tat    7592
Arg Ser Arg Ile Ile Leu Thr Thr Arg Leu Asn Asp Val Ala Glu Tyr
        1225              1230              1235 gtc aaa tgt gaa agt gat ccc cat cat ctt cgt tta ttc aga gat gac    7640
Val Lys Cys Glu Ser Asp Pro His His Leu Arg Leu Phe Arg Asp Asp
        1240              1245              1250 gag agt tgg aca tta tta cag aaa gaa gtc ttt caa gga gag agc tgt    7688
Glu Ser Trp Thr Leu Leu Gln Lys Glu Val Phe Gln Gly Glu Ser Cys
1255              1260              1265              1270 cca cct gaa ctt gaa gat gtg gga ttt gaa ata tca aaa agt tgt aga    7736
Pro Pro Glu Leu Glu Asp Val Gly Phe Glu Ile Ser Lys Ser Cys Arg
            1275              1280              1285 ggg ttg cct ctc tca gtt gtg tta gta gct ggt gtt ctg aaa cag aaa    7784
Gly Leu Pro Leu Ser Val Val Leu Val Ala Gly Val Leu Lys Gln Lys
            1290              1295              1300 aag aag aca cta gat tca tgg aaa gta gta gaa caa agt cta agt tcc    7832
Lys Lys Thr Leu Asp Ser Trp Lys Val Val Glu Gln Ser Leu Ser Ser
        1305              1310              1315 cag agg att ggc agc ttg gaa gag agc ata tct ata att gga ttc agt    7880
Gln Arg Ile Gly Ser Leu Glu Glu Ser Ile Ser Ile Ile Gly Phe Ser
        1320              1325              1330 tac aag aat tta cca cac tat ctt aag cct tgt ttt ctc tat ttt gga    7928
Tyr Lys Asn Leu Pro His Tyr Leu Lys Pro Cys Phe Leu Tyr Phe Gly
1335              1340              1345              1350 gga ttt ttg cag gga aag gat att cat gtc tca aaa atg acc aag ttg    7976
```

```
                                        -continued

Gly Phe Leu Gln Gly Lys Asp Ile His Val Ser Lys Met Thr Lys Leu
            1355                1360                1365 tgg gta gct gaa ggg ttt gta caa gca aac aac gaa aaa gga caa gaa    8024
Trp Val Ala Glu Gly Phe Val Gln Ala Asn Asn Glu Lys Gly Gln Glu
        1370                1375                1380 gat acc gca caa ggt ttc ttg gac gat ctt att ggt agg aat gta gtg    8072
Asp Thr Ala Gln Gly Phe Leu Asp Asp Leu Ile Gly Arg Asn Val Val
        1385                1390                1395 atg gcc atg gag aag aga cct aat acc aag gtg aaa acg tgc cgc att    8120
Met Ala Met Glu Lys Arg Pro Asn Thr Lys Val Lys Thr Cys Arg Ile
    1400                1405                1410 cat gat ttg ttg cat aaa ttc tgc atg gaa aag gcc aaa caa gag gat    8168
His Asp Leu Leu His Lys Phe Cys Met Glu Lys Ala Lys Gln Glu Asp
1415                1420                1425                1430 ttt ctt ctc caa atc aat aggtaaaaaa aactgtatta attttacatt           8216
Phe Leu Leu Gln Ile Asn
                1435 accaaaaaaa aagaactgta ttaattttac tgtattatgt ttatgccaac tctcatttcc   8276 atgtgttctc ttttatccaa ttc agt gga gaa ggt gta ttt cct gaa cga ttg  8329
                          Ser Gly Glu Gly Val Phe Pro Glu Arg Leu
                                        1440                1445 gag gaa tac cga ttg ttc gtt cat tct tac caa gat gaa att gat ctg    8377
Glu Glu Tyr Arg Leu Phe Val His Ser Tyr Gln Asp Glu Ile Asp Leu
        1450                1455                1460 tgg cgc cca tct cgc tct aat gtc cga tct tta cta ttc aat gca att    8425
Trp Arg Pro Ser Arg Ser Asn Val Arg Ser Leu Leu Phe Asn Ala Ile
        1465                1470                1475 gat cca gat aac ttg tta tgg ccg cgt gat atc tcc ttc att ttt gag    8473
Asp Pro Asp Asn Leu Leu Trp Pro Arg Asp Ile Ser Phe Ile Phe Glu
        1480                1485                1490 agc ttc aag ctt gtt aaa gtg ttg gat ttg gaa tca ttc aac att ggt    8521
Ser Phe Lys Leu Val Lys Val Leu Asp Leu Glu Ser Phe Asn Ile Gly
1495                1500                1505                1510 ggt act ttt ccc act gaa ata caa tat cta att cag atg aag tac ttt    8569
Gly Thr Phe Pro Thr Glu Ile Gln Tyr Leu Ile Gln Met Lys Tyr Phe
        1515                1520                1525 gcg gcc caa act gat gca aat tca att cct tca tct ata gct aag ctt    8617
Ala Ala Gln Thr Asp Ala Asn Ser Ile Pro Ser Ser Ile Ala Lys Leu
        1530                1535                1540 gaa aat ctt gag act ttt gtc gta aga gga ttg gga gga gag atg ata    8665
Glu Asn Leu Glu Thr Phe Val Val Arg Gly Leu Gly Gly Glu Met Ile
        1545                1550                1555 tta cct tgt tca ctt ctg aag atg gtg aaa ttg agg cat ata cat gta    8713
Leu Pro Cys Ser Leu Leu Lys Met Val Lys Leu Arg His Ile His Val
        1560                1565                1570 aat gat cgg gtt tct ttt ggt ttg cat gag aac atg gat gtt tta act    8761
Asn Asp Arg Val Ser Phe Gly Leu His Glu Asn Met Asp Val Leu Thr
1575                1580                1585                1590 ggt aac tca caa tta cct aat ttg gaa acc ttt tct act cca cgt ctc    8809
Gly Asn Ser Gln Leu Pro Asn Leu Glu Thr Phe Ser Thr Pro Arg Leu
                1595                1600                1605 ttt tat ggt aaa gac gca gag aag gtt ttg agg aag atg cca aaa ttg    8857
Phe Tyr Gly Lys Asp Ala Glu Lys Val Leu Arg Lys Met Pro Lys Leu
        1610                1615                1620 aga aaa ttg agt tgc ata ttt tca ggg aca ttt ggt tat tca agg aaa    8905
Arg Lys Leu Ser Cys Ile Phe Ser Gly Thr Phe Gly Tyr Ser Arg Lys
        1625                1630                1635 ttg aag ggt agg tgt gtt cgt ttt ccc aga tta gat ttt cta agt cac    8953
Leu Lys Gly Arg Cys Val Arg Phe Pro Arg Leu Asp Phe Leu Ser His
```

```
                1640          1645          1650
ctt gag tcc ctc aag ctg gtt tcg aac agc tat cca gcc aaa ctt cct   9001
Leu Glu Ser Leu Lys Leu Val Ser Asn Ser Tyr Pro Ala Lys Leu Pro
1655              1660              1665              1670 cac aag ttc aat ttc ccc tcg caa cta agg gaa ctg act tta tca aag   9049
His Lys Phe Asn Phe Pro Ser Gln Leu Arg Glu Leu Thr Leu Ser Lys
            1675              1680              1685 ttc cgt cta cct tgg acc caa att tcg atc att gca gaa ctg ccc aac   9097
Phe Arg Leu Pro Trp Thr Gln Ile Ser Ile Ile Ala Glu Leu Pro Asn
      1690              1695              1700 ttg gta att ctt aag tta ttg ctc aga gcc ttt gaa ggg gat cac tgg   9145
Leu Val Ile Leu Lys Leu Leu Leu Arg Ala Phe Glu Gly Asp His Trp
1705              1710              1715 gaa gtg aaa gat tca gag ttc cta gaa ctc aaa tac tta aaa ctg gac   9193
Glu Val Lys Asp Ser Glu Phe Leu Glu Leu Lys Tyr Leu Lys Leu Asp
      1720              1725              1730 aac ctc aaa gtt gta caa tgg tcc atc tct gat gat gct ttt cct aag   9241
Asn Leu Lys Val Val Gln Trp Ser Ile Ser Asp Asp Ala Phe Pro Lys
1735              1740              1745              1750 ctt gaa cat ttg gtt tta acg aaa tgt aag cat ctt gag aaa atc cct   9289
Leu Glu His Leu Val Leu Thr Lys Cys Lys His Leu Glu Lys Ile Pro
            1755              1760              1765 tct cgt ttt gaa gat gct gtt tgc cta aat aga gtt gag gtg aac tgg   9337
Ser Arg Phe Glu Asp Ala Val Cys Leu Asn Arg Val Glu Val Asn Trp
      1770              1775              1780 tgc aac tgg aat gtt gcc aat tca gcc caa gat att caa act atg caa   9385
Cys Asn Trp Asn Val Ala Asn Ser Ala Gln Asp Ile Gln Thr Met Gln
1785              1790              1795 cat gaa gtt ata gca aat gat tca ttc aca gtt act ata cag cct cca   9433
His Glu Val Ile Ala Asn Asp Ser Phe Thr Val Thr Ile Gln Pro Pro
      1800              1805              1810 gat tgg tct aaa gaa cag ccc ctt gac tct tag caaaggtttg ttcttgctgt   9486
Asp Trp Ser Lys Glu Gln Pro Leu Asp Ser
1815              1820              1825 gttcatccaa gtacatttaa catttattca ttttgttttg caccagaaca tgtttgtttt   9546
gctagtatta cttgatacat taaaagaaat cgaactcata tttctgctac agtcttaact   9606
tttcttgggc ttactcgagg tctagattag atcaatggtt catgtaattc ttaattcact   9666
gtttcattca actgtcttat catagttgtg aaatgacaat attgttatcc ctagccaaat   9726
ttattatgtt caaatgaaaa ctgatgtcac aactactttt ttgtgaaatg tttttgaatt   9786
ttttgctata aaattgacga attgacaggc ttctattttt gtcagctaaa ctctttgtca   9846
ccagaggtgt atttagaatt actgtggttt tatgaaagat ttttatagaa ttttatgctt   9906
ttgcagaatc ttaagtttct agtttaaaac aacagcactt ttctgtttca gaggtagcag   9966
cagctaaagt tcaaggcatt ttgtttattt ctagaacaag gggagttctt acgttgaatt   10026
cttgaaaaga agaagaatca ggagcaggta agattatct cttttctgt ttttcttctt   10086 ttagatgtta tttcttcatc ttgaacgtga acaccgctga aagcatttta ataaaaccgg   10146
agaaataaat aagatctttt tatataaagc attatcatgt aaatatgcct aaatccatat   10206
ggtacaactg tttgacaaat gatagagagg ggagactgat gcaagtttta tagtataagt   10266
aaaacaggat tgagaaaaaa atccttgcac gattttcaat ttctggccac atcacaatgt   10326
gtgtcaaagt tcccctcttt aagtggaaca agcaatcaga aaagcacatt cttatcggtg   10386
acttaccaat accagctgac tgtctcatct tggttaactt agccttgctt acttagacta   10446
ttagattagt tactaatgag ctggtaaatt ggaaccaaat gtagttagct tgatgagctg   10506
```

-continued

```
gtagatatgt atgtatgaag atacacgcgt aactttagtc aatggttaat ttttcatttt   10566
gtattttttt cttcacagag tatatatgac gcgagaatac ttggcctaaa agtttttgct   10626
tcactaattt aactattgcc gtggatgaaa caagcatggc aacattttca acaactatca   10686
ctcaagcaat gtaaaaaaag gaggttctac gagtggtaca tgtaagagtt ttgtgcacac   10746
aagaggttct gagacttgaa ccatccatgt ccaaggcagt tcagatgcta gtaaagaaag   10806
aagaagatga acctgcacta attaatcctc cctttatgaa taagagaatg agaaaaagat   10866
ggagcttcat gaaccaaaag ttaccttttt ttttttttaat ggcattactt tgaagcacat   10926
gtttgttagt tgtaaattgt aatggtgaag tgtttgtaaa ta                      10968
```

<210> SEQ ID NO 2
<211> LENGTH: 1824
<212> TYPE: PRT
<213> ORGANISM: Lycopersicon esculentum

<400> SEQUENCE: 2

```
Met Ala Lys Glu Cys Arg Asp Ala Ile Gly Thr Ile Asn Leu Val Lys
  1               5                  10                  15

Gly Gln His Leu Asp Arg Arg Thr Thr Asn Gln Leu Glu Asp Ala Ile
             20                  25                  30

Lys His Leu Thr His Val Ala Val Phe Leu Thr Asn Leu Glu Lys Arg
         35                  40                  45

His Pro Ala Asn Gly Ile Ser Ile His Leu Arg Pro Leu Phe Leu Glu
     50                  55                  60

Ala His Asp Gly Phe Ser Leu Met Cys Ser His Pro Pro Arg Ser Gln
 65                  70                  75                  80

Phe Thr Val Lys Leu Asp Asn Ile Ala Glu Lys Phe Lys Ser Ser Lys
                 85                  90                  95

Ala Ser Arg Ser Thr Arg Gln Val Ile Pro Glu Leu Leu Gln Ile Ile
            100                 105                 110

Glu Pro Glu Asn Ile Ala Lys Arg Ile Lys Ala Ser Lys Pro Ser Arg
        115                 120                 125

Ser Ser Ser Pro Ile Thr Val Asp Met Val Gly Phe Ile Glu Ser Leu
    130                 135                 140

Leu Gly Ser Val His Arg Ala Leu Phe Phe Ile Ser Ala Gly Pro Pro
145                 150                 155                 160

Val Ser Met Leu Asp Lys Lys Leu Arg His Leu Gln Val Phe Phe Arg
                165                 170                 175

Leu Ile Ser Lys Arg Gly Ile Glu His Glu Ser Met Lys Asp Leu Phe
            180                 185                 190

Tyr His Val Glu Asp Val Ala Tyr Thr Ala Ala Gln Leu Cys Val Leu
        195                 200                 205

Gly Ser Ser Cys His Met Asp Asp Glu Phe Ser Lys Phe Leu Glu Arg
    210                 215                 220

Ile Ser Arg Pro Phe Ser Pro Gly Leu Arg Gln Val Tyr Leu Asn Ala
225                 230                 235                 240

Leu Ile Gly Leu Asn Ser Ser Arg Ser Lys Thr Thr Met Asn Ala Lys
                245                 250                 255

Tyr Met Leu Asp Phe Val Ser Ala Leu Gln Asp Asp Leu Arg Leu Arg
            260                 265                 270

Cys Asp Asn Arg Ile Arg Trp Leu Gln Arg Gly Leu Ser Tyr Leu Cys
        275                 280                 285
```

```
Arg Phe Leu Arg Asp Ile Glu Ser Tyr Pro Val Ser His Arg Gln Leu
290                 295                 300
Ile Ser Leu Gln Leu Asn Met Glu Asp Leu Ala Ile Gly Ser Ala Asn
305                 310                 315                 320
Ala Ile Tyr Ser Tyr Asp Glu Asp Met Asp Lys Thr Ser Glu Ile Asp
                325                 330                 335
His Glu Leu Phe His Leu Gln Met Lys Phe Asn Tyr Val Lys Val Glu
            340                 345                 350
Val Asp Leu Ile Arg Leu Gln Asn Ile Gln Gly Thr Ile Ile Val Pro
            355                 360                 365
Met Lys Asp Leu Ile Asp Tyr Val Trp Glu Glu Leu Met Phe Phe Arg
370                 375                 380
Ser Tyr Phe Met Asp Ala Phe Asp Gln Phe Lys Glu Gln Thr Arg Ile
385                 390                 395                 400
Thr Val Ile Leu Asn Tyr Ile Gln Ser Ala Val Ser Gln Ala Trp Ser
                405                 410                 415
Val Cys Asp Ser Leu Cys His Asp Leu Asn Gln Asn Asp Leu Ala Arg
            420                 425                 430
Glu Ile Asn Cys Leu His Phe Gln Leu Leu Leu Lys Phe Lys Phe Ile
            435                 440                 445
Lys Val Ala Ile Arg Gln Met Cys Pro Ser Ile Ser Ala Ser Ser Thr
450                 455                 460
Pro Asp His Pro Met Ile Asp Leu Leu Asn Phe Leu Pro Met Asn Phe
465                 470                 475                 480
Glu Ala Ile Asp Ser Tyr Ser Ser Met Leu Lys Ala Ser Cys Pro Ser
                485                 490                 495
Ser Ser His Arg Pro Asn Arg Asp Ala Glu Ser Pro Asn Thr Ser Phe
            500                 505                 510
Leu Cys Gly Pro Asn Thr Asp Val Tyr Ser Phe Tyr Ser Ser Ser Ser
            515                 520                 525
Arg Ile Pro Lys Met Asp Glu Ile Leu Lys Arg Phe His Glu Tyr Ile
530                 535                 540
Leu Val Asn Leu Leu Arg Lys Asp Glu Thr Asn Leu Thr Phe Thr Ile
545                 550                 555                 560
Ala Asp Glu Val Lys Lys Phe Tyr Asp Gly Leu Leu Leu Met Val Thr
                565                 570                 575
Tyr Leu Ile Glu Pro Pro Val Pro His Thr Glu Cys Arg Lys Gln Asn
            580                 585                 590
Asp Leu Ser Met Arg His Glu Ala Val Ala Ile Glu Ala Glu Ser Ala
            595                 600                 605
Val Cys Leu His Tyr Glu Asp Asn Met Asn Asn Asn Ser Arg Glu Ile
610                 615                 620
Asn Gln Val Leu Gln Phe Leu Thr Val Thr Phe Trp Leu Ile Lys Ser
625                 630                 635                 640
Glu Gly Asn Leu Met Asp Leu Leu Lys His Lys Ser Thr Leu Gly Asn
                645                 650                 655
Gln Val Leu Asp Leu Ile Glu Ser Ala His Glu Glu Leu Ile Leu Leu
            660                 665                 670
Arg Ser Ile Leu Met Asp Leu Leu Arg Lys Lys Leu Tyr Arg Leu Asp
            675                 680                 685
Asp Leu Leu Met His Ala Glu Val Thr Ala Lys Arg Leu Ala Ile Phe
690                 695                 700
Ser Gly Ser Cys Tyr Glu Tyr Phe Met Asn Gly Ser Ser Thr Glu Lys
```

-continued

```
              705                 710                 715                 720
Met Arg Pro Leu Leu Ser Asp Phe Leu Gln Glu Ile Glu Ser Val Lys
                    725                 730                 735

Val Glu Phe Arg Asn Val Cys Leu Gln Val Leu Asp Ile Ser Pro Phe
                    740                 745                 750

Ser Leu Thr Asp Gly Glu Gly Leu Val Asn Phe Leu Leu Lys Asn Gln
                    755                 760                 765

Ala Lys Val Pro Asn Asp Asp Ala Val Ser Ser Asp Gly Ser Leu Glu
                    770                 775                 780

Asp Ala Ser Ser Thr Glu Lys Met Gly Leu Pro Ser Asp Phe Leu Arg
785                 790                 795                 800

Glu Ile Glu Ser Val Glu Ile Lys Glu Ala Arg Lys Leu Tyr Asp Gln
                    805                 810                 815

Val Leu Asp Ala Thr His Cys Glu Thr Ser Lys Thr Asp Gly Lys Ser
                    820                 825                 830

Phe Ile Asn Ile Met Leu Thr Gln Gln Asp Lys Leu Pro Asp Tyr Asp
                    835                 840                 845

Ala Gly Ser Val Ser Tyr Leu Leu Asn Gln Ile Ser Val Val Lys Asp
                    850                 855                 860

Lys Leu Leu His Ile Gly Ser Leu Leu Val Asp Ile Val Gln Tyr Arg
865                 870                 875                 880

Asn Met His Ile Glu Leu Thr Asp Leu Ala Glu Arg Val Gln Asp Lys
                    885                 890                 895

Asn Tyr Ile Cys Phe Phe Ser Val Lys Gly Tyr Ile Pro Ala Trp Tyr
                    900                 905                 910

Tyr Thr Leu Tyr Leu Ser Asp Val Lys Gln Leu Leu Lys Phe Val Glu
                    915                 920                 925

Ala Glu Val Lys Ile Ile Cys Leu Lys Val Pro Asp Ser Ser Ser Tyr
                    930                 935                 940

Ser Phe Pro Lys Thr Asn Gly Leu Gly Tyr Leu Asn Cys Phe Leu Gly
945                 950                 955                 960

Lys Leu Glu Glu Leu Leu Arg Ser Lys Leu Asp Leu Ile Ile Asp Leu
                    965                 970                 975

Lys His Gln Ile Glu Ser Val Lys Glu Gly Leu Leu Cys Leu Arg Ser
                    980                 985                 990

Phe Ile Asp His Phe Ser Glu Ser Tyr Asp Glu His Asp Glu Ala Cys
                    995                 1000                1005

Gly Leu Ile Ala Arg Val Ser Val Met Ala Tyr Lys Ala Glu Tyr Val
                    1010                1015                1020

Ile Asp Ser Cys Leu Ala Tyr Ser His Pro Leu Trp Tyr Lys Val Leu
1025                1030                1035                1040

Trp Ile Ser Glu Val Leu Glu Asn Ile Lys Leu Val Asn Lys Val Val
                    1045                1050                1055

Gly Glu Thr Cys Glu Arg Arg Asn Ile Glu Val Thr Val His Glu Val
                    1060                1065                1070

Ala Lys Thr Thr Thr Tyr Val Ala Pro Ser Phe Ser Ala Tyr Thr Gln
                    1075                1080                1085

Arg Ala Asn Glu Glu Met Glu Gly Phe Gln Asp Thr Ile Asp Glu Leu
                    1090                1095                1100

Lys Asp Lys Leu Leu Gly Gly Ser Pro Glu Leu Asp Val Ile Ser Ile
1105                1110                1115                1120

Val Gly Met Pro Gly Leu Gly Lys Thr Thr Leu Ala Lys Lys Ile Tyr
                    1125                1130                1135
```

-continued

```
Asn Asp Pro Glu Val Thr Ser Arg Phe Asp Val His Ala Gln Cys Val
            1140                1145                1150

Val Thr Gln Leu Tyr Ser Trp Arg Glu Leu Leu Thr Ile Leu Asn
        1155                1160                1165

Asp Val Leu Glu Pro Ser Asp Arg Asn Glu Lys Glu Asp Gly Glu Ile
    1170                1175                1180

Ala Asp Glu Leu Arg Arg Phe Leu Leu Thr Lys Arg Phe Leu Ile Leu
1185                1190                1195                1200

Ile Asp Asp Val Trp Asp Tyr Lys Val Trp Asp Asn Leu Cys Met Cys
            1205                1210                1215

Phe Ser Asp Val Ser Asn Arg Ser Arg Ile Ile Leu Thr Thr Arg Leu
            1220                1225                1230

Asn Asp Val Ala Glu Tyr Val Lys Cys Glu Ser Asp Pro His His Leu
            1235                1240                1245

Arg Leu Phe Arg Asp Asp Glu Ser Trp Thr Leu Leu Gln Lys Glu Val
            1250                1255                1260

Phe Gln Gly Glu Ser Cys Pro Pro Glu Leu Glu Asp Val Gly Phe Glu
1265                1270                1275                1280

Ile Ser Lys Ser Cys Arg Gly Leu Pro Leu Ser Val Val Leu Val Ala
            1285                1290                1295

Gly Val Leu Lys Gln Lys Lys Lys Thr Leu Asp Ser Trp Lys Val Val
            1300                1305                1310

Glu Gln Ser Leu Ser Ser Gln Arg Ile Gly Ser Leu Glu Glu Ser Ile
            1315                1320                1325

Ser Ile Ile Gly Phe Ser Tyr Lys Asn Leu Pro His Tyr Leu Lys Pro
            1330                1335                1340

Cys Phe Leu Tyr Phe Gly Gly Phe Leu Gln Gly Lys Asp Ile His Val
1345                1350                1355                1360

Ser Lys Met Thr Lys Leu Trp Val Ala Glu Gly Phe Val Gln Ala Asn
            1365                1370                1375

Asn Glu Lys Gly Gln Glu Asp Thr Ala Gln Gly Phe Leu Asp Asp Leu
            1380                1385                1390

Ile Gly Arg Asn Val Val Met Ala Met Glu Lys Arg Pro Asn Thr Lys
            1395                1400                1405

Val Lys Thr Cys Arg Ile His Asp Leu Leu His Lys Phe Cys Met Glu
            1410                1415                1420

Lys Ala Lys Gln Glu Asp Phe Leu Leu Gln Ile Asn Ser Gly Glu Gly
1425                1430                1435                1440

Val Phe Pro Glu Arg Leu Glu Glu Tyr Arg Leu Phe Val His Ser Tyr
            1445                1450                1455

Gln Asp Glu Ile Asp Leu Trp Arg Pro Ser Arg Ser Asn Val Arg Ser
            1460                1465                1470

Leu Leu Phe Asn Ala Ile Asp Pro Asp Asn Leu Leu Trp Pro Arg Asp
            1475                1480                1485

Ile Ser Phe Ile Phe Glu Ser Phe Lys Leu Val Lys Val Leu Asp Leu
            1490                1495                1500

Glu Ser Phe Asn Ile Gly Gly Thr Phe Pro Thr Glu Ile Gln Tyr Leu
1505                1510                1515                1520

Ile Gln Met Lys Tyr Phe Ala Ala Gln Thr Asp Ala Asn Ser Ile Pro
            1525                1530                1535

Ser Ser Ile Ala Lys Leu Glu Asn Leu Glu Thr Phe Val Arg Gly
            1540                1545                1550
```

-continued

```
Leu Gly Gly Glu Met Ile Leu Pro Cys Ser Leu Leu Lys Met Val Lys
        1555                1560                1565

Leu Arg His Ile His Val Asn Asp Arg Val Ser Phe Gly Leu His Glu
        1570                1575                1580

Asn Met Asp Val Leu Thr Gly Asn Ser Gln Leu Pro Asn Leu Glu Thr
1585                1590                1595                1600

Phe Ser Thr Pro Arg Leu Phe Tyr Gly Lys Asp Ala Glu Lys Val Leu
            1605                1610                1615

Arg Lys Met Pro Lys Leu Arg Lys Leu Ser Cys Ile Phe Ser Gly Thr
                1620                1625                1630

Phe Gly Tyr Ser Arg Lys Leu Lys Gly Arg Cys Val Arg Phe Pro Arg
        1635                1640                1645

Leu Asp Phe Leu Ser His Leu Glu Ser Leu Lys Leu Val Ser Asn Ser
        1650                1655                1660

Tyr Pro Ala Lys Leu Pro His Lys Phe Asn Phe Pro Ser Gln Leu Arg
1665                1670                1675                1680

Glu Leu Thr Leu Ser Lys Phe Arg Leu Pro Trp Thr Gln Ile Ser Ile
            1685                1690                1695

Ile Ala Glu Leu Pro Asn Leu Val Ile Leu Lys Leu Leu Arg Ala
                1700                1705                1710

Phe Glu Gly Asp His Trp Glu Val Lys Asp Ser Glu Phe Leu Glu Leu
        1715                1720                1725

Lys Tyr Leu Lys Leu Asp Asn Leu Lys Val Val Gln Trp Ser Ile Ser
        1730                1735                1740

Asp Asp Ala Phe Pro Lys Leu Glu His Leu Val Leu Thr Lys Cys Lys
1745                1750                1755                1760

His Leu Glu Lys Ile Pro Ser Arg Phe Glu Asp Ala Val Cys Leu Asn
            1765                1770                1775

Arg Val Glu Val Asn Trp Cys Asn Trp Asn Val Ala Asn Ser Ala Gln
                1780                1785                1790

Asp Ile Gln Thr Met Gln His Glu Val Ile Ala Asn Asp Ser Phe Thr
        1795                1800                1805

Val Thr Ile Gln Pro Pro Asp Trp Ser Lys Glu Gln Pro Leu Asp Ser
        1810                1815                1820

<210> SEQ ID NO 3
<211> LENGTH: 5475
<212> TYPE: DNA
<213> ORGANISM: Lycopersicon esculentum
<220> FEATURE:
<221> NAME/KEY: CDS
<222> LOCATION: (1)..(5475)

<400> SEQUENCE: 3 atg gcc aag gag tgt cgc gat gca ata ggt act ata aac ctt gtg aag      48
Met Ala Lys Glu Cys Arg Asp Ala Ile Gly Thr Ile Asn Leu Val Lys
  1               5                  10                  15 ggc cag cat tta gac aga agg acc act aat caa ttg gag gat gct ata      96
Gly Gln His Leu Asp Arg Arg Thr Thr Asn Gln Leu Glu Asp Ala Ile
             20                  25                  30 aag cac cta aca cat gtt gct gta ttt ctc aca aat ctg gag aag cgt     144
Lys His Leu Thr His Val Ala Val Phe Leu Thr Asn Leu Glu Lys Arg
         35                  40                  45 cac cct gct aat gga ata tct ata cat ctt agg cct cta ttt tta gaa    192
His Pro Ala Asn Gly Ile Ser Ile His Leu Arg Pro Leu Phe Leu Glu
     50                  55                  60 gct cat gat ggc ttt tct ctg atg tgt tct cat cct cct cgt tct cag    240
```

```
Ala His Asp Gly Phe Ser Leu Met Cys Ser His Pro Arg Ser Gln
 65              70                  75                  80 ttt acc gtt aaa ctg gat aac att gct gag aaa ttc aaa tct tca aag       288
Phe Thr Val Lys Leu Asp Asn Ile Ala Glu Lys Phe Lys Ser Ser Lys
             85                  90                  95 gcg tca aga tca aca agg caa gtg atc cca gag ctg ctg caa ata att       336
Ala Ser Arg Ser Thr Arg Gln Val Ile Pro Glu Leu Leu Gln Ile Ile
            100                 105                 110 gaa ccc gag aat att gct aag cga atc aaa gct tca aag cca tca aga       384
Glu Pro Glu Asn Ile Ala Lys Arg Ile Lys Ala Ser Lys Pro Ser Arg
            115                 120                 125 tca tct agc cca atc act gtg gat atg gtg ggg ttt atc gaa tcc ttg       432
Ser Ser Ser Pro Ile Thr Val Asp Met Val Gly Phe Ile Glu Ser Leu
130                 135                 140 ctt ggt tct gtt cat cgt gca ttg ttc ttt atc agt gca ggg cct cct       480
Leu Gly Ser Val His Arg Ala Leu Phe Phe Ile Ser Ala Gly Pro Pro
145                 150                 155                 160 gtg tct atg ctt gac aag aag ctt cga cat cta caa gtc ttc ttt aga       528
Val Ser Met Leu Asp Lys Lys Leu Arg His Leu Gln Val Phe Phe Arg
                165                 170                 175 cta att tca aag cgg ggc att gag cat gag agt atg aag gat ctc ttc       576
Leu Ile Ser Lys Arg Gly Ile Glu His Glu Ser Met Lys Asp Leu Phe
            180                 185                 190 tac cat gtt gag gat gta gct tac act gca gca caa cta tgt gtc ttg       624
Tyr His Val Glu Asp Val Ala Tyr Thr Ala Ala Gln Leu Cys Val Leu
            195                 200                 205 ggg tcg agc tgc cat atg gat gac gag ttc tct aaa ttt ctg gaa agg       672
Gly Ser Ser Cys His Met Asp Asp Glu Phe Ser Lys Phe Leu Glu Arg
210                 215                 220 ata agt cgt cct ttt agc cca gga ttg agg cag gtt tat ctc aat gcc       720
Ile Ser Arg Pro Phe Ser Pro Gly Leu Arg Gln Val Tyr Leu Asn Ala
225                 230                 235                 240 ttg ata ggg tta aat tca tca aga tca aag act aca atg aat gcc aaa       768
Leu Ile Gly Leu Asn Ser Ser Arg Ser Lys Thr Thr Met Asn Ala Lys
                245                 250                 255 tat atg ctt gat ttt gtt agt gct ctc caa gat gat ctg aga cta aga       816
Tyr Met Leu Asp Phe Val Ser Ala Leu Gln Asp Asp Leu Arg Leu Arg
            260                 265                 270 tgt gat aat cga att cga tgg ctc caa cga gga ctt tct tac ctt tgt       864
Cys Asp Asn Arg Ile Arg Trp Leu Gln Arg Gly Leu Ser Tyr Leu Cys
            275                 280                 285 cga ttc ctc agg gac ata gaa tct tat cct gtt tca cat cga caa ctg       912
Arg Phe Leu Arg Asp Ile Glu Ser Tyr Pro Val Ser His Arg Gln Leu
290                 295                 300 att tct ctt caa ttg aat atg gaa gat ctg gct att ggg tct gca aat       960
Ile Ser Leu Gln Leu Asn Met Glu Asp Leu Ala Ile Gly Ser Ala Asn
305                 310                 315                 320 gcc atc tac tcc tat gat gag gat atg gat aag act agt gaa ata gac      1008
Ala Ile Tyr Ser Tyr Asp Glu Asp Met Asp Lys Thr Ser Glu Ile Asp
                325                 330                 335 cat gag ctt ttt cat ttg caa atg aag ttt aat tat gtt aaa gta gag      1056
His Glu Leu Phe His Leu Gln Met Lys Phe Asn Tyr Val Lys Val Glu
            340                 345                 350 gtt gat ctg att cgt cta caa aac att caa ggc acc ata ata gtt cct      1104
Val Asp Leu Ile Arg Leu Gln Asn Ile Gln Gly Thr Ile Ile Val Pro
            355                 360                 365 atg aaa gat ctg atc gac tat gtt tgg gaa gag ctg atg ttc ttt aga      1152
Met Lys Asp Leu Ile Asp Tyr Val Trp Glu Glu Leu Met Phe Phe Arg
370                 375                 380
```

```
                                                        -continued agt tat ttc atg gat gca ttc gac cag ttt aaa gag cag acc agg ata    1200
Ser Tyr Phe Met Asp Ala Phe Asp Gln Phe Lys Glu Gln Thr Arg Ile
385                 390                 395                 400 act gtt att ttg aac tat att cag tct gca gtt agt caa gca tgg tca    1248
Thr Val Ile Leu Asn Tyr Ile Gln Ser Ala Val Ser Gln Ala Trp Ser
            405                 410                 415 gtc tgt gat tct ctt tgt cat gac ttg aat caa aat gac ttg gcc agg    1296
Val Cys Asp Ser Leu Cys His Asp Leu Asn Gln Asn Asp Leu Ala Arg
        420                 425                 430 gaa att aat tgc ttg cat ttt caa ttg ctt ctt aag ttc aag ttt atc    1344
Glu Ile Asn Cys Leu His Phe Gln Leu Leu Leu Lys Phe Lys Phe Ile
    435                 440                 445 aag gtc gct att aga cag atg tgt ccc agc att tct gca tca tca aca    1392
Lys Val Ala Ile Arg Gln Met Cys Pro Ser Ile Ser Ala Ser Ser Thr
450                 455                 460 cca gac cat cca atg ata gat ctg ctg aac ttt ctt ccc atg aac ttt    1440
Pro Asp His Pro Met Ile Asp Leu Leu Asn Phe Leu Pro Met Asn Phe
465                 470                 475                 480 gag gcc att gat tcc tat tcc agc atg cta aaa gcc tcc tgt cca tct    1488
Glu Ala Ile Asp Ser Tyr Ser Ser Met Leu Lys Ala Ser Cys Pro Ser
            485                 490                 495 tcc tca cat cgt cct aat agg gat gcg gaa tcc ccc aat aca tca ttc    1536
Ser Ser His Arg Pro Asn Arg Asp Ala Glu Ser Pro Asn Thr Ser Phe
        500                 505                 510 tta tgt ggt ccc aat aca gat gtg tac tcc ttc tat tca tca tcc tca    1584
Leu Cys Gly Pro Asn Thr Asp Val Tyr Ser Phe Tyr Ser Ser Ser Ser
    515                 520                 525 cgt att ccc aag atg gat gag ata ttg aag agg ttt cat gaa tat att    1632
Arg Ile Pro Lys Met Asp Glu Ile Leu Lys Arg Phe His Glu Tyr Ile
530                 535                 540 ctt gtc aat ctg cta cgg aag gat gaa acc aat ttg aca ttt act att    1680
Leu Val Asn Leu Leu Arg Lys Asp Glu Thr Asn Leu Thr Phe Thr Ile
545                 550                 555                 560 gca gat gag gtc aaa aag ttt tat gaa ggg ttg ttg ctc atg gtt aca    1728
Ala Asp Glu Val Lys Lys Phe Tyr Glu Gly Leu Leu Leu Met Val Thr
            565                 570                 575 tat ctt att gaa cct cca gtt cct cac act gaa tgc agg aag caa aat    1776
Tyr Leu Ile Glu Pro Pro Val Pro His Thr Glu Cys Arg Lys Gln Asn
        580                 585                 590 gat ctc tca atg cga cat gaa gct gtt gca att gag gcg gaa tct gct    1824
Asp Leu Ser Met Arg His Glu Ala Val Ala Ile Glu Ala Glu Ser Ala
    595                 600                 605 gtg tgt tta cat tat gag gat aat atg aat aac aac agt agg gag atc    1872
Val Cys Leu His Tyr Glu Asp Asn Met Asn Asn Asn Ser Arg Glu Ile
610                 615                 620 aat cag gta ctt cag ttt ttg act gtg act ttc tgg ctt atc aag tct    1920
Asn Gln Val Leu Gln Phe Leu Thr Val Thr Phe Trp Leu Ile Lys Ser
625                 630                 635                 640 gag ggt aac ttg atg gat cta ctg aag cac aaa tcc act ttg gga aat    1968
Glu Gly Asn Leu Met Asp Leu Leu Lys His Lys Ser Thr Leu Gly Asn
            645                 650                 655 caa gtt cta gat ctg att gag agt gct cat gaa gag ctt att ctc ctt    2016
Gln Val Leu Asp Leu Ile Glu Ser Ala His Glu Glu Leu Ile Leu Leu
        660                 665                 670 aga tct att ctc atg gat ctt ctt agg aaa aag ctt tac aga ttg gat    2064
Arg Ser Ile Leu Met Asp Leu Leu Arg Lys Lys Leu Tyr Arg Leu Asp
    675                 680                 685 gat ctc tta atg cat gct gag gtg act gca aaa agg tta gca ata ttc    2112
Asp Leu Leu Met His Ala Glu Val Thr Ala Lys Arg Leu Ala Ile Phe
690                 695                 700
```

-continued

```
agt ggt tct tgt tat gaa tat ttc atg aac gga agc agc act gag aaa    2160
Ser Gly Ser Cys Tyr Glu Tyr Phe Met Asn Gly Ser Ser Thr Glu Lys
705             710                 715                 720 atg agg ccc ttg tta tct gat ttt ctg caa gag att gag tct gtc aag    2208
Met Arg Pro Leu Leu Ser Asp Phe Leu Gln Glu Ile Glu Ser Val Lys
                725                 730                 735 gta gag ttc aga aat gtt tgc ttg caa gtt ctg gat ata tca cct ttt    2256
Val Glu Phe Arg Asn Val Cys Leu Gln Val Leu Asp Ile Ser Pro Phe
            740                 745                 750 tcc ctg aca gat gga gaa ggc ctt gtt aat ttc tta tta aaa aac cag    2304
Ser Leu Thr Asp Gly Glu Gly Leu Val Asn Phe Leu Leu Lys Asn Gln
        755                 760                 765 gcc aag gtg ccg aat gat gat gct gtt tct tct gat gga agt tta gag    2352
Ala Lys Val Pro Asn Asp Asp Ala Val Ser Ser Asp Gly Ser Leu Glu
    770                 775                 780 gat gca agc agc act gag aaa atg gga ctt cca tct gat ttt ctc cga    2400
Asp Ala Ser Ser Thr Glu Lys Met Gly Leu Pro Ser Asp Phe Leu Arg
785                 790                 795                 800 gag att gag tct gtt gag ata aag gag gcc aga aaa tta tat gat caa    2448
Glu Ile Glu Ser Val Glu Ile Lys Glu Ala Arg Lys Leu Tyr Asp Gln
                805                 810                 815 gtt ttg gat gca aca cat tgt gag acg agt aag aca gat gga aaa agc    2496
Val Leu Asp Ala Thr His Cys Glu Thr Ser Lys Thr Asp Gly Lys Ser
            820                 825                 830 ttt atc aac att atg tta acc caa cag gac aag ttg ccg gac tat gat    2544
Phe Ile Asn Ile Met Leu Thr Gln Gln Asp Lys Leu Pro Asp Tyr Asp
        835                 840                 845 gct ggt tca gtc tct tat ctt ctt aac caa ata tca gta gtt aaa gac    2592
Ala Gly Ser Val Ser Tyr Leu Leu Asn Gln Ile Ser Val Val Lys Asp
    850                 855                 860 aaa tta ttg cac att ggc tct tta ctt gta gat att gta cag tac cgg    2640
Lys Leu Leu His Ile Gly Ser Leu Leu Val Asp Ile Val Gln Tyr Arg
865                 870                 875                 880 aat atg cat ata gaa ctt aca gat ctc gct gaa cgt gtt caa gat aaa    2688
Asn Met His Ile Glu Leu Thr Asp Leu Ala Glu Arg Val Gln Asp Lys
                885                 890                 895 aac tac att tgt ttc ttc tct gtc aag ggt tat att cct gct tgg tat    2736
Asn Tyr Ile Cys Phe Phe Ser Val Lys Gly Tyr Ile Pro Ala Trp Tyr
            900                 905                 910 tac aca cta tat ctc tct gat gtc aag caa ttg ctt aag ttt gtt gag    2784
Tyr Thr Leu Tyr Leu Ser Asp Val Lys Gln Leu Leu Lys Phe Val Glu
        915                 920                 925 gca gag gta aag att att tgt ctg aaa gta cca gat tct tca agt tat    2832
Ala Glu Val Lys Ile Ile Cys Leu Lys Val Pro Asp Ser Ser Ser Tyr
    930                 935                 940 agc ttc cct aag aca aat gga tta gga tat ctc aat tgc ttt tta ggc    2880
Ser Phe Pro Lys Thr Asn Gly Leu Gly Tyr Leu Asn Cys Phe Leu Gly
945                 950                 955                 960 aaa ttg gag gag ctt tta cgt tct aag ctc gat ttg ata atc gac tta    2928
Lys Leu Glu Glu Leu Leu Arg Ser Lys Leu Asp Leu Ile Ile Asp Leu
                965                 970                 975 aaa cat cag att gaa tca gtc aag gag ggc tta ttg tgc cta aga tca    2976
Lys His Gln Ile Glu Ser Val Lys Glu Gly Leu Leu Cys Leu Arg Ser
            980                 985                 990 ttc att gat cat ttt tca gaa agc tat gat gag cat gat gaa gct tgt    3024
Phe Ile Asp His Phe Ser Glu Ser Tyr Asp Glu His Asp Glu Ala Cys
        995                 1000                1005 ggt ctt ata gca aga gtt tct gta atg gca tac aag gct gag tat gtc    3072
Gly Leu Ile Ala Arg Val Ser Val Met Ala Tyr Lys Ala Glu Tyr Val
```

|  |  |  |  |  |  |  |  |  |  |  |  |  |  |  |  |  |
|--|--|--|--|--|--|--|--|--|--|--|--|--|--|--|--|--|
| | | 1010 | | | | | 1015 | | | | | 1020 | | | | |
| att | tca | tgc | ttg | gcc | tat | tct | cat | cca | ctc | tgg | tac | aaa | gtt | ctt | | 3120 |
| Ile | Asp | Ser | Cys | Leu | Ala | Tyr | Ser | His | Pro | Leu | Trp | Tyr | Lys | Val | Leu | |
| 1025 | | | | 1030 | | | | | 1035 | | | | | 1040 | | |
| tgg | att | tct | gaa | gtt | ctt | gag | aat | att | aag | ctt | gta | aat | aaa | gtt | gtt | 3168 |
| Trp | Ile | Ser | Glu | Val | Leu | Glu | Asn | Ile | Lys | Leu | Val | Asn | Lys | Val | Val | |
| | | | | 1045 | | | | | 1050 | | | | | 1055 | | |
| ggt | gag | aca | tgt | gaa | aga | agg | aac | att | gaa | gtt | act | gtg | cat | gaa | gtt | 3216 |
| Gly | Glu | Thr | Cys | Glu | Arg | Arg | Asn | Ile | Glu | Val | Thr | Val | His | Glu | Val | |
| | | 1060 | | | | | 1065 | | | | | 1070 | | | | |
| gca | aag | act | acc | act | tat | gta | gca | cca | tct | ttt | tca | gct | tat | act | caa | 3264 |
| Ala | Lys | Thr | Thr | Thr | Tyr | Val | Ala | Pro | Ser | Phe | Ser | Ala | Tyr | Thr | Gln | |
| | | 1075 | | | | | 1080 | | | | | 1085 | | | | |
| aga | gca | aac | gaa | gaa | atg | gag | ggt | ttt | cag | gat | aca | ata | gat | gaa | tta | 3312 |
| Arg | Ala | Asn | Glu | Glu | Met | Glu | Gly | Phe | Gln | Asp | Thr | Ile | Asp | Glu | Leu | |
| | | 1090 | | | | | 1095 | | | | | 1100 | | | | |
| aag | gat | aaa | cta | ctt | gga | gga | tca | cct | gag | ctt | gat | gtc | atc | tca | atc | 3360 |
| Lys | Asp | Lys | Leu | Leu | Gly | Gly | Ser | Pro | Glu | Leu | Asp | Val | Ile | Ser | Ile | |
| 1105 | | | | 1110 | | | | | 1115 | | | | | 1120 | | |
| gtt | ggc | atg | cca | gga | ttg | ggc | aag | act | aca | cta | gca | aag | aag | att | tac | 3408 |
| Val | Gly | Met | Pro | Gly | Leu | Gly | Lys | Thr | Thr | Leu | Ala | Lys | Lys | Ile | Tyr | |
| | | | | 1125 | | | | | 1130 | | | | | 1135 | | |
| aat | gat | cca | gaa | gtc | acc | tct | cgc | ttc | gat | gtc | cat | gct | caa | tgt | gtt | 3456 |
| Asn | Asp | Pro | Glu | Val | Thr | Ser | Arg | Phe | Asp | Val | His | Ala | Gln | Cys | Val | |
| | | 1140 | | | | | 1145 | | | | | 1150 | | | | |
| gtg | act | caa | tta | tat | tca | tgg | aga | gag | ttg | ttg | ctc | acc | att | ttg | aat | 3504 |
| Val | Thr | Gln | Leu | Tyr | Ser | Trp | Arg | Glu | Leu | Leu | Leu | Thr | Ile | Leu | Asn | |
| | | 1155 | | | | | 1160 | | | | | 1165 | | | | |
| gat | gtc | ctt | gag | cct | tct | gat | cgc | aat | gaa | aaa | gaa | gat | ggt | gaa | ata | 3552 |
| Asp | Val | Leu | Glu | Pro | Ser | Asp | Arg | Asn | Glu | Lys | Glu | Asp | Gly | Glu | Ile | |
| | | 1170 | | | | | 1175 | | | | | 1180 | | | | |
| gct | gat | gag | tta | cgc | cga | ttt | ttg | ttg | acc | aag | aga | ttc | ttg | att | ctc | 3600 |
| Ala | Asp | Glu | Leu | Arg | Arg | Phe | Leu | Leu | Thr | Lys | Arg | Phe | Leu | Ile | Leu | |
| 1185 | | | | 1190 | | | | | 1195 | | | | | 1200 | | |
| att | gat | gat | gtg | tgg | gac | tat | aaa | gtg | tgg | gac | aat | cta | tgt | atg | tgc | 3648 |
| Ile | Asp | Asp | Val | Trp | Asp | Tyr | Lys | Val | Trp | Asp | Asn | Leu | Cys | Met | Cys | |
| | | | | 1205 | | | | | 1210 | | | | | 1215 | | |
| ttc | agt | gat | gtt | tca | aat | agg | agt | aga | att | atc | cta | aca | acc | cgc | ttg | 3696 |
| Phe | Ser | Asp | Val | Ser | Asn | Arg | Ser | Arg | Ile | Ile | Leu | Thr | Thr | Arg | Leu | |
| | | 1220 | | | | | 1225 | | | | | 1230 | | | | |
| aat | gat | gtc | gcc | gaa | tat | gtc | aaa | tgt | gaa | agt | gat | ccc | cat | cat | ctt | 3744 |
| Asn | Asp | Val | Ala | Glu | Tyr | Val | Lys | Cys | Glu | Ser | Asp | Pro | His | His | Leu | |
| | | 1235 | | | | | 1240 | | | | | 1245 | | | | |
| cgt | tta | ttc | aga | gat | gac | gag | agt | tgg | aca | tta | tta | cag | aaa | gaa | gtc | 3792 |
| Arg | Leu | Phe | Arg | Asp | Asp | Glu | Ser | Trp | Thr | Leu | Leu | Gln | Lys | Glu | Val | |
| | | 1250 | | | | | 1255 | | | | | 1260 | | | | |
| ttt | caa | gga | gag | agc | tgt | cca | cct | gaa | ctt | gaa | gat | gtg | gga | ttt | gaa | 3840 |
| Phe | Gln | Gly | Glu | Ser | Cys | Pro | Pro | Glu | Leu | Glu | Asp | Val | Gly | Phe | Glu | |
| 1265 | | | | 1270 | | | | | 1275 | | | | | 1280 | | |
| ata | tca | aaa | agt | tgt | aga | ggg | ttg | cct | ctc | tca | gtt | gtg | tta | gta | gct | 3888 |
| Ile | Ser | Lys | Ser | Cys | Arg | Gly | Leu | Pro | Leu | Ser | Val | Val | Leu | Val | Ala | |
| | | | | 1285 | | | | | 1290 | | | | | 1295 | | |
| ggt | gtt | ctg | aaa | cag | aaa | aag | aag | aca | cta | gat | tca | tgg | aaa | gta | gta | 3936 |
| Gly | Val | Leu | Lys | Gln | Lys | Lys | Lys | Thr | Leu | Asp | Ser | Trp | Lys | Val | Val | |
| | | | | 1300 | | | | | 1305 | | | | | 1310 | | |
| gaa | caa | agt | cta | agt | tcc | cag | agg | att | ggc | agc | ttg | gaa | gag | agc | ata | 3984 |
| Glu | Gln | Ser | Leu | Ser | Ser | Gln | Arg | Ile | Gly | Ser | Leu | Glu | Glu | Ser | Ile | |
| | | 1315 | | | | | 1320 | | | | | 1325 | | | | |
| tct | ata | att | gga | ttc | agt | tac | aag | aat | tta | cca | cac | tat | ctt | aag | cct | 4032 |

```
                                                              -continued

Ser Ile Ile Gly Phe Ser Tyr Lys Asn Leu Pro His Tyr Leu Lys Pro
    1330                1335                1340 tgt ttt ctc tat ttt gga gga ttt ttg cag gga aag gat att cat gtc      4080
Cys Phe Leu Tyr Phe Gly Gly Phe Leu Gln Gly Lys Asp Ile His Val
1345                1350                1355                1360 tca aaa atg acc aag ttg tgg gta gct gaa ggg ttt gta caa gca aac      4128
Ser Lys Met Thr Lys Leu Trp Val Ala Glu Gly Phe Val Gln Ala Asn
                1365                1370                1375 aac gaa aaa gga caa gaa gat acc gca caa ggt ttc ttg gac gat ctt      4176
Asn Glu Lys Gly Gln Glu Asp Thr Ala Gln Gly Phe Leu Asp Asp Leu
            1380                1385                1390 att ggt agg aat gta gtg atg gcc atg gag aag aga cct aat acc aag      4224
Ile Gly Arg Asn Val Val Met Ala Met Glu Lys Arg Pro Asn Thr Lys
        1395                1400                1405 gtg aaa acg tgc cgc att cat gat ttg ttg cat aaa ttc tgc atg gaa      4272
Val Lys Thr Cys Arg Ile His Asp Leu Leu His Lys Phe Cys Met Glu
    1410                1415                1420 aag gcc aaa caa gag gat ttt ctt ctc caa atc aat agt gga gaa ggt      4320
Lys Ala Lys Gln Glu Asp Phe Leu Leu Gln Ile Asn Ser Gly Glu Gly
1425                1430                1435                1440 gta ttt cct gaa cga ttg gag gaa tac cga ttg ttc gtt cat tct tac      4368
Val Phe Pro Glu Arg Leu Glu Glu Tyr Arg Leu Phe Val His Ser Tyr
                1445                1450                1455 caa gat gaa att gat ctg tgg cgc cca tct cgc tct aat gtc cga tct      4416
Gln Asp Glu Ile Asp Leu Trp Arg Pro Ser Arg Ser Asn Val Arg Ser
            1460                1465                1470 tta cta ttc aat gca att gat cca gat aac ttg tta tgg ccg cgt gat      4464
Leu Leu Phe Asn Ala Ile Asp Pro Asp Asn Leu Leu Trp Pro Arg Asp
        1475                1480                1485 atc tcc ttc att ttt gag agc ttc aag ctt gtt aaa gtg ttg gat ttg      4512
Ile Ser Phe Ile Phe Glu Ser Phe Lys Leu Val Lys Val Leu Asp Leu
    1490                1495                1500 gaa tca ttc aac att ggt ggt act ttt ccc act gaa ata caa tat cta      4560
Glu Ser Phe Asn Ile Gly Gly Thr Phe Pro Thr Glu Ile Gln Tyr Leu
1505                1510                1515                1520 att cag atg aag tac ttt gcg gcc caa act gat gca aat tca att cct      4608
Ile Gln Met Lys Tyr Phe Ala Ala Gln Thr Asp Ala Asn Ser Ile Pro
                1525                1530                1535 tca tct ata gct aag ctt gaa aat ctt gag act ttt gtc gta aga gga      4656
Ser Ser Ile Ala Lys Leu Glu Asn Leu Glu Thr Phe Val Val Arg Gly
            1540                1545                1550 ttg gga gga gag atg ata tta cct tgt tca ctt ctg aag atg gtg aaa      4704
Leu Gly Gly Glu Met Ile Leu Pro Cys Ser Leu Leu Lys Met Val Lys
        1555                1560                1565 ttg agg cat ata cat gta aat gat cgg gtt tct ttt ggt ttg cat gag      4752
Leu Arg His Ile His Val Asn Asp Arg Val Ser Phe Gly Leu His Glu
    1570                1575                1580 aac atg gat gtt tta act ggt aac tca caa tta cct aat ttg gaa acc      4800
Asn Met Asp Val Leu Thr Gly Asn Ser Gln Leu Pro Asn Leu Glu Thr
1585                1590                1595                1600 ttt tct act cca cgt ctc ttt tat ggt aaa gac gca gag aag gtt ttg      4848
Phe Ser Thr Pro Arg Leu Phe Tyr Gly Lys Asp Ala Glu Lys Val Leu
                1605                1610                1615 agg aag atg cca aaa ttg aga aaa ttg agt tgc ata ttt tca ggg aca      4896
Arg Lys Met Pro Lys Leu Arg Lys Leu Ser Cys Ile Phe Ser Gly Thr
            1620                1625                1630 ttt ggt tat tca agg aaa ttg aag ggt agg tgt gtt cgt ttt ccc aga      4944
Phe Gly Tyr Ser Arg Lys Leu Lys Gly Arg Cys Val Arg Phe Pro Arg
        1635                1640                1645
```

-continued

```
tta gat ttt cta agt cac ctt gag tcc ctc aag ctg gtt tcg aac agc      4992
Leu Asp Phe Leu Ser His Leu Glu Ser Leu Lys Leu Val Ser Asn Ser
    1650                1655                1660 tat cca gcc aaa ctt cct cac aag ttc aat ttc ccc tcg caa cta agg      5040
Tyr Pro Ala Lys Leu Pro His Lys Phe Asn Phe Pro Ser Gln Leu Arg
1665                1670                1675                1680 gaa ctg act tta tca aag ttc cgt cta cct tgg acc caa att tcg atc      5088
Glu Leu Thr Leu Ser Lys Phe Arg Leu Pro Trp Thr Gln Ile Ser Ile
                1685                1690                1695 att gca gaa ctg ccc aac ttg gta att ctt aag tta ttg ctc aga gcc      5136
Ile Ala Glu Leu Pro Asn Leu Val Ile Leu Lys Leu Leu Leu Arg Ala
            1700                1705                1710 ttt gaa ggg gat cac tgg gaa gtg aaa gat tca gag ttc cta gaa ctc      5184
Phe Glu Gly Asp His Trp Glu Val Lys Asp Ser Glu Phe Leu Glu Leu
        1715                1720                1725 aaa tac tta aaa ctg gac aac ctc aaa gtt gta caa tgg tcc atc tct      5232
Lys Tyr Leu Lys Leu Asp Asn Leu Lys Val Val Gln Trp Ser Ile Ser
    1730                1735                1740 gat gat gct ttt cct aag ctt gaa cat ttg gtt tta acg aaa tgt aag      5280
Asp Asp Ala Phe Pro Lys Leu Glu His Leu Val Leu Thr Lys Cys Lys
1745                1750                1755                1760 cat ctt gag aaa atc cct tct cgt ttt gaa gat gct gtt tgc cta aat      5328
His Leu Glu Lys Ile Pro Ser Arg Phe Glu Asp Ala Val Cys Leu Asn
                1765                1770                1775 aga gtt gag gtg aac tgg tgc aac tgg aat gtt gcc aat tca gcc caa      5376
Arg Val Glu Val Asn Trp Cys Asn Trp Asn Val Ala Asn Ser Ala Gln
            1780                1785                1790 gat att caa act atg caa cat gaa gtt ata gca aat gat tca ttc aca      5424
Asp Ile Gln Thr Met Gln His Glu Val Ile Ala Asn Asp Ser Phe Thr
        1795                1800                1805 gtt act ata cag cct cca gat tgg tct aaa gaa cag ccc ctt gac tct      5472
Val Thr Ile Gln Pro Pro Asp Trp Ser Lys Glu Gln Pro Leu Asp Ser
    1810                1815                1820 tag                                                                   5475
1825
```

<210> SEQ ID NO 4
<211> LENGTH: 416
<212> TYPE: PRT
<213> ORGANISM: Lycopersicon esculentum

<400> SEQUENCE: 4

```
Val Met Ala Met Glu Lys Arg Pro Asn Thr Lys Val Lys Thr Cys Arg
  1               5                  10                  15

Ile His Asp Leu Leu His Lys Phe Cys Met Glu Lys Ala Lys Gln Glu
             20                  25                  30

Asp Phe Leu Leu Gln Ile Asn Ser Gly Glu Gly Val Phe Pro Glu Arg
         35                  40                  45

Leu Glu Glu Tyr Arg Leu Phe Val His Ser Tyr Gln Asp Glu Ile Asp
     50                  55                  60

Leu Trp Arg Pro Ser Arg Ser Asn Val Arg Ser Leu Leu Phe Asn Ala
 65                  70                  75                  80

Ile Asp Pro Asp Asn Leu Leu Trp Pro Arg Asp Ile Ser Phe Ile Phe
                 85                  90                  95

Glu Ser Phe Lys Leu Val Lys Val Leu Asp Leu Glu Ser Phe Asn Ile
            100                 105                 110

Gly Gly Thr Phe Pro Thr Glu Ile Gln Tyr Leu Ile Gln Met Lys Tyr
        115                 120                 125
```

```
Phe Ala Ala Gln Thr Asp Ala Asn Ser Ile Pro Ser Ser Ile Ala Lys
        130                 135                 140

Leu Glu Asn Leu Glu Thr Phe Val Val Arg Gly Leu Gly Gly Glu Met
145                 150                 155                 160

Ile Leu Pro Cys Ser Leu Leu Lys Met Val Lys Leu Arg His Ile His
                    165                 170                 175

Val Asn Asp Arg Val Ser Phe Gly Leu His Glu Asn Met Asp Val Leu
                180                 185                 190

Thr Gly Asn Ser Gln Leu Pro Asn Leu Glu Thr Phe Ser Thr Pro Arg
            195                 200                 205

Leu Phe Tyr Gly Lys Asp Ala Glu Lys Val Leu Arg Lys Met Pro Lys
        210                 215                 220

Leu Arg Lys Leu Ser Cys Ile Phe Ser Gly Thr Phe Gly Tyr Ser Arg
225                 230                 235                 240

Lys Leu Lys Gly Arg Cys Val Arg Phe Pro Arg Leu Asp Phe Leu Ser
                245                 250                 255

His Leu Glu Ser Leu Lys Leu Val Ser Asn Ser Tyr Pro Ala Lys Leu
                260                 265                 270

Pro His Lys Phe Asn Phe Pro Ser Gln Leu Arg Glu Leu Thr Leu Ser
            275                 280                 285

Lys Phe Arg Leu Pro Trp Thr Gln Ile Ser Ile Ala Glu Leu Pro Asn
        290                 295                 300

Leu Val Ile Leu Lys Leu Leu Arg Ala Phe Glu Gly Asp His Trp
305                 310                 315                 320

Glu Val Lys Asp Ser Glu Phe Leu Glu Leu Lys Tyr Leu Lys Leu Asp
                325                 330                 335

Asn Leu Lys Val Val Gln Trp Ser Ile Ser Asp Asp Ala Phe Pro Lys
                340                 345                 350

Leu Glu His Leu Val Leu Thr Lys Cys Lys His Leu Glu Lys Ile Pro
            355                 360                 365

Ser Arg Phe Glu Asp Ala Val Cys Leu Asn Arg Val Glu Val Asn Trp
        370                 375                 380

Cys Asn Trp Asn Val Ala Asn Ser Ala Gln Asp Ile Gln Thr Met Gln
385                 390                 395                 400

His Glu Val Ile Ala Asn Asp Ser Phe Thr Val Thr Ile Gln Pro Pro
                405                 410                 415

<210> SEQ ID NO 5
<211> LENGTH: 143
<212> TYPE: PRT
<213> ORGANISM: Lycopersicon esculentum

<400> SEQUENCE: 5

Ser Ser Thr Glu Lys Met Arg Pro Leu Leu Ser Asp Phe Leu Gln Glu
1               5                   10                  15

Ile Glu Ser Val Lys Val Glu Phe Arg Asn Val Cys Leu Gln Val Leu
                20                  25                  30

Asp Ile Ser Pro Phe Ser Leu Thr Asp Gly Glu Gly Leu Val Asn Phe
            35                  40                  45

Leu Leu Lys Asn Gln Ala Lys Val Pro Asn Asp Ala Val Ser Ser
        50                  55                  60

Asp Gly Ser Leu Glu Asp Ala Ser Ser Thr Glu Lys Met Gly Leu Pro
65                  70                  75                  80

Ser Asp Phe Leu Arg Glu Ile Glu Ser Val Glu Ile Lys Glu Ala Arg
                85                  90                  95
```

```
Lys Leu Tyr Asp Gln Val Leu Asp Ala Thr His Cys Glu Thr Ser Lys
            100                 105                 110

Thr Asp Gly Lys Ser Phe Ile Asn Ile Met Leu Thr Gln Gln Asp Lys
        115                 120                 125

Leu Pro Asp Tyr Asp Ala Gly Ser Val Ser Tyr Leu Leu Asn Gln
        130                 135                 140
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
ccaagtgcag agagtactgg a                                              21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
tgaatgaaca tgatcaaagt atgc                                           24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
actccagaac caatgattgc ata                                            23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
ggaatttaaa tctagaatat ctc                                            23

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
ccttctattc atcatcc                                                   17

<210> SEQ ID NO 11
<211> LENGTH: 17
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 11
ctgctcctga ttcttct                                                        17

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
ttgcattgac gtcgactatc caggtttttt tttttttt                                 38

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
taagatatgt aaccatgagc aacaaccctt c                                        31

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
gacctcatct gcaatagta                                                      19

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
aggccctgca ctgataaaga acaa                                                24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
agcagctctg ggatcacttg cctt                                                24

<210> SEQ ID NO 17
<211> LENGTH: 24
<212> TYPE: PRT
<213> ORGANISM: Artificial Sequence
```

```
<220> FEATURE:
<223> OTHER INFORMATION: Description of Artificial Sequence: Consensus
      sequence

<400> SEQUENCE: 17

Leu Xaa Xaa Leu Xaa Xaa Leu Xaa Xaa Leu Xaa Leu Xaa Xaa Xaa Xaa
 1               5                   10                  15

Xaa Leu Xaa Xaa Ile Pro Ser Xaa
                20
```